United States Patent [19]
Los

[11] Patent Number: 5,073,186
[45] Date of Patent: Dec. 17, 1991

[54] 5-THIOXO-2-IMIDAZOLINYL BENZOIC ACIDS, ESTERS, SALTS & RELATED COMPOUNDS, AND USE THEREOF AS HERBICIDAL AGENTS

[75] Inventor: Marinus Los, Pennington, N.J.

[73] Assignee: American Cyanamid Company, Stamford, Conn.

[21] Appl. No.: 463,590

[22] Filed: Jan. 11, 1990

Related U.S. Application Data

[60] Division of Ser. No. 629,296, Jul. 9, 1984, Pat. No. 4,911,747, which is a continuation-in-part of Ser. No. 519,615, Aug. 2, 1983, abandoned.

[51] Int. Cl.$^5$ .................. A01N 43/48; C07D 233/04
[52] U.S. Cl. ........................................ 71/92; 548/301; 548/302

[58] Field of Search ................... 548/301, 302; 71/92; 546/278

[56] References Cited

U.S. PATENT DOCUMENTS 4,658,030 4/1987 Barton et al. ...................... 546/278

Primary Examiner—Mary C. Lee
Assistant Examiner—Joseph K. McKane
Attorney, Agent, or Firm—John W. Hogan, Jr.

[57] ABSTRACT

This invention relates to novel thioxo-2-imidazolinyl benzoic acids, esters and salts, a process for the preparation thereof and a method for the control of undesirable monocotyledonous and dicotyledonous plant species therewith.

20 Claims, No Drawings

5-THIOXO-2-IMIDAZOLINYL BENZOIC ACIDS, ESTERS, SALTS & RELATED COMPOUNDS, AND USE THEREOF AS HERBICIDAL AGENTS

This is a divisional of co-pending application Ser. No. 06/629,296, filed on July 9, 1984, now U.S. Pat. No. 4,911,747, which is a Continuation-in-Part of Ser. No. 519,615, filed Aug. 2, 1983 now abandoned.

This invention relates to novel thioxo-2-imidazolinyl benzoic acids, esters and salts, a process for the preparation thereof and a method for the control of undesirable monocotyledonous and dicotyledonous plant species therewith.

The invention relates, more particularly, to herbicidally effective formula I, thioxo-2-imidazolinyl benzoic acids, and their esters and salts; formula II, 3-thio-5H-imidazo[2,1-a]isoindole-3(2H),5-diones; formula III, 2-thio-5H-imidazo[2,1-a]isoindole-2(3H),5-diones; and formula IV, 1,9-b-dihydro-2-thio-5H-imidazo[2,1-a]isoindole-2(3H),5-diones, depicted by the following structures:

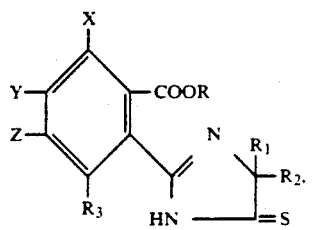
(I)

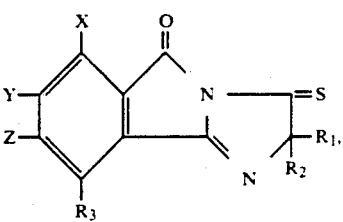
(II)

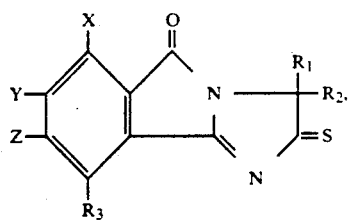
(III)

and

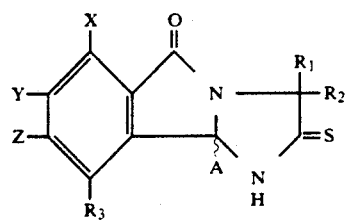
(IV)

wherein R is hydrogen;
$C_1$-$C_{12}$ alkyl optionally substituted with one of the following groups: $C_1$-$C_4$ alkoxy, halogen, hydroxyl, $C_3$-$C_6$ cycloalkyl, benzyloxy, furyl, phenyl, halophenyl, $C_1$-$C_4$ alkylphenyl, $C_1$-$C_4$ alkoxyphenyl nitrophenyl, carboxyl, $C_1$-$C_3$ alkoxycarbonyl, cyano or tri($C_1$-$C_3$)alkylammonium;

$C_3$-$C_{12}$ alkenyl optionally substituted with one of the following groups: $C_1$-$C_3$ alkoxy, phenyl, halogen, or $C_1$-$C_3$ alkoxycarbonyl or with two $C_1$-$C_4$ alkoxy groups or two halogen atoms;

$C_3$-$C_6$ cycloalkyl optionally substituted with one or two $C_1$-$C_3$ alkyl groups;

$C_3$-$C_{10}$ alkynyl; or, a cation, as for example, alkali metals, alkaline earth metals, maganese, copper, iron, zinc, cobalt, lead, silver, nickel, ammonium, organic ammonium, or the like;

$R_1$ and $R_2$ each represent $C_1$-$C_3$ alkyl or cyclopropyl, with the proviso that the sum of the number of carbon atoms in $R_1$ and $R_2$ is 2 to 5; and when $R_1$ and $R_2$ are taken together with the carbon to which they are attached, they may form a $C_3$-$C_6$ cycloalkyl ring optionally substituted with methyl;

A is hydrogen, hydroxyl, $C_3$-$C_6$ alkenyloxy, $C_3$-$C_6$ alkynyloxy, $C_1$-$C_6$ alkylthio, $NR_{13}R_{14}$ or $C_1$-$C_6$ alkoxy optionally substituted with phenyl, halophenyl, $C_1$-$C_3$ alkylphenyl, $C_1$-$C_3$ alkoxyphenyl or di-$C_1$-$C_3$ alkylaminophenyl;

$R_{13}$ is hydrogen, $C_1$-$C_4$ alkyl optionally substituted with phenyl, halophenyl, $C_1$-$C_3$ alkylphenyl or $C_1$-$C_3$ alkoxyphenyl;

$R_{14}$ is hydrogen or $C_1$-$C_4$ alkyl;

X is hydrogen, halogen or methyl;

Y and Z are each hydrogen, halogen, $C_1$-$C_6$ alkyl, $C_1$-$C_4$ hydroxyalkyl, $C_1$-$C_6$ alkoxy, $C_1$-$C_4$ alkylthio, phenoxy, $C_1$-$C_4$ haloalkyl, $OCF_2CHF_2$, $OCF_3$, $OCHF_2$, nitro, cyano, $NR_4R_5$, $C_3$-$C_8$ straight or branched alkenyloxy optionally substituted with one to three halogens, $C_3$-$C_8$ straight or branched alkynyloxy optionally substituted with one to three halogens, or phenyl optionally substituted with one $C_1$-$C_4$ alkyl, $C_1$-$C_4$ alkoxy or halogen;

$R_3$ is hydrogen, halogen, $C_1$-$C_4$ alkyl, $C_1$-$C_4$ alkylthio, $C_1$-$C_4$ alkoxy, $CF_3$, $NO_2$, $OCF_3$, $OCHF_2$ or $OCF_2CHF_2$;

$R_4$ is hydrogen or $C_1$-$C_4$ alkyl;

$R_5$ is $C_1$-$C_4$ alkyl;

And, when taken together, Y and Z may form a ring in which YZ is represented by
(1) the structure: —$(CH_2)_n$—, where n is an integer of 2, 3 or 4; or
(2) by the structure:

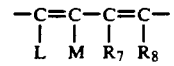

where, L, M, $R_7$ and $R_8$ each represent hydrogen, halogen, $C_1$-$C_4$ alkyl or $C_1$-$C_3$ alkoxy, and X is hydrogen;

and when $R_1$ and $R_2$ are not the same, the optical isomers thereof and except when R is a cation, the acid addition salts thereof.

As used in the present specification and claims, the term "halogen" means F, Cl, Br or I, unless otherwise specified.

In the present specification and claims, the alkali metals include: sodium, potassium and lithium, although sodium is generally preferred. Also, in the present specification and claims, unless otherwise specified, the term "organic ammonium" is defined as a group consisting of a positively charged nitrogen atom joined to from one to four aliphatic groups, each containing from one to 20 carbon atoms. Among the organic ammonium groups which are illustrative for the preparation of the aliphatic ammonium salts of the imidazolidinyl acids are: monoalkylammonium, dialkylammonium, trialklammonium, tetraalkylammonium, monoalkenylammonium, dialkenylammonium trialkenylammonium, monoalkynylammonium, dialkynylammonium, trialkynylammonium, monoalkanolammonium, dialkanolammonium, trialkanolammonium, $C_5$–$C_6$ cycloalkylammonium, piperidinium, morpholinium, pyrrolidinium, benzylammonium and equivalents thereof.

Although some 5-oxo-2-imidazolinyl benzoic acids, esters and salts, dihydroimidazoisoindoledione and imidazoisoindoledione are respectively described as herbicidal agents in U.S. Pat. No. 4,188,487, issued Feb. 20, 1980, U.S. Pat. No. 4,041,045, issued Aug. 9, 1977 and U.S. Pat. No. 4,017,510, issued Apr. 12, 1977; said patents do not teach, suggest or disclose, the substituted or unsubstituted 5-thioxo-2-imidazolinyl benzoic acids, esters and salts, the 2-thio-dihydroimidazoisoimidoledione or the 2 or 3 thio-imidazoisoindoledione of the present invention. It was therefore surprising to find that the compounds of the present invention, as shown and described above, are highly effective, selective, herbicidal agents, remarkably effective for the control of quackgrass, in the presence of graminaceous crops such as rice, barley, wheat, corn, turf, and the like.

In accordance with the present invention, formula I substituted and unsubstituted 5-thioxo-2-(2-imdazolin-2-yl)benzoic acids, esters and salts represented by the structure:

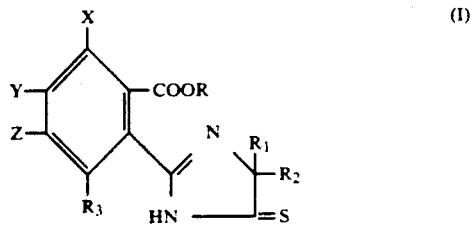

(I)

where R, $R_1$, $R_2$, $R_3$, W, X, Y and Z are as described above, can be prepared by reaction of a formula XVII substituted or unsubstituted phthalic acid with acetic anhydride, dimethoxyethane and pyridine to give the corresponding phthalic anhydride. The thus-prepared phthalic anhydride of formula XVIII is then admixed with an equivalent amount of a formula XXVI thiocarboxamide, in the presence of an inert organic solvent such as a low-boiling ether (diethyl ether, tetrahydrofuran, dimethoxyethane) acetonitrile, ethyl acetate or a halogenated hydrocarbon, at a temperature between 20 and 60° C. and preferably 25° to 30° C. under a blanket of inert gas such as nitrogen. When the reaction is essentially complete, the product is isolated by any convenient means, e.g., filtration, distillation of the solvent or by extraction into aqueous base if the solvent is water immiscible. The reaction yields the isomeric phthalamic monoacid/monoamide products, formulas XXVIIa and XXVIIb.

The thus-formed mixture is then heated to about 25° to 100° C., with about 2 to 10 molar equivalents of aqueous alcoholic sodium or potassium hydroxide. The reaction is preferably conducted under a blanket of inert gas, such as nitrogen. If the product is insoluble in water, it will precipitate from the aqueous phase and be recovered by filtration or extraction. If the product is soluble in water, the mixture can be extracted with an organic solvent such as ether, methylene chloride or the like, and the extract concentrated to provide an isomeric mixture of the formula XXVIIIa and XXVIIIb substituted or unsubstituted 2-(5-thioxo-2-imidazolin-2-yl)benzoic acids. Advantageously, the formula XXVIIIa 2-(5-thioxo-2-imidazolin-2-yl)benzoic acid can be dispersed in a non-protic solvent such as tetrahydrofuran and treated with an equimolar amount of dicyclohexylcarbodiimide to yield the corresponding formula II substituted or unsubstituted tricyclic 3-thio-imidazo[2,1-a]isoindole-3(2H), 5-dione. This reaction is generally conducted at ambient temperature, preferably under a blanket of inert gas such as nitrogen. The thus-formed formula II tricyclic 3-thio-imidazoisoindole-3(2H),5-dione may then be ring opened by reaction with an alcohol in the presence of the corresponding alkali metal alkoxide, thus affording the formula I ester. The alkoxide is conveniently prepared by reaction of the alcohol with an alkali metal or its hydride. The alcohol may be illustrated by the formula ROH, wherein R is $C_1$–$C_{12}$ alkyl optionally substituted with one of the following groups: $C_1$–$C_4$ alkoxy, halogen, hydroxyl, $C_3$–$C_6$ cycloalkyl, benzyloxy, furyl, phenyl, halophenyl, $C_1$–$C_4$ alkylphenyl, $C_1$–$C_4$ alkoxyphenyl nitrophenyl, carboxyl, $C_1$–$C_3$ alkoxycarbonyl, cyano or tri($C_1$–$C_3$)alkylammonium;

$C_3$–$C_{12}$ alkenyl optionally substituted with one of the following groups: $C_1$–$C_3$ alkoxy, phenyl, halogen, or $C_1$–$C_3$ alkoxycarbonyl or with two $C_1$–$C_4$ alkoxy groups or two halogen atoms;

$C_3$–$C_6$ cycloalkyl optionally substituted with one or two $C_1$–$C_3$ alkyl groups; or $C_3$–$C_{10}$ alkynyl.

The formula II dione can also be rearranged to the corresponding formula III 2-thio-5H-imidazo[2,1-a]-isoindole-2(3H),5-dione by heating the same as a solution of acetic acid. A preferred method for the synthesis of the formula III 2-thio-5H-imidazo[2,1-a]-isoindole-2-(3H),5-dione consists of treating the corresponding benzoic acid of formula I with a slight excess of trifluoroacetic anhydride in a solvent such as THF, or the like at low temperature, preferably between −60° C. and −50° C. The thus-formed formula III 2-thio-5H-imidazo[2,1-a]isoindole-2(3H),5-dione can then be reduced with sodium borohydride in ethanol or aqueous ethanol to give the formula IV 1,9b-dihydro-2-thio-5H-imidazo[2,1-a]isoindole-2(3H),5-dione in which A is hydrogen as a mixture of isomers. Nucleophiles other than hydride ion such as water, alcohols, primary and secondary amines and mercaptans can be added to the >C=N— of Formula III dione to give formula IV diones in which A is hydrogen, hydroxyl, $C_3$–$C_6$ alkenyloxy, $C_3$–$C_6$ alkynyloxy, $C_1$–$C_6$ alkylthio, $NR_{13}R_{14}$ or $C_1$–$C_6$ alkoxy optionally substituted with phenyl, halophenyl, $C_1$–$C_3$ alkylphenyl, $C_1$–$C_3$ alkoxyphenyl or di-$C_1$–$C_3$ alkylaminophenyl;

$R_{13}$ is hydrogen, $C_1$–$C_4$ alkyl optionally substituted with phenyl, halophenyl, $C_1$–$C_3$ alkylphenyl or $C_1$–$C_3$ alkoxyphenyl;

$R_{14}$ is hydrogen or $C_1$–$C_4$ alkyl;

The above reactions are graphically illustrated in Flow Diagram I below.

FLOW DIAGRAM I
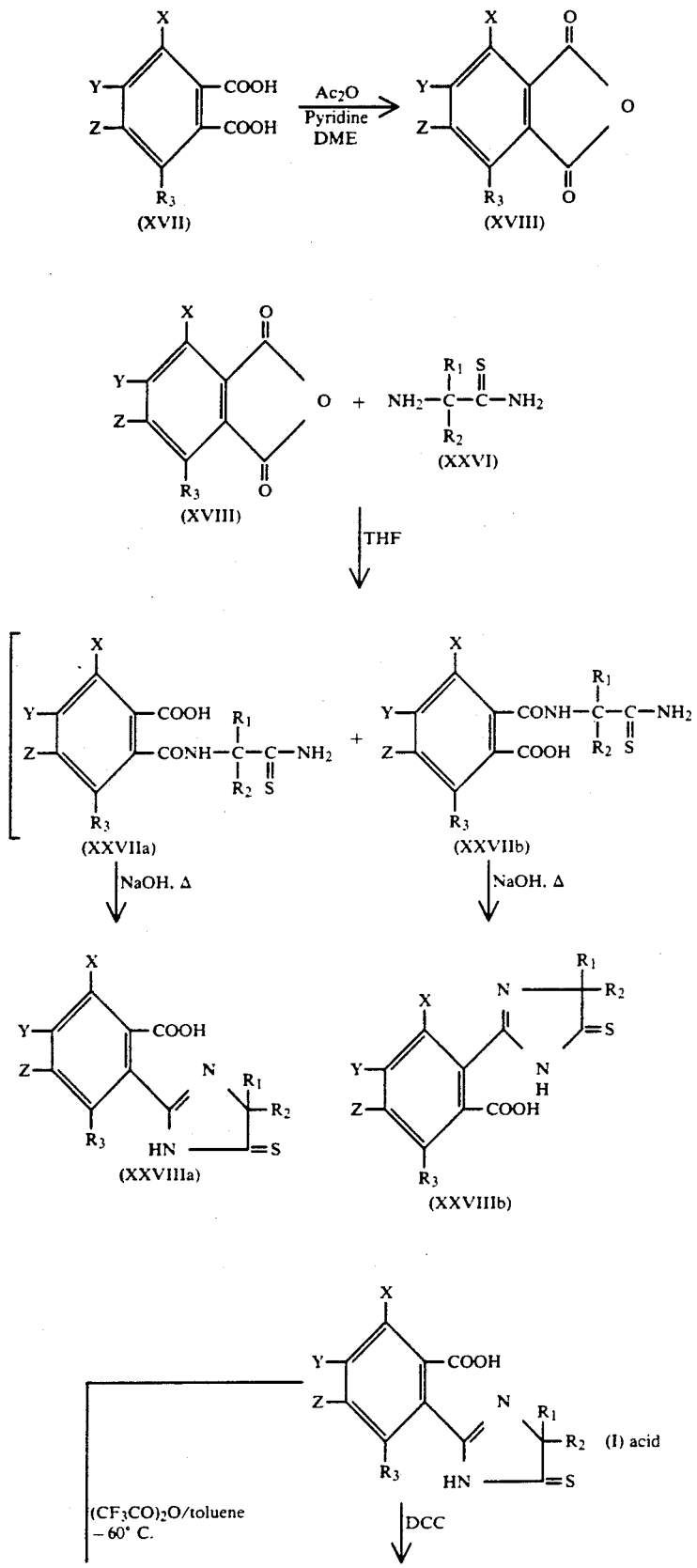

FLOW DIAGRAM 1
-continued

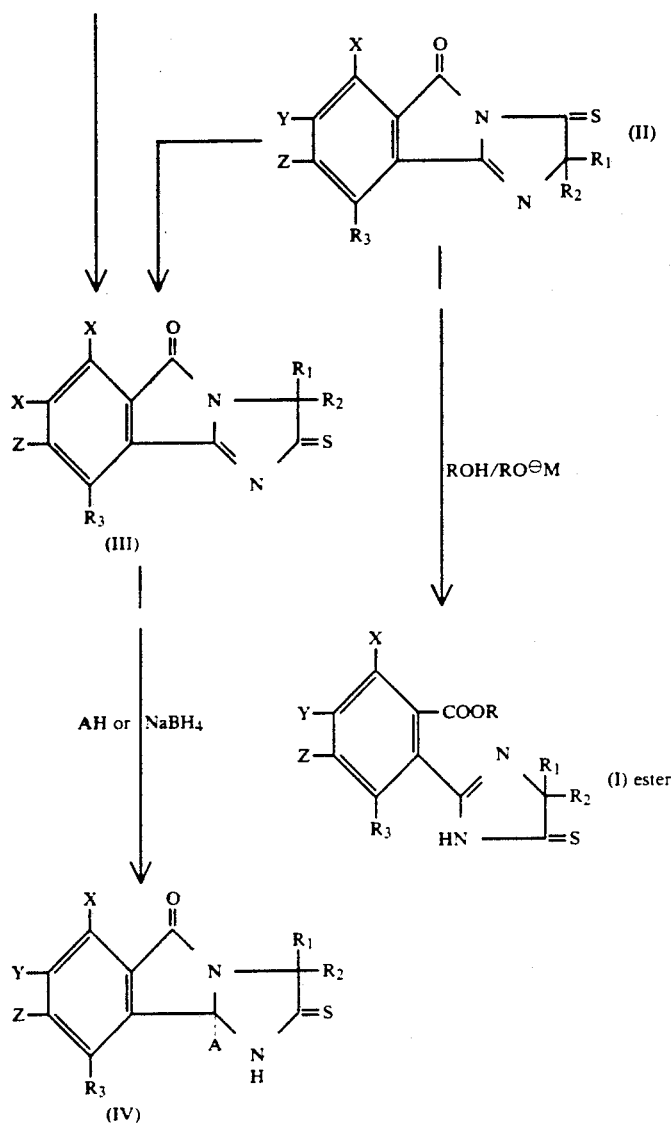

wherein M is Na or K; R is as described immediately above in reference to useful alcohols and A, X, Y, Z, R₁, R₂ and R₃ are as described above.

From the above discussion, it can be seen that the described synthetic route to 5-thioxo-2-(2-imidazolinyl)benzoic acids yields isomeric mixtures of the herbicidally effective acids. While these isomeric mixtures have been found to be very effective for the selective control of undesirable plant species, it has also been determined that, not infrequently, one of the isomers is somewhat more effective and/or selective than the other. Thus, it is sometimes desirable to direct a synthesis to a single isomer.

Another method for preparing mono-substituted and multi-substituted thioxo-2-(2-imidazolinyl)benzoic acids and esters of the present invention, involves the reaction of a formula XV, substituted benzoic acid with thionyl chloride and a catalytic amount of dimethylformamide to give the formula XXXIV substituted benzoyl chloride The reaction mixture is preferably heated to between 25° and 40° C. and then evaporated in vacuo with an anhydrous aromatic solvent such as toluene, to give the substituted benzoyl chloride. The thus obtained substituted benzoyl chloride is then admixed with equimolar amounts of a formula XXVI thiocarboxamide and a trialkylamine, such as triethylamine, triisopropylamine or the like, in the presence of an non-protic solvent such as tetrahydrofuran. During the addition of the reactants, the reaction mixture is generally maintained at a temperature between about 0° and 15° C. When addition is complete, the mixture is allowed to warm to ambient temperature, then treated with water and extracted with an organic solvent such as ethyl acetate to obtain the N-substituted benzamide of formula XXXV. The thus-formed N-substituted benzamide is then heated to a temperature of from 25° to 110° C. with about 2 to 10 molar equivalents of aqueous or aqueous alcoholic sodium or potassium hydroxide, preferably under a blanket of inert gas such as nitrogen. The reaction yields the formula XXXVI substituted phenyl imidazolinethione, which can be converted to the corresponding substituted (5-thioxo-2-imidazolin-2-yl) benzoic acid depicted by formula XXXVII, using sec-butyl lithium and carbon dioxide. This reaction is preferably carried out by dissolving or dispersing the formula XXXVI substituted phenyl imidazolinthione in tetrahydrofuran or other non-protic solvent and about three equivalents of tetramethylenediamine under a blanket of inert gas such as nitrogen. The reaction mixture is maintained at a temperature between about −70° and −50° C. and then treated with a solution of sec-butyl lithium in cyclohexane. Thereafter, the reaction mixture is admixed with tetrahydrofuran saturated with carbon dioxide to yield the formula XXXVII substituted (5-thioxo-2-imidazolin-2-yl)benzoic acid. These reactions are illustrated graphically in Flow Diagram II below.

of the reaction mixture between about −70° and −50° C. Thereafter, the reaction mixture is admixed with anhydrous tetrahydrofuran saturated with carbon dioxide to yield the formula XXXIX substituted phthalamic acid. Treatment of a stirred solution of the substituted phthalamic acid in dry tetrahydrofuran with ethyl chloroformate followed by triethylamine and a solution of a formula XXVI thiocarboxamide in anhydrous tetrahydrofuran, yields the substituted N,N-diethylphthalamide of formula XL. Base cyclization of the formula XL substituted N,N-diethylphthalamide can be achieved by heating said formula XL compound with from 2 to 10 molar equivalents of aqueous or aqueous

FLOW DIAGRAM II

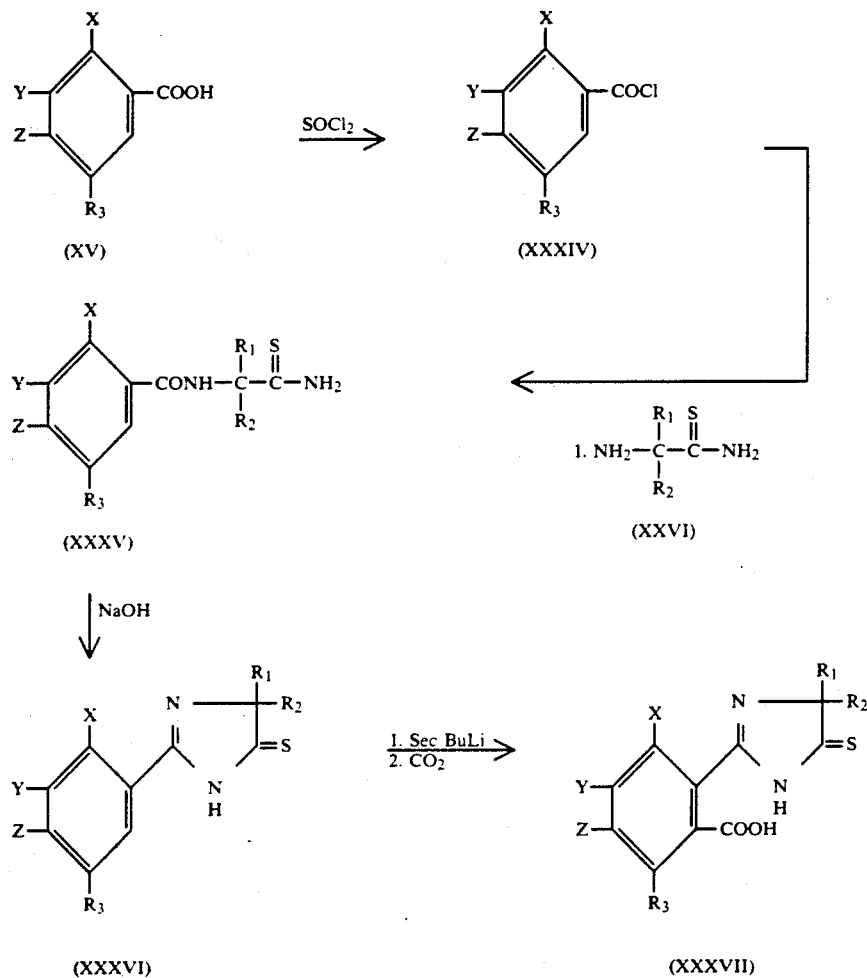

Alternatively, the formula XV substituted benzoic acid may be converted to the formula XXXIV benzoyl chloride, as described above. Thereafter, the benzoyl chloride is dispersed in tetrahydrofuran and admixed with a solution of 3 to 5 and preferably about 4 equivalents of diethylamine in tetrahydrofuran. Addition is generally conducted under a blanket of nitrogen while maintaining the temperature of the reaction mixture between about -10 and 0° C. The reaction yields the formula XXXVII substituted benzamide. The above-said substituted benzamide may then be dissolved in anhydrous tetrahydrofuran and treated with an equivalent amount of sec-butyl lithium dispersed in cyclohexane. This treatment is generally conducted under a blanket of nitrogen, while maintaining the temperature alcoholic sodium or potassium hydroxide to a temperature between about 25° and 110° C., preferably under a blanket of nitrogen. This reaction yields the formula XLI substituted N,N-diethyl(5-thioxo-2-imidazolin-2-yl)benzamide, which is readily converted to the corresponding acid of formula XLIII by heating with a concentrated mineral acid such as concentrated hydrochloric or hydrobromic acid. After acidification, the mixture is cooled, basified to a pH between 7 and 10, with alkali metal hydroxide, such as sodium hydroxide or potassium hydroxide and then carefully acified to pH 3 with concentrated sulfuric acid. The formula XLI substituted N,N-diethyl(5-thioxo-2-imidazolin-2-yl)benzamide salt also undergoes transesterification with methanol and hydrogen chloride, yielding the corresponding formula XLII methyl ester of the said formula XLI N,N-diethylbenzamide. Treatment of the formula XLII substituted methyl (5-thioxo-2-imidazolin-2-yl)benzoate with aqueous or aqueous alcoholic alkali metal hydroxide at an elevated temperature between about 60 and 100° C., followed by acidification with hydrochloric acid then yields the formula XLIII substituted (5-thioxo-2-imidazolin-2-yl)-benzoic acid. These reactions are illustrated in Flow Diagram III below.

FLOW DIAGRAM III

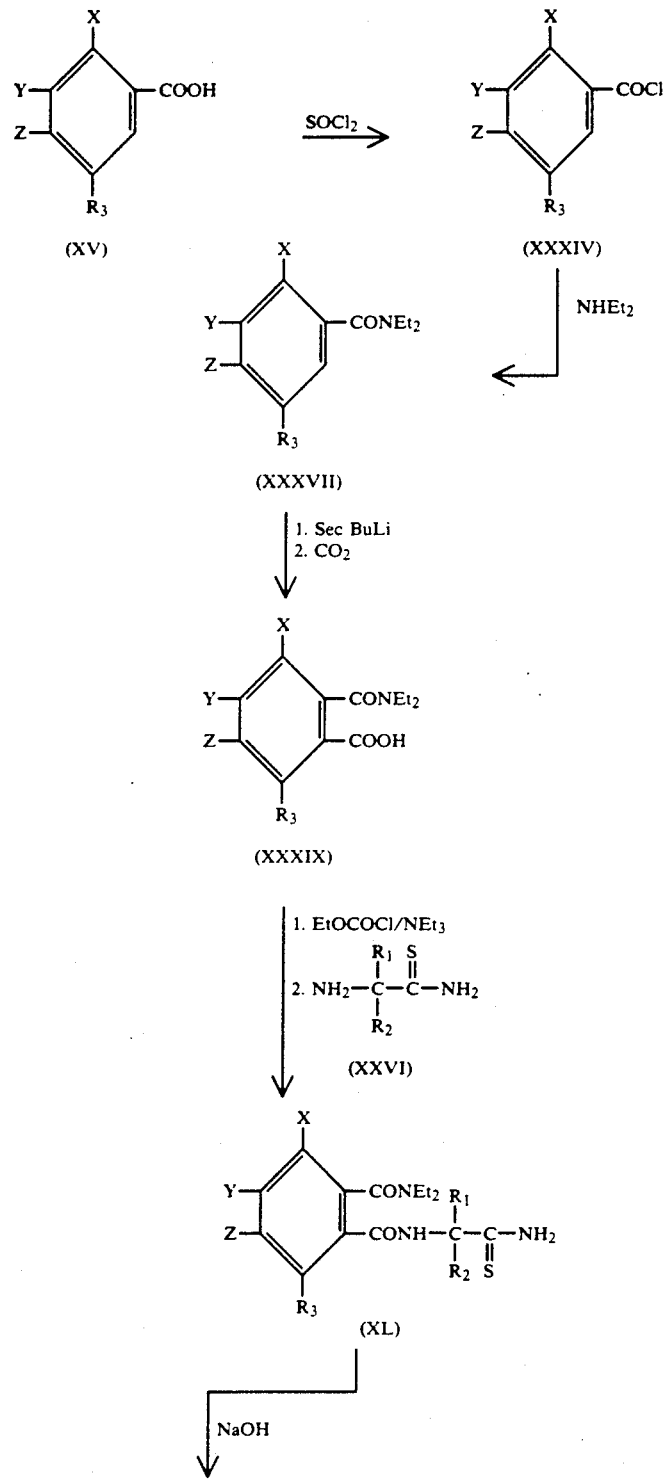

-continued
FLOW DIAGRAM III

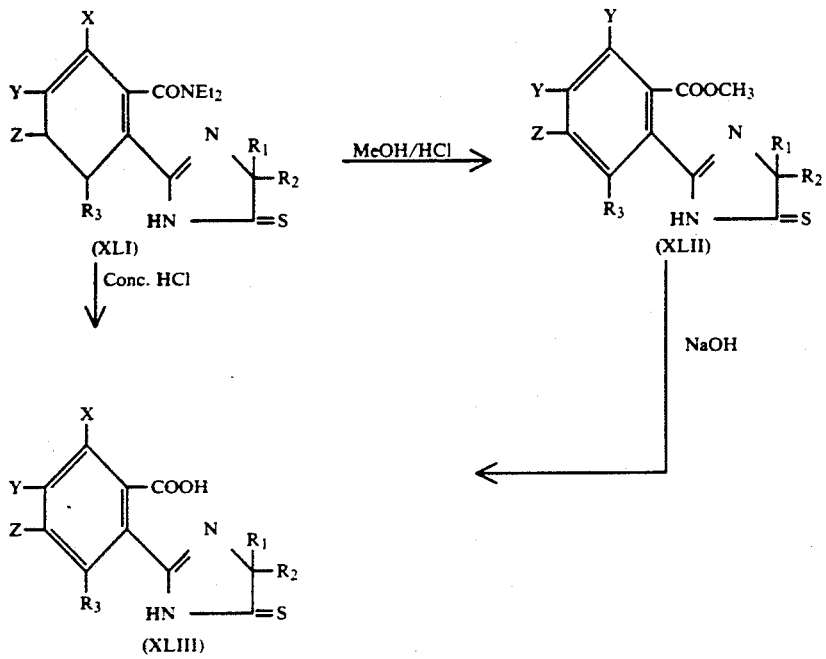

An alternative process for the preparation of substituted 2-(5-thioxo-2-imidazolin-2-yl)benzoic acids, involves the reaction of a substituted benzoyl chloride with a formula XXVI thiocarboxamide in the presence of a trialkylamine and a solvent such as tetrahydrofuran, to obtain an N-substituted benzamide. This N-substituted amide is then heated to 25° to 110° C. with an excess of aqueous or aqueous alcohol sodium or potassium hydroxide to yield a formula XLIV substituted phenyl imidazolinethione. These reactions are similar to the initial reactions described above and illustrated in Flow Diagram IV. However, where it is desirable to provide an additional $C_1-C_3$ alkyl substituent on the substituted ring of the above-mentioned formula XLIV, imidazolinethione, said imidazolinethione may be dissolved in anhydrous tetrahydrofuran and treated with sec-butyl lithium, preferably dissolved in cyclohexane or other aromatic solvent. The addition of the sec-butyl lithium to the imidazolinethione is preferably conducted over an extended period of time, up to several hours, while maintaining the reaction mixture at a temperature between about −50° and −75° C. When addition is complete, the reaction mixture is permitted to warm to between about −30° and −50° C. and then admixed with a $C_1-C_3$ alkyl iodide dispersed in tetrahydrofuran. After stirring the reaction mixture is allowed to warm to ambient temperature and then the solvent is evaporated in vacuo to obtain the formula XLV multisubstituted product. Reaction is graphically illustrated in Flow Diagram IV, using methyl iodide and sec-butyl lithium for illustration.

Where it is desirable to provide a halogen substituent on the aromatic ring of the formula XLIV substituted imidazolinethione, said substituted imidazolinethione is dissolved in an anhydrous non-protic solvent such as tetrahydrofuran and treated with sec-butyl lithium dissolved in cyclohexane. The addition is made over a period of from about 0.5 to 2.0 hours while maintaining the reaction mixture at a temperature below about −50° C. The mixture is then warmed to a temperature between about −30° and −40° C. and halogenated with a halogenating agent such as hexachloroethane or the like, preferably dispersed in an anhydrous non-protic solvent such as tetrahydrofuran. The mixture is then permitted to warm to ambient temperature treated with iced saturated brine and then acidified to pH 3 with a strong mineral acid. Thereafter, the formula XLVI halogenated product is extracted from the reaction mixture with an organic solvent such as ether. This formula XLVI halogenated imidazolinethione is then readily converted to the corresponding formula XLVII, substituted 2-(5-thioxo-2-imidazolin-2-yl)benzoic acid by reaction of said halogenated imidazolinethione with sec-butyl lithium in the presence of tetrahydrofuran and tetramethylenediamine under a blanket of nitrogen, followed by admixture of the thus-prepared reaction mixture with anhydrous tetrahydrofuran, saturated with carbon dioxide. The formula XLVII product may be recovered from the reaction mixture by dispersing said mixture in water and acidifying the same with a strong mineral acid. The organic phase is then separated from the mixture and extracted with base. The aqueous phase is separated and acidified with mineral acid to yield the desired product. These reactions are illustrated in Flow Diagram IV below.

FLOW DIAGRAM IV

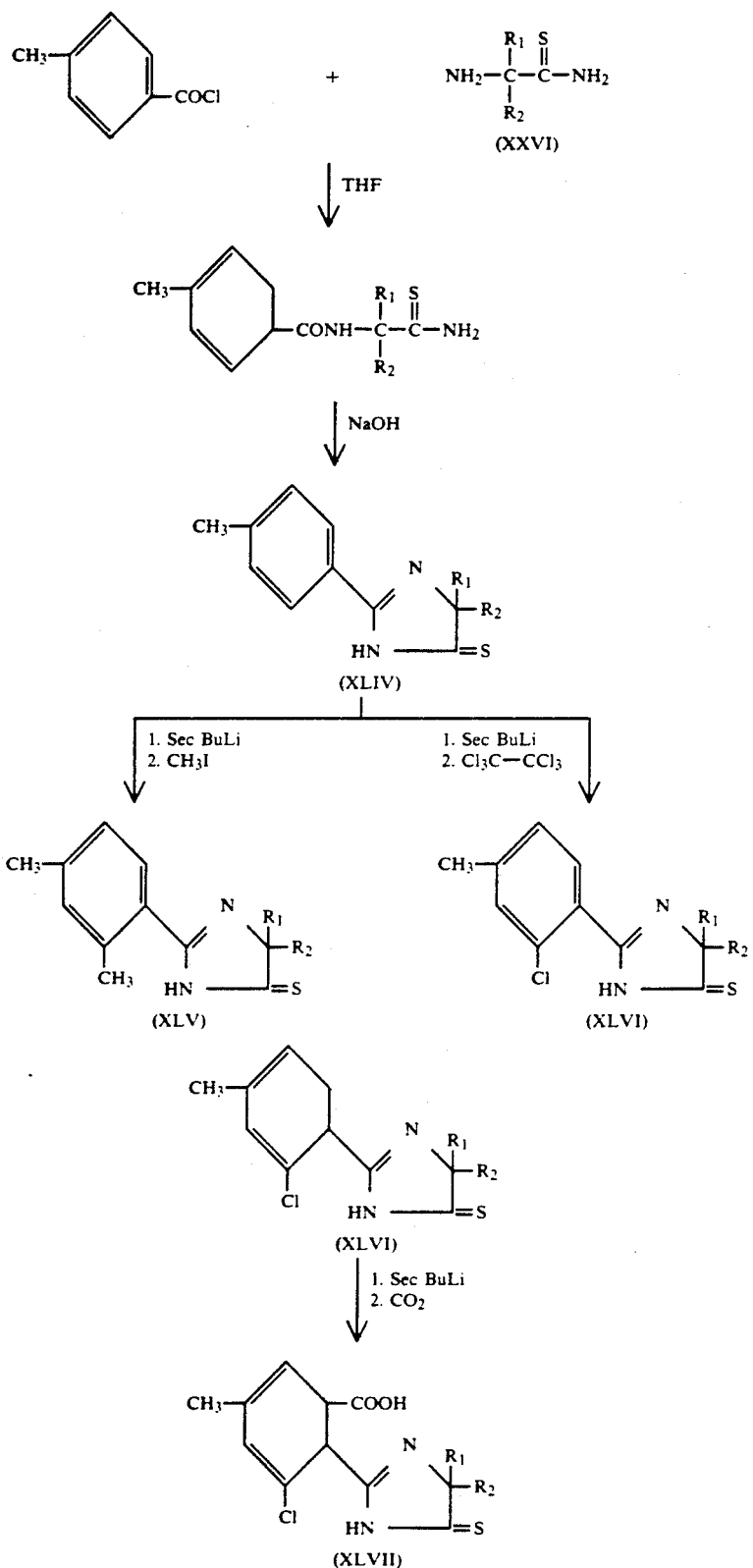

Another alternate route to the preparation of substituted (5-thioxo-2-imidazolin-2-yl)benzoic acids, esters and salts is graphically illustrated in Flow Diagram VI below. From this flow sheet, it can be seen that a substituted benzoyl chloride is treated with about 3 to 5 equivalents of a di-$C_1$-$C_3$alkylamine, such as diethylamine in tetrahydrofuran to yield the corresponding substituted benzamide. This substituted benzamide may then be halogenated, if desired, after treatment thereof with sec-butyl lithium in the presence of tetrahydrofuran or other similar solvent. The sec-butyl lithium is generally dissolved in cyclohexane and added to the benzamide containing reaction mixture while maintaining the temperature thereof below −50° C., e.g. −50° to −75° C. When addition is complete, the mixture is warmed to −30° to −40° C. and a halogenating agent, such as hexachloroethane, dispersed in a non-protic solvent added thereto. This yields the halogenated derivative of the substituted benzamide which is readily converted to the corresponding substituted phthalamic acid by reaction with sec-butyl lithium in tetrahydrofuran and tetramethylenediamine under a blanket of nitrogen, followed by admixture of the thus-prepared composition with tetrahydrofuran saturated with carbon dioxide. Reaction of the thus-formed substituted phthalamic acid, with ethyl chloroformate followed by triethylamine and a solution of a formula XXVI thiocarboxamide in anhydrous tetrahydrofuran, yields the substituted N,N-diethylphthalamide which undergoes base cyclization when heated to 25° to 110° C., with aqueous or aqueous alcoholic sodium or potassium hydroxide. The reaction provides a substituted N,N-dialkyl-(5-thioxo-2-imidazolin-2-yl)benzamide which is readily converted to the corresponding acid by treatment with strong mineral acid or to the corresponding ester by transesterification with a $C_1$-$C_3$ alcohol, such as methanol and a strong mineral acid, as shown in Flow Diagram VI. The thus-prepared ester may then be heated with an alkali metal hydroxide and acidified with strong mineral acid to provide the substituted (5-thioxo-2-imidazolin-2-yl)benzoic acid. These reactions are illustrated in Flow Diagram V below, where it can be seen that the final steps of this synthesis route are similar to the latter stages of the preparations illustrated in Flow Diagram III, although the early stages of the systems differ. It should also be noted that this reaction sequence results in the formation of an isomer of the compound prepared by Flow Diagram IV.

FLOW DIAGRAM V

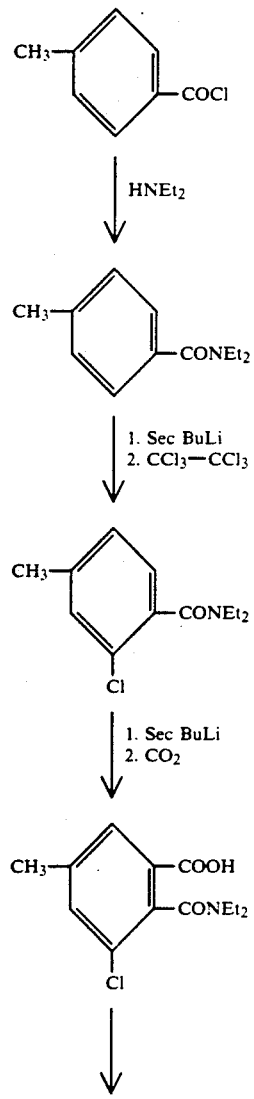

FLOW DIAGRAM V -continued

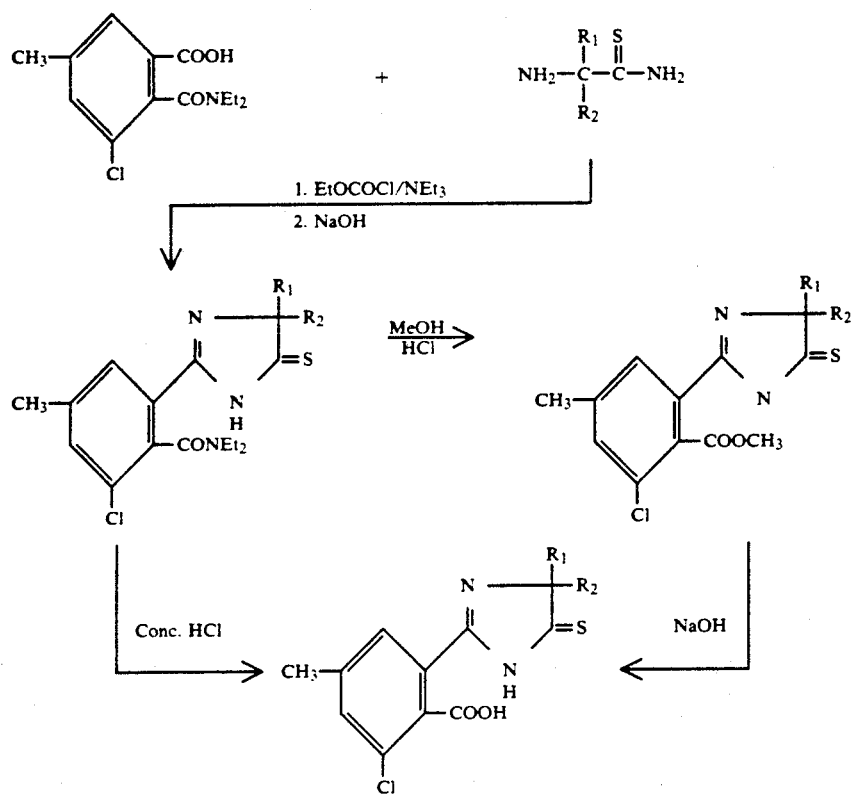

While herbicidal selectivity of the substituted and unsubstituted 5-thioxo-2-imidazolinyl benzoic acids, esters and salts, the thioimidazoisoindolediones, and the dihydrothioimidazoisoindolediones of this invention may vary with compound structure from crop to crop, the compounds of the invention all appear to show some selectivity in graminaceous crops, particularly of the small grain variety, such as rice, barley, wheat, oats or rye. This selection thus permits application of the active compounds to newly planted fields or to maturing crops for control of undesirable grasses and broadleaf weeds in the presence of said crops.

It is also surprising to find that the compounds of this invention frequently exhibit beneficial plant growth regulating (PGR) activity when employed at non-herbicidal rates of application. Effective PGR rates will of course, vary from compound to compound and crop to crop, depending on the time of application, weather and soil conditions, foliage density or the like.

When applied to cereal crops such as rice, wheat and barley, it is not uncommon to find that the treated plants are less suseptible to lodging due to adverse whether conditions, show increased tillering and frequently demonstrate increased crop yield.

In practice, the substituted or unsubstituted 5-thioxo-2-imidazolinyl benzoic acids, esters and salts, the thioimidazoisoindolediones, and the dihydrothioimidazoisoindolediones, may be applied to the foliage of undesirable monocotyledonous or dicotyledonous plants or to soil containing seeds or other propagating organs of said plants such as tubers, rhizomes or stolons, at ranges generally between about 0.032 and 4.0 kg/ha, and preferably between about 0.063 and 2.0 kg/ha, to control said undesirable plant species. These compounds may also be applied at rates as high as 8.0 kg/ha if desired.

In practice, the active compounds of the present invention may be applied to the foliage of plants or to soil containing seeds or other propagating organs thereof, in the form of a liquid spray, as a ULV concentrate or as a solid formulation.

When the above-said compounds are prepared as alkali metal or organoammonium salts, said salts are frequently found to be water soluble and can simply be dispersed in water, with or without the addition of a surfactant, and applied as an aqueous spray. Said compounds may also be prepared as wettable powders, flowable concentrates, emulsifiable concentrates, granular formulations or the like.

A typical emulsifiable concentrate can be prepared by dissolving about 5 to 25% by weight of the active ingredient in about 65 to 90% by weight of N-methylpyrrolidone, isophorone, butyl cellosolve, methylacetate or the like and dispersing therein about 5 to 10% by weight of a nonionic surfactant such as an alkylphenoxy polyethoxy alcohol. This concentrate is dispersed in water for application as a liquid spray or it may be applied directly as an ultra low volume (ULV) concentrate in the form of discrete droplets having a mass median diameter between about 17 and 150 microns particle size.

Wettable powders can be prepared by grinding together about 20 to 45% by weight of a finely divided carrier such as kaolin, bentonite, diatomaceous earth, attapulgite, or the like, 45 to 80% by weight of the active compound, 2 to 5% by weight of a dispersing agent such as sodium lignosulfonate, and 2 to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

When the compounds of the invention are to be used as herbicides where soil treatments are involved, the compounds may be prepared and applied as granular products. Preparation of the granular product can be achieved by dissolving the active compound in a solvent such as methylene chloride, N-methylpyrrolidone or the like and spraying the thus-prepared solution on a granular carrier such as corncob grits, sand, attapulgite, kaolin or the like.

The granular product thus-prepared generally comprises about 3 to 20% by weight of the active ingredient and about 97 to 80% by weight of the granular carrier.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE 1

Preparation of
N-[1,2-dimethyl-1-(thiocarbamoyl)propyl]-m-toluamide

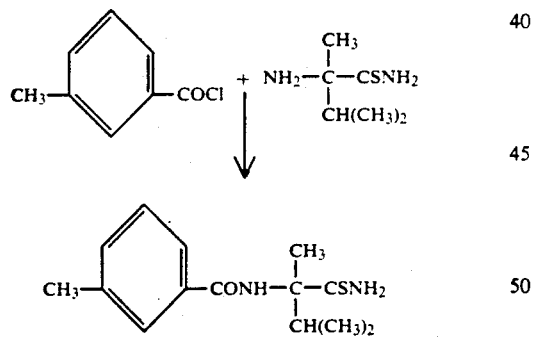

To a stirred solution containing 5 g 2-amino2,3-dimethylthiobutylamide and 9.53 mL triethylamine in 50 mL dry THF at −68° C. under nitrogen is added dropwise 4.52 mL m-toluoyl chloride. After stirring at −68° to −50° C. for one hour, the mixture is allowed to stir at room temperature overnight. The mixture is poured in 200 mL ice water and the product extracted into methylene chloride. The extract is washed with brine, dried and concentrated to give a yellow oil. Chromatography of this oil on silica gel using 80% hexane-ethyl acetate as eluant gives an analytically pure sample of N-[1,2-dimethyl-1-(thiocarbamoyl)propyl]-m-toluamide, mp 108°–110° C.

EXAMPLE 2

Preparation of
4-isopropyl-4-methyl-2-m-tolyl-2-imidazolin-5-thione

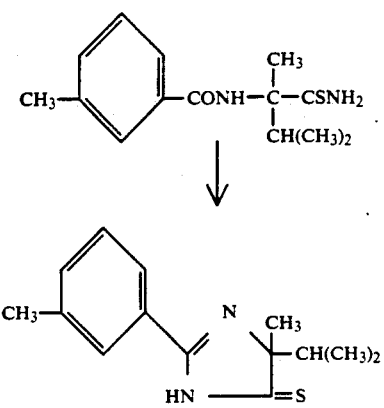

A solution containing 4.7 g N-[1,2-dimethyl-1-(thiocarbamoyl)propyl]-m-toluamide in 75 mL THF and 35 mL 10% NaOH is heated at 65° C. for 18 hours. The THF is removed in vacuo and the pH of the cooled residue adjusted to 3 with concentrated $H_2SO_4$. The product is extracted into $CH_2Cl_2$, the extract washed with brine, dried and concentrated to give a yellow solid. This is recrystallized from acetonitrile to give analytically pure 4-isopropyl-4-methyl-2-m-tolyl-2-imidazolin-5-thione, mp 122°–123° C.

EXAMPLE 3

Preparation of
2-(4-isopropyl-4-methyl-5-thioxo-2-imidazolin-2-yl)-p-toluic acid

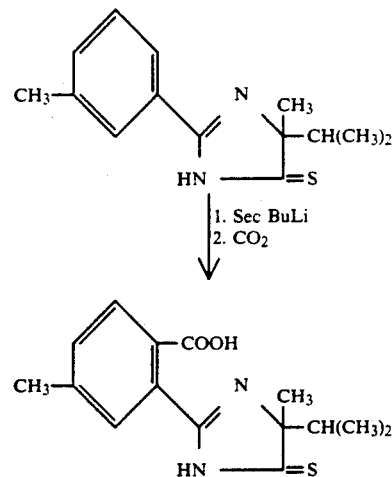

A stirred solution of 1.57 g 4-isopropyl-4-methyl-2-m-tolyl-2-imidazolin-5-thione in 15 mL THF containing 2.1 mL tetramethylenediamine under nitrogen is cooled to −68° C. and 16.4 mL of a 0.85 mL solution of butyl lithium in hexane added dropwise. The mixture is stirred at −60 to −40° C. for two hours and 30 minutes after which is added to 50 mL THF saturated with $CO_2$ at −60° C. Stirring is continued overnight at room temperature. The solution is poured into 100 mL ice water, the pH adjusted to 3 with concentrated $H_2SO_4$, and extracted with ethyl acetate. The extract is concentrated to give 0.85 g yellow crystalline solid.

This solid is dissolved in 15 mL ethyl acetate which is extracted with 15 mL 0.5 N NaOH. The aqueous phase is separated, acidified to pH 3 with concentrated H$_2$SO$_4$ and the resulting solid removed by filtration, washed and dried to give 2-(4-isopropyl-4-methyl-5-thioxo-2-imidazolin-2-yl)-p-toluic acid, mp 163°–170° C. (dec).

EXAMPLE 4

Preparation of 3-fluoro-2-(4-isopropyl-4-methyl-5-thioxo-2-imidazolin-2-yl)benzoic acid and the solids removed by filtration. This solid is a mixture of the two intermediate amides.

A solution containing 8.0 g amide in 67 mL 5% NaOH solution is heated at 80° C. for two hours and 30 minutes. After cooling, the solution to 5° C., it is acidified with concentrated H$_2$SO$_4$ and the resulting precipitate extracted into ethyl acetate. The organic phase is separated, dried and concentrated to give a 7.4 g bright yellow solid, mp 202°–212° C. (dec). The solid is boiled in 125 mL ether, the remaining pale yellow solid removed by filtration and dried. This is analytically pure 3-fluoro-2-(4-isopropyl-4-methyl-5-thioxo-2-imidazolin-2-yl)benzoic acid, mp 220°–222° C. (dec).

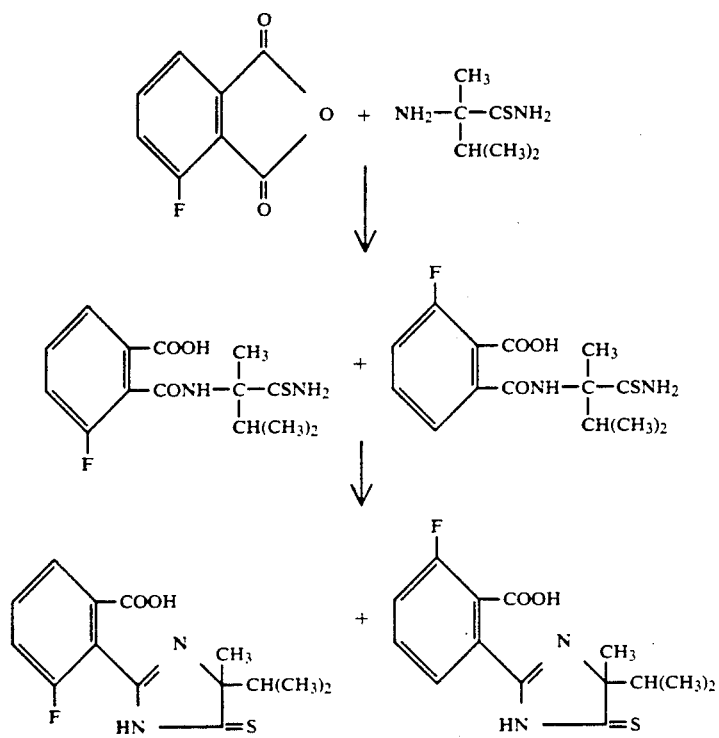

To a solution containing 5.47 g 3-fluorophthalic anhydride in 200 mL acetonitrile is added 4.82 g 2-amino-2,3-dimethylthiobutyramide and the mixture heated under reflux for 16 hours. The mixture is cooled to 5° C.

EXAMPLE 5

Preparation of o-(4-isopropyl-4-methyl-5-thioxo-2-imidazolin-2-yl)benzoic acid

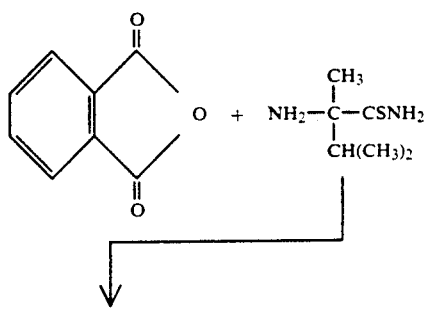

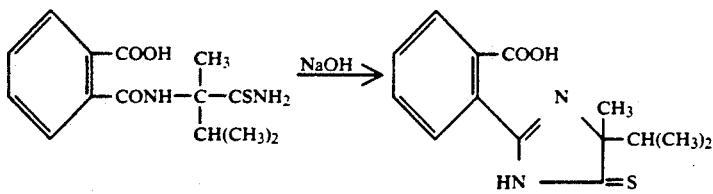

A mixture of 5.92 g (0.04 mol) phthalic anhydride and 5.85 g (0.04 mol) 2-amino-2,3-dimethylthiobutyramide in 200 mL methylene chloride is heated under reflux for 16 hours. The cooled solution is extracted with 100 mL 2N NaOH and the aqueous extract heated at 80° C. for three hours. The solution is cooled, acidified with concentrated sulfuric acid and filtered to remove the precipitate which is dried in vacuo to give 11.1 g of a mixture of phthalic acid and the desired product.

The solid is boiled in 300 mL acetonitrile, the mixture filtered and the filtrate cooled to give the desired product as pale yellow crystals, mp 192°-198° C. More material can be isolated in the filtrate. Recrystallization of a sample from acetonitrile gives analytically pure o-(4-isopropyl-4-methyl-5-thioxo-2-imidazolin-2-yl)benzoic acid, mp 204-206° C. as fine yellow crystals.

EXAMPLE 6

Preparation of 2-isopropyl-2-methyl-3-thio-5H-imidazo-[2,1-a]isoindole-3(2H),5-dione

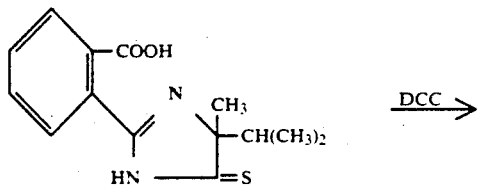

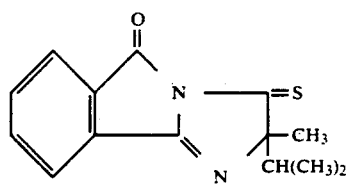

To a stirred solution containing 13 g of o-(4-isopropyl-4-methyl-5-thioxo-2-imidazolin-2-yl) -benzoic acid in 350 mL dry tetrahydrofuran under nitrogen is added 9.71 g dicyclohexylcarbodiimide. After stirring overnight at room temperature, the mixture is filtered and the filtrate concentrated under reduced pressure to give a yellow solid. A sample is chromatographed on silica gel in 5% CH₃CN—CH₂Cl₂ to give an analytically pure sample of 2-isopropyl-2-methyl-3-thio-5H-imidazo[2,1-a]isoindole-3(2H),5-dione, mp 139°-141° C.

Utilizing the above procedure, but substituting the appropriate acid for o-(4-isopropyl-4-methyl-5-thioxo-2-imidazolin-2-yl)benzoic acid, there are obtained the following compounds.

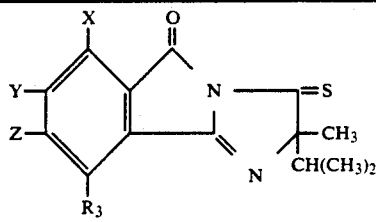

| X | Y | Z | R₃ | mp °C. |
|---|---|---|----|--------|
| H | H | H | H | 136.0–138.0 R-isomer |
| A | H | CH₃ | H | 143.0–150.0 |
| H | CH₃ | H | H | 139.0–140.0 |
| H | H | H | F | 109.0–112.0 |
| H | OCH₃ | H | H | 172.0–174.0 |
| CH₃ | H | CH₃ | H | 132.0–133.0 |
| H | —(CH₂)₂— | | H | 178.0–180.0 |
| H | SCH₃ | H | H | 180.0–184.0 |
| H | CH₂F | H | H | |
| H | H | CH₂F | H | |

EXAMPLE 7

Preparation of methyl o-(4-isopropyl-4-methyl-5-thioxo-2-imidazolin-2-yl)benzoate

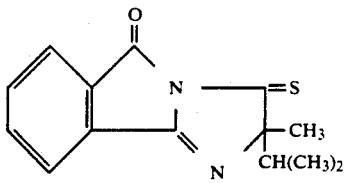

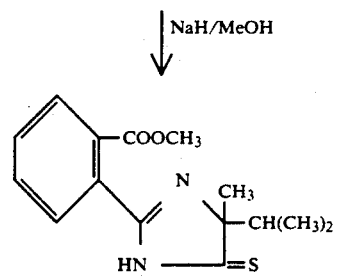

To a stirred solution containing 47 g 2-isopropyl-2-methyl-3-thio-5H-imidazo[2,1-a]isoindole-3(2H),-5-dione in 1680 mL methanol under nitrogen is added 850 mg sodium hydride. The mixture is stirred at room temperature overnight. The mixture is concentrated in vacuo and the residue crystallized from methanol to give methyl o-(4-methyl-5-thioxo-2-imidazolin-2-yl)benzoate mp 134°-138° C.

EXAMPLE 8

Preparation of methyl o-(4-isopropyl-4-methyl-5-thioxo-2-imidazolin-2-yl)benzoate hydrochloride

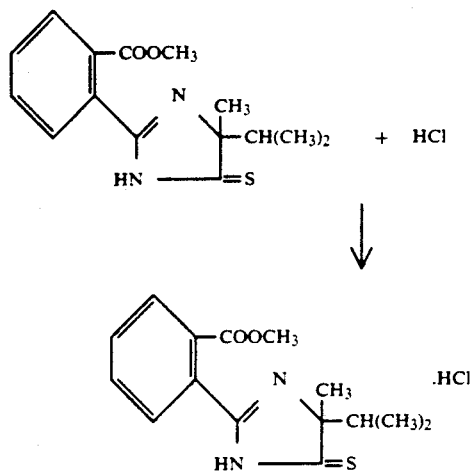

To a stirred solution containing 3 g methyl o-4-methyl-5-thioxo-2-imidazolin-2-yl)-benzoate in 120 mL ether is added 0.867 mL concentrated HCl. After two hours, the precipitate was removed by filtration and dried under vacuum at 50° C. overnight. This material is analytically pure and has mp 195°-198° C. (dec).

EXAMPLE 9

Preparation of 3-isopropyl-3-methyl-2-thio-5H-imidazo[2,1-a]isoindole-2(3H),5-dione

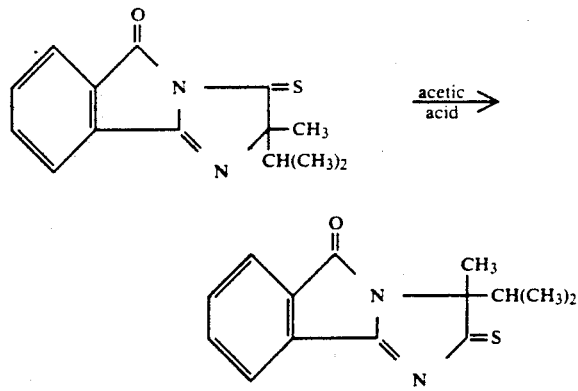

A solution containing 1 g 2-isopropyl-2-methyl-3-thio-5H-imidazo[2,1-a]isoindole-3(2H),5-dione in 10 mL glacial acetic acid is heated under reflux for two hours and 30 minutes. The solvent is then removed in vacuo, toluene added to the residue and then removed in vacuo. The residue is chromatographed on silia gel and the 2,5-dione eluted first using hexane and mixtures of hexane and ethyl acetate. The analytically pure 2,5-dione had mp 152°-158° C.

EXAMPLE 9-A

Preparation of 3-isopropyl-7-methoxy-3-methyl-2-thio-5H-imidazo[2,1-a]isoindole-2(3H),5-dione

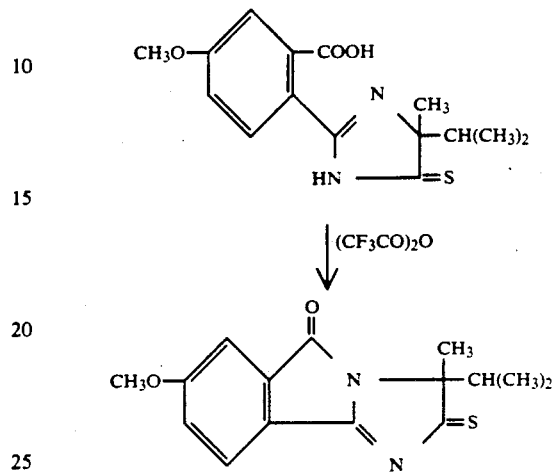

To a stirred solution containing 1.3 g acid in 150 mL dry THF at −65° C. is added during two hours a solution containing 2.4 ml trifluoroacetic anhydride in 100 mL dry THF. After a further 0.5 hours at −65° C., the solution is concentrated in vacuo, the residue dissolved in toluene and washed with water. The organic phase is dried and concentrated. The reddish solid solid is washed with pentane and dried to give analytically pure product mp 159°-161° C.

Using essentially the same procedure but substituting the appropriate 3,5-dione for 2-isopropyl-2-methyl-3-thio-5H-imidazo[2,1-a]isoindole-3(2H),5-dione in the above reaction yields the following substituted 2-thio-5H-imidazo[2,1-a]isoindole-2(3H),5-diones.

| X | Y | Z | R$_3$ | R$_1$ | R$_2$ | mp °C. |
|---|---|---|---|---|---|---|
| H | CH$_3$ | H | H | CH$_3$ | CH(CH$_3$)$_2$ | |
| H | H | CH$_3$ | H | CH$_3$ | CH(CH$_3$)$_2$ | |
| H | H | H | H | CH$_3$ | C$_2$H$_5$ | |
| H | H | H | H | CH$_3$ | CH$_3$ | |
| H | H | H | H | CH$_3$ | △ | |
| H | H | H | F | CH$_3$ | CH(CH$_3$)$_2$ | |
| H | H | H | OCH$_3$ | CH$_3$ | CH(CH$_3$)$_2$ | |
| CH$_3$ | H | H | CH$_3$ | CH$_3$ | CH(CH$_3$)$_2$ | |
| H | H | H | CH$_3$ | CH$_3$ | CH(CH$_3$)$_2$ | |
| CH$_3$ | H | CH$_3$ | H | CH$_3$ | CH(CH$_3$)$_2$ | 138.0-140.0 |
| H | —(CH$_2$)$_2$— | H | CH$_3$ | CH(CH$_3$)$_2$ | 183.0-184.0 |
| H | SCH$_3$ | H | H | CH$_3$ | CH(CH$_3$)$_2$ | 157.0-159.0 |

EXAMPLE 10

Preparation of 1,7,8,9bα and β-tetrahydro-3α-isopropyl-3-methyl-2-thio-5H-cyclobut[f]imidazo[2,1-a]isoindole-2(3H),5-dione

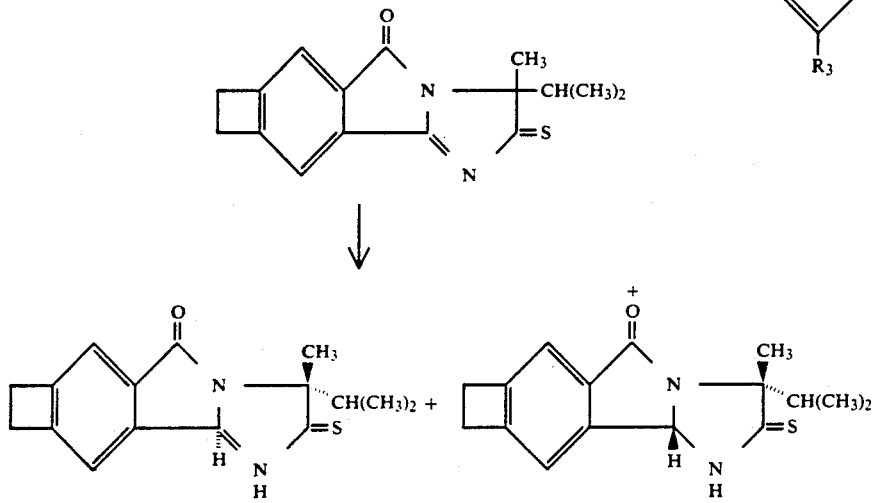

To a stirred solution containing 0.26 g sodium borohydride in 50 mL absolute ethanol at $-5°$ C. and under nitrogen is added dropwise 1.6 g dione in 50 mL THF. After stirring 16 hours at room temperature, the mixture is concentrated, the residue dissolved in 20 mL water and the pH adjusted to 1 with 6N HCl. The pH is then adjusted again to 4 with 10% NaOH and extracted with ethyl acetate. The combined extracts are washed with saturated sodium bicarbonate solution followed by brine, dried and concentrated to give a solid which is crystallized twice from $CH_2Cl_2$ to give the cis-product, mp 252°–258° C. The mother liquors are combined and filtered through a column of neutral alumina. Concentration of the eluent gives the pure trans-isomer, mp 212°–219° C.

Using essentially the same procedure as described above but substituting the appropriate imidazo [2,1-a]isoindole-2-(3H),5-dione for 7,8-dihydro-2-isopropyl-2-methyl-3-thio-5H-cyclobut[f]imidazo[2,1-a]isoindole-3(2H),5-dione, there is obtained the corresponding dihydro derivatives.

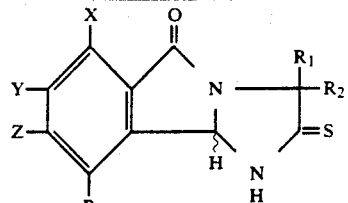

| $R_1$ | $R_2$ | X | Y | Z | $R_3$ | cis/trans | mp °C. |
|---|---|---|---|---|---|---|---|
| $CH_3$ | $CH(CH_3)_2$ | H | H | $OCH_3$ | H | trans | 231.0–234.0 |
| $CH_3$ | $CH(CH_3)_2$ | H | H | $OCH_3$ | H | cis | 198.0–201.0 |
| $CH_3$ | $CH(CH_3)_2$ | H | H | H | F | trans | 235.0–242.0 |
| $CH_3$ | $CH(CH_3)_2$ | H | H | H | H | trans | 195.0–196.0 |
| $CH_3$ | $CH(CH_3)_2$ | H | H | H | H | cis | 232.0–233.0 |
| $CH_3$ | $CH(CH_3)_2$ | H | $SCH_3$ | H | H | trans | |
| $CH_3$ | $C_2H_5$ | H | H | H | H | cis | |
| $CH_3$ | $C_2H_5$ | H | H | H | H | trans/cis | |
| $CH_3$ | $CH(CH_3)_2$ | H | H | $CH_3$ | H | trans/cis | |
| $CH_3$ | △ | H | H | H | H | trans/cis | |

EXAMPLE 10-A

Preparation of 1,9b-dihydro-3α-isopropyl-9bα-methoxy-3-methyl-2-thio-5H-imidazo[2,1-a]isoindole-2(3H),5-dione

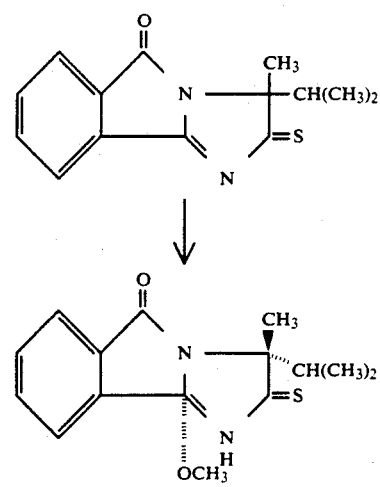

A solution containing 1 g freshly prepared dione is dissolved in 50 mL anhydrous methanol. After standing at room temperature for one hour, the mixture is concentrated and the residue recrystallized from acetonitrile to give analytically pure product, mp 158°–161° C.

Using essentially the same procedure but substituting the appropriate nucleophile for methanol, in an appropriate solvent such as THF, acetonitrile, and the appropriate dione for 3-isopropyl-3-methyl-2-thio-5H-imidazo[2,1-a]isoindole-2(3H),5-dione, the following are obtained.

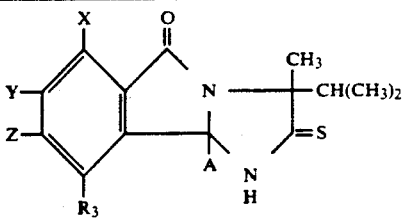

| X | Y | Z | R₃ | A |
|---|---|---|---|---|
| H | H | OCH₃ | H | OCH₃ |
| H | H | H | H | NH₂ |
| H | H | H | H | SCH₃ |
| H | H | H | H | OH |
| H | H | H | H | NHCH₃ |
| H | —(CH₂)₂— | | H | OCH₃ |
| CH₃ | H | CH₃ | H | OCH₃ |
| H | H | H | CH₂F | OCH₃ |
| H | SCH₃ | H | H | OCH₃ |
| H | H | H | H | OPr-n |

EXAMPLE 11

Preparation of N-(1-carbamoyl-1,2-dimethylpropyl)-p-thiotoluamide

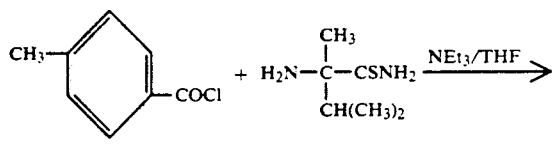

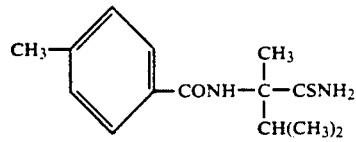

A stirred mixture containing 13.0 g (0.10 mol) of 2-amino-2,3-dimethylbutyramide and 15.3 mL (0.11 mol) of triethylamine in 150 mL of dry THF is treated dropwise at −70° C. with a solution of 15.5 g (0.10 mol) of p-toluoyl chloride in 25 mL dry THF. After being allowed to warm to ambient temperatures over a 16 hour period, the reaction mixture is treated with 50 mL water and stirred for one hour. The resulting three phases are filtered; the filtrate is separated and the aqueous phase is extracted with 150 mL ethyl acetate. All organic phases are combined, wasted with 100 mL of a saturated NaCl solution, dried over magnesium sulfate and concentrated in vacuo. A yellow solid residue is obtained. The nmr spectrum is consistent with the desired structure. This is purified by chromatography on silica gel using hexanes:ethyl acetate (70:30) as solvent. This yields the pure product mp 156°–157° C.

EXAMPLE 12

Preparation of 4-isopropyl-4-methyl-2-p-tolyl-2-imidazolin-5-thione

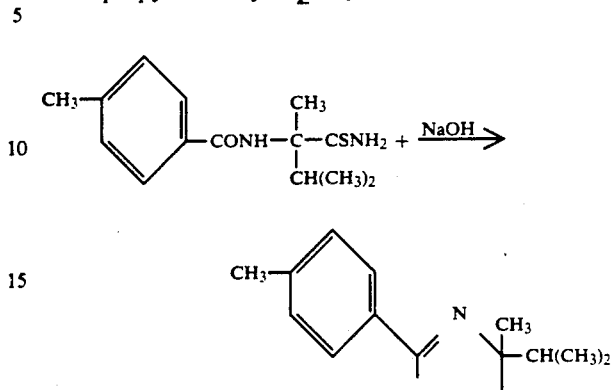

A mixture of 24.8 g (0.10 mol) of N-11-carbamoyl-1,2-dimethylpropyl)-p-toluamide in 263 mL of a 2.5N sodium hydroxide solution (0.50 mol NaOH) is heated with 100 mL p-dioxane and heated on a steam bath for 16 hours. The p-dioxane in removed in vacuo and the remaining aqueous solution is cooled to 5°–10° C. After carefully acidifying to pH 3–4 with concentrated sulfuric acid, the reaction mixture is extracted with a total of 750 mL methylene chloride. The organic phase is washed with 200 mL of a saturated sodium chloride solution, dried over magnesium sulfate and evaporated to dryness in vacuo to give a yellow solid residue. The nmr spectrum is consistent with the desired structure. This compound can be recrystallized from acetonitrile to give analytically pure 4-isopropyl-4-methyl-2-p-tolyl-2-imidazolin-5-thione mp 167°–170° C.

EXAMPLE 13

Preparation of 2-(2-chloro-p-tolyl)-4-isopropyl-4-methyl-2-imidazolin-5-thione

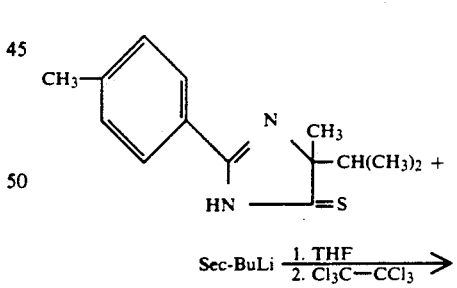

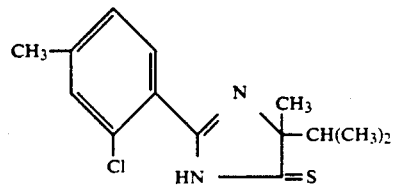

A mechanically stirred solution of 20.0 g of 4-isopropyl-4-methyl-2-p-tolyl-2-imidazolin-5-thione in 200 mL of dry tetrahydrofuran is treated dropwise with 160 mL of a 1.2M solution of sec-butyl lithium (0.191 mol) in cyclohexane over a 40 minute period at −72° to −65°

C. After stirring the resulting solution at −40° to −35° for one and one-half hours, a solution of 21.4 g (0.090 mol) of hexachloroethane in 125 mL of dry tetrahydrofuran is added dropwise. Addition temperature is allowed to reach −20° C. After warming to room temperature over a 16 hour period, the reaction is treated with 200 mL of ice water plus 200 mL of a saturated sodium chloride solution. The mixture is carefully acidified to pH 3 with concentrated sulfuric acid. The phases are separated and the aqueous phase is extracted with 200 mL ether. The organic phases are combined, dried over magnesium sulfate and concentrated to an oily residue. The residue is purified by chromatography on silica gel to give pure 2.(2-chloro-p- tolyl)-4-isopropyl-4-methyl-2-imidazolin-5-thione.

EXAMPLE 14

Preparation of 5-chloro-6-(4-isopropyl-4-methyl-5-thioxo-2-imidazolin-2-yl)-m-toluic acid

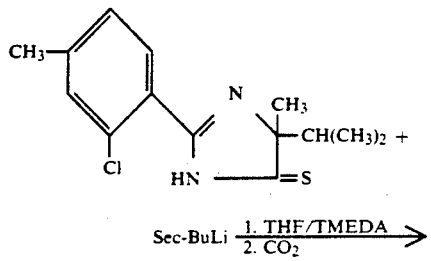

Sec-BuLi $\xrightarrow{\text{1. THF/TMEDA}}_{\text{2. CO}_2}$

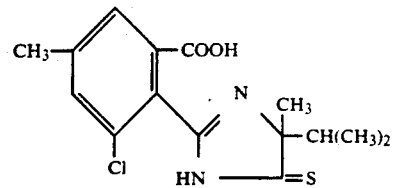

A stirred solution of 3.7 g of 2-(2-chloro-p-tolyl)-4-isopropyl-4-methyl-2-imidazolin- 5-thione in 70 mL anhydrous tetrahydrofuran and 4.7 mL (0.031 mol) of N,N,N',N'-tetramethylethylenediamine under $N_2$ is treated at −70° to −63° C. dropwise with 26 mL of a 1.2M solution of sec-butyl lithium (0.03 mol) in cyclohexane. After stirring for two hours at −55° to −45° C., the reaction is poured over 300 mL anhydrous THF saturated with carbon dioxide. The mixture is allowed to come to room temperature over a 6 hour period and then treated with 250 mL water and carefully acidified with ice cooling, to pH 3 with concentrated sulfuric acid. The phases are separated; the aqueous phase is extracted with 150 mL of ethyl acetate. The organic phases are combined and extracted with 50 mL of an 0.5N solution of sodium hydroxide. The basic aqeuous phase is cooled to 5°-10° C. and carefully acidified to pH 3 with concentrated sulfuric acid and the product extracted into methylene chloride. This is recrystallized to give pure 5-chloro-6-(4-isopropyl-4-methyl-5-thioxo-2-imidazolin-2-yl)-m-toluic acid.

EXAMPLE 15

Preparation of acids and esters

The procedures described in the above Examples are effective for preparing a wide variety of substituted and unsubstituted 5-thioxo-2-(2-imidazolin-2-yl)benzoic acids and esters. Among the 5-thioxo-2-(2-imidazolin-2-yl)benzoic acids and esters prepared by the procedures described above are those listed in Table I.

TABLE I

Compounds prepared by the procedures described in Examples 1-19 having the structure:

| R | $R_1$ | $R_2$ | X | Y | Z | $R_3$ | mp °C. | |
|---|---|---|---|---|---|---|---|---|
| $CH_3$ | $CH_3$ | $CH(CH_3)_2$ | $NO_2$ | H | H | $(NO_2)$ | — | IM* |
| H | $CH_3$ | $CH(CH_3)_2$ | H | H | H | F | 220-222 | |
| $CH_3$ | $CH_3$ | $CH(CH_3)_2$ | F | H | H | (F) | — | IM |
| H | $CH_3$ | $CH(CH_3)_2$ | H | H | $NO_2$ | H | — | |
| $CH_3$ | $CH_3$ | $CH(CH_3)_2$ | $NO_2$ | H | H | H | — | |
| $CH_3$ | $CH_3$ | $CH(CH_3)_2$ | H | H | $NO_2$ | H | — | |
| $CH_3$ | $CH_3$ | $CH(CH_3)_2$ | H | H | $CH_3$ | Cl | | |
| $CH_3$ | $CH_3$ | $CH(CH_3)_2$ | $CH_3$ | H | H | $CH_3$ | | |
| H | $CH_3$ | $CH(CH_3)_2$ | $CH_3$ | —CH=$CH_2$—CH=$CH_2$— | | H | | |
| H | $CH_3$ | $CH(CH_3)_2$ | $CH_3$ | H | $CH_3$ | Cl | | |
| H | $CH_3$ | $CH(CH_3)_2$ | H | H | H | H | 204-206 | |
| $CH_3$ | $CH_3$ | $CH(CH_3)_2$ | H | H | H | H | 134-138 | |
| $CH_3$ | $CH_3$ | $CH(CH_3)_2$ | H | H | H | F | 164-172 | |
| H | $CH_3$ | $CH(CH_3)_2$ | H | H | H | H | 172-175 | (R) |
| $CH_3$ | $CH_3$ | $CH(CH_3)_2$ | H | H | H | H | 161-163 | (R) |
| $CH_2C_6H_5$ | $CH_3$ | $CH(CH_3)_2$ | H | H | H | H | 142-144 | |

TABLE I-continued

Compounds prepared by the procedures described in Examples 1-19 having the structure:

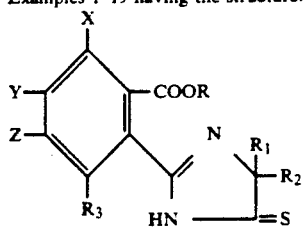

| R | $R_1$ | $R_2$ | X | Y | Z | $R_3$ | mp °C. | |
|---|---|---|---|---|---|---|---|---|
| $\overset{+}{NH_3}-CH(CH_3)_2$ | $CH_3$ | $CH(CH_3)_2$ | H | H | H | H | | |
| $(CH_3)_3\overset{+}{N}-C_6H_5$ | $CH_3$ | $CH(CH_3)_2$ | H | H | H | H | | |
| $CH_3$ | $CH_3$ | $CH(CH_3)_2$ | H | $CH_3$ | H | H | 178-181 | |
| H | $CH_3$ | $CH(CH_3)_2$ | H | H | $CH_3$ | H | 163-172 | |
| $CH_3$ | $CH_3$ | $CH(CH_3)_2$ | H | $CH_3$ | $(CH_3)$ | H | 149-160 | IM |
| H | $CH_3$ | $CH(CH_3)_2$ | H | $CH_3$ | $(CH_3)$ | H | 105-123 | IM |
| $CH_3$ | $CH_3$ | $CH(CH_3)_2$ | H | $CH_3$ | H | H | 188-191 | |
| H | $CH_3$ | $CH(CH_3)_2$ | H | $CH_3$ | H | H | 133-141 | |
| H | $CH_3$ | $CH(CH_3)_2$ | H | H | H | $OCH_3$ | | |
| $CH_3$ | $CH_3$ | $CH(CH_3)_2$ | H | H | H | $OCH_3$ | | |
| H | $CH_3$ | $C_2H_5$ | H | H | H | H | | |
| H | $CH_3$ | $CH_3$ | H | H | H | H | | |
| $CH_3$ | $CH_3$ | $CH(CH_3)_2$ | H | $OCF_3$ | H | H | 158-159 | |
| $CH_3$ | $CH_3$ | $CH(CH_3)_2$ | $SCH_3$ | H | H | H | 100-104 | |
| H | $CH_3$ | $CH(CH_3)_2$ | $SCH_3$ | H | H | H | 103-113 | |
| $OCH_2C{\equiv}CH$ | $CH_3$ | $CH(CH_3)_2$ | H | H | H | H | 148-150 | |
| $C_2H_5$ | $CH_3$ | $CH(CH_3)_2$ | H | H | H | H | 132.5-134 | |
| $-CH_2-\text{(furyl)}$ | $CH_3$ | $CH(CH_3)_2$ | H | H | H | H | 150-152 | |
| $CH_3$ | $CH_3$ | $CH(CH_3)_2$ | H | H | H | H | 195-198 (dec) HCl salt | |
| $CH(CH_3)_2$ | $CH_3$ | $CH(CH_3)_2$ | H | H | H | H | 127-129 | |
| $Na^+$ | $CH_3$ | $CH(CH_3)_2$ | H | H | H | H | 175-200 (dec) | |
| $Ca^{++}/2$ | $CH_3$ | $CH(CH_3)_2$ | H | H | H | H | >285 | |
| H | $CH_3$ | $CH(CH_3)_2$ | H | H | $C_2H_5$ | H | | |
| H | $CH_3$ | $CH(CH_3)_2$ | H | $C_2H_5$ | H | H | | |
| H | $CH_3$ | $CH(CH_3)_2$ | $CH_3$ | H | $CH_3$ | H | 191-193 | |
| H | $CH_3$ | $CH(CH_3)_2$ | H | $-(CH_2)_2-$ | | H | 187-192 | |
| $CH_3$ | $CH_3$ | $CH(CH_3)_2$ | $CH_3$ | H | $CH_3$ | H | 128-130 | |
| $CH_3$ | $CH_3$ | $CH(CH_3)_2$ | H | $OCH_3$ | H | H | 170-171.5 | |
| $CH_3$ | $CH_3$ | $CH(CH_3)_2$ | H | $-(CH_2)_2-$ | | H | 199-201 | |
| H | $CH_3$ | $CH(CH_3)_2$ | H | $OCH_3$ | H | H | 124-126 | |
| $CH_3$ | $CH_3$ | $CH(CH_3)_2$ | H | $OCHF_2$ | $(OCHF_2)$ | H | 141-146 | IM |
| $CH_3$ | $CH_3$ | $CH(CH_3)_2$ | H | $SCH_3$ | H | H | 184-187 | |
| H | $CH_3$ | $CH(CH_3)_2$ | H | $SCH_3$ | H | H | 210-214 | |

*IM - indicates that the product is a mixture of isomers, the second being shown as ( ).

EXAMPLE 16

Postemergence herbicidal evaluation of test compounds

The postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures containing 0.5% TWEEN® 20, a polyoxyethylene sorbitan monolaurate surfactant of Atlas Chemical Industries, in sufficient quantities to provide the equivalent of about 0.063 to 4.0 kg per hectare of active compound when applied to the plants through a spray nozzle operating at 40 psig for a predetermined time. After spraying, the plants are placed on greenhouse benches and are cared for in the usual manner, commensurate with conventional greenhouse practices From four to five weeks after treatment, the seedling plants, are examined and rater according to the rating system provided below. The data obtained are recorded in Table II below.

| Rating System | % Difference in Growth from the Check |
|---|---|
| 0 - No Effect | 0 |
| 1 - Possible effect | 1-10 |
| 2 - Slight effect | 11-25 |
| 3 - Moderate effect | 26-40 |
| 5 - Definite injury | 41-60 |
| 6 - Herbicidal effect | 61-75 |
| 7 - Good herbicidal effect | 76-90 |
| 8 - Approaching complete kill | 91-99 |
| 9 - Complete kill | 100 |
| 4 - Abnormal growth, that is, a definite physiological mal- | |

-continued

| Rating System | % Difference in Growth from the Check |
|---|---|
| formation but with an overall effect less than a 5 on the rating scale. | |

In most cases the data are for a single test, but in several instances, they are average values obtained from more than one test.

| Plant Species Used | |
|---|---|
| Barnyardgrass | (*Echinochloa crusgalli*) |
| Purple Nutsedge | (*Cyperus rotundus* L.) |
| Wild Oats | (*Avena fatua*) |
| Quackgrass | (*Agropyron repens*) |
| Field Bindweed | (*Convolvulus arvensis* L.) |
| Morningglory | (*Ipomoea purpurea*) |
| Velvetleaf | (*Abutilon theophrasti*) |
| Barley | (*Hordeum vulgare*) |
| Corn | (*Zea mays*) |
| Soybean | (*Glycine max*) |
| Wheat | (*Triticum aestivum*) |

TABLE II

POST-EMERGENCE TESTS - RATES IN KG/HA

| Compound | RATE | BARN YARDGR | P NUT SEDGE | WILD OATS | QUACK GRASS | FLD BINDWD | MRNGLRY SP | VELVET LEAF | S BARLEY LA | CORN FIELD | SOYBEAN WI | S WHEAT ER |
|---|---|---|---|---|---|---|---|---|---|---|---|---|
| o-(4-Isopropyl-4-methyl-5-thioxo-2-imidazolin-2-yl)benzoic acid; | 2.000 | 9.0 | 8.0 | 9.0 | 8.0 | 9.0 | 8.0 | 8.0 | 8.0 | 9.0 | 8.0 | 8.0 |
|  | 1.000 | 9.0 | 7.5 | 9.0 | 8.0 | 9.0 | 8.0 | 8.5 | 6.0 | 8.5 | 8.0 | 8.0 |
|  | .500 | 9.0 | 6.5 | 9.0 | 6.5 | 7.5 | 6.5 | 7.5 | 5.5 | 8.5 | 8.0 | 8.0 |
|  | .250 | 5.0 | 4.5 | 5.5 | 7.5 | 7.5 | 5.5 | 4.0 | 4.5 | 7.5 | 7.5 | 7.5 |
|  | .125 | 2.5 | 4.0 | 3.5 | 4.0 | 5.0 | 4.5 | 2.5 | 2.0 | 6.0 | 7.0 | 7.0 |
|  | .063 | 1.0 | 2.0 | 0.5 | 2.0 | 2.5 | 2.5 | 1.0 | 1.0 | 2.5 | 6.0 | 6.0 |
|  | .032 | 0.0 | 2.0 | 0.0 | 0.0 | 3.0 | 3.0 | 0.0 | 0.0 | 2.0 | 5.0 | 5.0 |
| Methyl o-(4-isopropyl-4-methyl-5-thioxo-2-imidazolin-2-yl)benzoate; | 2.000 | 3.0 | 5.0 | 9.0 | 0.0 | 6.0 | 4.0 | 7.0 | 0.0 | 6.0 | 8.0 | 8.0 |
|  | 1.000 | 0.0 | 2.0 | 5.0 | 0.0 | 0.0 | 2.0 | 0.0 | 0.0 | 6.0 | 8.0 | 8.0 |
|  | .500 | 0.0 | 0.0 | 4.0 | 0.0 | 0.0 | 4.0 | 3.0 | 0.0 | 1.0 | 7.0 | 7.0 |
|  | .250 | 0.0 | 0.0 | 0.0 | 0.0 | 0.0 | 2.0 | 1.0 | 0.0 | 0.0 | 5.0 | 5.0 |
|  | .125 | 0.0 | 0.0 | 0.0 | 0.0 | 0.0 | 1.0 | 1.0 | 0.0 | 0.0 | 4.0 | 4.0 |
|  | .063 | 0.0 | 0.0 | 0.0 | 0.0 | 0.0 | 1.0 | 1.0 | 0.0 | 0.0 | 3.0 | 3.0 |
| 3-Fluoro-2-(4-isopropyl-4-methyl-5-thioxo-2-imidazolin-2-yl)benzoic acid; | 2.000 | 9.0 | 8.0 | 4.0 | 0.0 | 9.0 | 8.0 | 9.0 | 3.0 | 3.0 | 8.0 | 8.0 |
|  | 1.000 | 7.0 | 8.0 | 2.0 | 0.0 | 8.0 | 8.0 | 7.0 | 2.0 | 3.0 | 8.0 | 8.0 |
|  | .500 | 4.0 | 8.0 | 2.0 | 0.0 | 9.0 | 8.0 | 7.0 | 2.0 | 3.0 | 8.0 | 8.0 |
|  | .250 | 2.0 | 6.0 | 0.0 | 0.0 | 8.0 | 8.0 | 6.0 | 1.0 | 2.0 | 8.0 | 8.0 |
|  | .125 | 0.0 | 3.0 | 0.0 | 0.0 | 7.0 | 7.0 | 4.0 | 1.0 | 2.0 | 6.0 | 6.0 |
|  | .063 | 0.0 | 3.0 | 0.0 | 0.0 | 5.0 | 6.0 | 2.0 | 0.0 | 1.0 | 6.0 | 6.0 |
| (R)-(+)-o-(4-Isopropyl-4-methyl-5-thioxo-2-imidazolin-2-yl)benzoic acid; | 2.000 | 9.0 | 8.0 | 9.0 | 8.0 | 9.0 | 8.0 | 9.0 | 7.0 | 9.0 | 8.0 | 8.0 |
|  | 1.000 | 9.0 | 8.0 | 9.0 | 8.0 | 9.0 | 8.0 | 9.0 | 4.0 | 9.0 | 8.0 | 8.0 |
|  | .500 | 9.0 | 7.0 | 9.0 | 5.0 | 9.0 | 8.0 | 9.0 | 6.0 | 9.0 | 8.0 | 8.0 |
|  | .250 | 7.0 | 7.0 | 7.0 | 6.0 | 9.0 | 8.0 | 6.0 | 2.0 | 9.0 | 7.0 | 7.0 |
|  | .125 | 5.0 | 5.0 | 4.0 | 4.0 | 9.0 | 6.0 | 3.0 | 3.0 | 8.0 | 6.0 | 6.0 |
|  | .063 | 2.0 | 3.0 | 0.0 | 0.0 | 5.0 | 6.0 | 1.0 | 1.0 | 8.0 | 6.0 | 6.0 |
| (R)-(+)-Methyl o-(4-isopropyl-4-methyl-5-thioxo-2-imidazolin-2-yl)benzoate; | 2.000 | 8.0 | 7.0 | 7.0 | 0.0 | 6.0 | 8.0 | 8.0 | 4.0 | 7.0 | 8.0 | 8.0 |
|  | 1.000 | 5.0 | 7.0 | 6.0 | 0.0 | 5.0 | 6.0 | 7.0 | 1.0 | 8.0 | 8.0 | 8.0 |
|  | .500 | 3.0 | 6.0 | 4.0 | 0.0 | 9.0 | 6.0 | 7.0 | 2.0 | 8.0 | 7.0 | 7.0 |
|  | .250 | 1.0 | 2.0 | 4.0 | 0.0 | 2.0 | 4.0 | 4.0 | 1.0 | 8.0 | 7.0 | 7.0 |
|  | .125 | 0.0 | 0.0 | 2.0 | 0.0 | 0.0 | 2.0 | 0.0 | 0.0 | 7.0 | 6.0 | 6.0 |
|  | .063 | 0.0 | 0.0 | 0.0 | 0.0 | 0.0 | 0.0 | 0.0 | 0.0 | 5.0 | 5.0 | 5.0 |
| Benzyl o-(4-isopropyl-4-methyl-5-thioxo-2-imidazolin-2-yl)benzoate; | 2.000 | 9.0 | 8.0 | 9.0 | 0.0 | 9.0 | 7.0 | 5.0 | 3.0 | 2.0 | 4.0 | 4.0 |
|  | 1.000 | 7.0 | 8.0 | 8.0 | 0.0 | 8.0 | 6.0 | 3.0 | 3.0 | 1.0 | 3.0 | 3.0 |
|  | .500 | 6.0 | 8.0 | 6.0 | 0.0 | 7.0 | 4.0 | 3.0 | 2.0 | 0.0 | 3.0 | 3.0 |
| Isopropylammonium o-(4-isopropyl-4-methyl-5-thioxo-2-imidazolin-2-yl)benzoic acid; | 2.000 | 9.0 | 8.0 | 9.0 | 8.0 | 9.0 | 8.0 | 9.0 | 9.0 | 9.0 | 8.0 | 8.0 |
|  | 1.000 | 9.0 | 8.0 | 9.0 | 7.0 | 9.0 | 9.0 | 9.0 | 7.0 | 9.0 | 8.0 | 8.0 |
|  | .500 | 7.0 | 8.0 | 7.0 | 6.0 | 8.0 | 7.0 | 9.0 | 7.0 | 9.0 | 8.0 | 8.0 |
|  | .250 | 6.0 | 6.0 | 6.0 | 2.0 | 9.0 | 8.0 | 9.0 | 5.0 | 7.0 | 6.0 | 6.0 |
|  | .125 | 2.0 | 3.0 | 4.0 | 0.0 | 6.0 | 5.0 | 4.0 | 2.0 | 7.0 | 5.0 | 5.0 |
|  | .063 | 0.0 | 2.0 | 3.0 | 0.0 | 5.0 | 4.0 | 2.0 | 0.0 | 5.0 | 4.0 | 4.0 |
| Benzyltrimethylammonium o-(4-isopropyl-4-methyl-5-thioxo-2-imidazolin-2-yl)benzoic acid; | 2.000 | 9.0 | 8.0 | 8.0 | 7.0 | 9.0 | 8.0 | 9.0 | 6.0 | 9.0 | 8.0 | 8.0 |
|  | 1.000 | 7.0 | 8.0 | 8.0 | 6.0 | 8.0 | 6.0 | 9.0 | 5.0 | 9.0 | 8.0 | 8.0 |
|  | .500 | 6.0 | 8.0 | 6.0 | 3.0 | 7.0 | 6.0 | 7.0 | 3.0 | 9.0 | 7.0 | 7.0 |
|  | .250 | 3.0 | 4.0 | 4.0 | 0.0 | 5.0 | 6.0 | 5.0 | 3.0 | 7.0 | 7.0 | 7.0 |
|  | .125 | 2.0 | 3.0 | 0.0 | 0.0 | 4.0 | 2.0 | 2.0 | 2.0 | 7.0 | 6.0 | 6.0 |
|  | .063 | 0.0 | 2.0 | 0.0 | 0.0 | 3.0 | 2.0 | 0.0 | 2.0 | 4.0 | 5.0 | 5.0 |
| 2-Propynyl o-(4-isopropyl-4-methyl-5-thioxo-2-imidazolin-2-yl)benzoate; | 2.000 | 8.0 | 8.0 | 7.0 | 6.0 | 7.0 | 8.0 | 8.0 | 6.0 | 9.0 | 8.0 | 8.0 |
|  | 1.000 | 7.0 | 6.0 | 8.0 | 4.0 | 8.0 | 8.0 | 4.0 | 5.0 | 9.0 | 8.0 | 8.0 |
|  | .500 | 4.0 | 6.0 | 4.0 | 2.0 | 9.0 | 6.0 | 4.0 | 3.0 | 9.0 | 8.0 | 8.0 |
|  | .250 | 0.0 | 3.0 | 3.0 | 0.0 | 6.0 | 4.0 | 2.0 | 2.0 | 7.0 | 8.0 | 8.0 |

TABLE II-continued

POST-EMERGENCE TESTS - RATES IN KG/HA

| Compound | RATE | BARN YARDGR | P NUT SEDGE | WILD OATS | QUACK GRASS | FLD BINDWD | MRNGLRY SP | VELVET LEAF | S BARLEY LA | CORN FIELD | SOYBEAN WI | S WHEAT ER |
|---|---|---|---|---|---|---|---|---|---|---|---|---|
| Ethyl o-(4-isopropyl-4-methyl-5-thioxo-2-imidazolin-2-yl)benzoate; | .125 | 0.0 | 2.0 | 2.0 | 0.0 | 6.0 | 4.0 | 0.0 | 2.0 | 6.0 | 6.0 | |
| | .063 | 0.0 | 0.0 | 0.0 | 0.0 | 3.0 | 2.0 | 0.0 | 1.0 | 5.0 | 5.0 | |
| | 2.000 | 0.0 | 8.0 | 7.0 | 0.0 | 0.0 | 3.0 | 5.0 | 2.0 | 3.0 | 5.0 | |
| | 1.000 | 0.0 | 6.0 | 6.0 | 0.0 | 0.0 | 3.0 | 4.0 | 1.0 | 2.0 | 6.0 | |
| | .500 | 0.0 | 5.0 | 5.0 | 0.0 | 0.0 | 2.0 | 3.0 | 1.0 | 2.0 | 5.0 | |
| | .250 | 0.0 | 2.0 | 3.0 | 0.0 | 0.0 | 0.0 | 2.0 | 0.0 | 1.0 | 5.0 | |
| | .125 | 0.0 | 2.0 | 2.0 | 0.0 | 0.0 | 0.0 | 1.0 | 0.0 | 1.0 | 5.0 | |
| | .063 | 0.0 | 0.0 | 0.0 | 0.0 | 0.0 | 0.0 | 0.0 | 0.0 | 1.0 | 3.0 | |
| Furfuryl o-(4-isopropyl-4-methyl-5-thioxo-2-imidazolin-2-yl)-benzoate; | 2.000 | 8.0 | 8.0 | 6.0 | 3.0 | 8.0 | 8.0 | 8.0 | 4.0 | 9.0 | 7.0 | |
| | 1.000 | 8.0 | 7.0 | 6.0 | 2.0 | 8.0 | 7.0 | 6.0 | 3.0 | 7.0 | 7.0 | |
| | .500 | 5.0 | 7.0 | 3.0 | 1.0 | 8.0 | 7.0 | 5.0 | 3.0 | 7.0 | 6.0 | |
| | .250 | 2.0 | 2.0 | 2.0 | 0.0 | 4.0 | 5.0 | 3.0 | 2.0 | 5.0 | 5.0 | |
| | .125 | 0.0 | 0.0 | 0.0 | 0.0 | 0.0 | 0.0 | 1.0 | 1.0 | 2.0 | 4.0 | |
| | .063 | 0.0 | 0.0 | 0.0 | 0.0 | 0.0 | 0.0 | 0.0 | 0.0 | 1.0 | 3.0 | |
| Methyl o-(4-isopropyl-4-methyl-5-thioxo-2-imidazolin-2-yl)benzoate hydrochloride; | 2.000 | 5.0 | 7.0 | 7.0 | 0.0 | 5.0 | 6.0 | 6.0 | 3.0 | 8.0 | 7.0 | |
| | 1.000 | 2.0 | 6.0 | 6.0 | 0.0 | 2.0 | 4.0 | 4.0 | 2.0 | 8.0 | 7.0 | |
| | .500 | 0.0 | 6.0 | 6.0 | 0.0 | 1.0 | 3.0 | 3.0 | 2.0 | 8.0 | 7.0 | |
| | .250 | 0.0 | 3.0 | 3.0 | 0.0 | 0.0 | 2.0 | 2.0 | 2.0 | 4.0 | 7.0 | |
| | .125 | 0.0 | 0.0 | 2.0 | 0.0 | 0.0 | 0.0 | 0.0 | 0.0 | 4.0 | 5.0 | |
| | .063 | 0.0 | 0.0 | 0.0 | 0.0 | 0.0 | 0.0 | 0.0 | 0.0 | 2.0 | 4.0 | |
| Methyl 3-fluoro-2-(4-isopropyl-4-methyl-5-thioxo-2-imidazolin-2-yl)-benzoate. | 2.000 | 0.0 | 5.0 | 0.0 | 0.0 | 8.0 | 8.0 | 6.0 | 0.0 | 0.0 | 8.0 | |
| | 1.000 | 0.0 | 3.0 | 0.0 | | 6.0 | 7.0 | 3.0 | 0.0 | 0.0 | 8.0 | |
| | .500 | 0.0 | 2.0 | 0.0 | 0.0 | 6.0 | 6.0 | 2.0 | 0.0 | 0.0 | 8.0 | |
| | .250 | 0.0 | 0.0 | 0.0 | 0.0 | 4.0 | 5.0 | 0.0 | 0.0 | 0.0 | 7.0 | |
| | .125 | 0.0 | 0.0 | 0.0 | 0.0 | 3.0 | 3.0 | 0.0 | 0.0 | 0.0 | 6.0 | |
| | .063 | 0.0 | 0.0 | 0.0 | 0.0 | 2.0 | 2.0 | 0.0 | 0.0 | 0.0 | 6.0 | |

EXAMPLE 17

Preemergence herbicidal evaluation of test compounds

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.063 to 4.0 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system set forth above. The herbicidal proficiency of the active ingredients of the present invention is evident from the test results which are recorded in Table III below. Where more than one test is involved for a given compound, the data are averaged.

TABLE III

PRE-EMERGENCE TESTS - RATES IN KG/HA

| Compound | RATE | BARN YARDGR | P NUT SEDGE | WILD OATS | QUACK GRASS | FLD BINDWD | MRNGLRY SP | VELVET LEAF | S BARLEY LA | CORN FIELD | SOYBEAN WI |
|---|---|---|---|---|---|---|---|---|---|---|---|
| o-(4-Isopropyl-4-methyl-5-thioxo-2-imidazolin-2-yl)benzoic acid; | 2.000 | 9.0 | 9.0 | 9.0 | 9.0 | 9.0 | 8.0 | 9.0 | 9.0 | 9.0 | 8.0 |
| | 1.000 | 9.0 | 9.0 | 8.5 | 9.0 | 9.0 | 8.0 | 9.0 | 7.3 | 9.0 | 8.5 |
| | .500 | 7.0 | 9.0 | 5.5 | 9.0 | 9.0 | 8.0 | 8.5 | 6.0 | 8.5 | 8.5 |
| | .250 | 6.5 | 9.0 | 3.5 | 9.0 | 9.0 | 8.0 | 8.0 | 3.7 | 7.5 | 7.5 |
| | .125 | 4.5 | 9.0 | 2.0 | 9.0 | 9.0 | 7.5 | 8.0 | 2.7 | 6.5 | 7.5 |
| | .063 | 1.5 | 6.3* | 1.5 | 6.3* | 8.0 | 4.5 | 7.0 | 1.7 | 2.0 | 6.5 |
| | .032 | 3.0 | 4.5* | 0.0 | 4.5* | 4.5* | 9.0 | 5.0 | 1.0 | 2.0 | 7.0 |
| Methyl o-(4-isopropyl-4-methyl-5-thioxo-2-imidazolin-2-yl)benzoate; | 2.000 | 8.0 | 9.0 | 8.0 | 6.5 | 9.0 | 8.0 | 9.0 | 3.5 | 5.0 | 8.0 |
| | 1.000 | 8.0 | 8.0 | 8.0 | 4.5 | 9.0 | 8.0 | 8.0 | 1.5 | 4.0 | 8.0 |
| | .500 | 6.0 | 7.0 | 8.0 | 2.5 | 8.5 | 6.0 | 7.0 | 0.0 | 3.0 | 8.0 |
| | .250 | 2.0 | 3.5 | 7.0 | 1.0 | 3.0 | 5.0 | 5.0 | 0.0 | 2.0 | 5.0 |
| | .125 | 0.0 | 2.5 | 8.0 | 0.0 | 3.5* | 2.0 | 4.0 | 0.0 | 0.0 | 4.0 |
| | .063 | 0.0 | 1.0 | 3.0 | 0.0 | 0.0 | 0.0 | 1.0 | 0.0 | 0.0 | 3.0 |
| | .032 | | 0.0 | | 0.0 | 0.0 | | | 0.0 | | |
| 3-Fluoro-2-(4-isopropyl-4-methyl-5-thioxo-2-imidazolin-2-yl)benzoic acid; | 2.000 | 9.0 | 9.0 | 6.0 | 0.0 | 0.0 | 8.0 | 9.0 | 5.0 | 9.0 | 8.0 |
| | 1.000 | 7.0 | 9.0 | 3.0 | 0.0 | | 8.0 | 8.0 | 4.0 | 7.0 | 7.0 |
| | .500 | 6.0 | 9.0 | 2.0 | 0.0 | | 8.0 | 9.0 | 2.0 | 7.0 | 7.0 |
| | .250 | 6.0 | 9.0 | 0.0 | 9.0 | | 8.0 | 8.0 | 1.0 | 3.0 | 5.0 |
| | .125 | 0.0 | 3.0 | 0.0 | 9.0 | 9.0 | 7.0 | 3.0 | 0.0 | 1.0 | 5.0 |
| | .063 | 0.0 | 0.0 | 0.0 | 0.0 | 6.0 | 4.0 | 2.0 | 0.0 | 0.0 | 4.0 |
| (R)-(+)-o-(4-Isopropyl-4-methyl-5-thioxo-2-imidazolin-2-yl)benzoic acid; | 2.000 | 9.0 | 9.0 | 9.0 | 9.0 | | 8.0 | 9.0 | 9.0 | 9.0 | 8.0 |
| | 1.000 | 9.0 | 9.0 | 9.0 | 9.0 | | 8.0 | 9.0 | 8.0 | 9.0 | 8.0 |
| | .500 | 9.0 | 9.0 | 9.0 | 9.0 | | 8.0 | 9.0 | 8.0 | 9.0 | 8.0 |
| | .250 | 9.0 | 9.0 | 6.0 | 9.0 | | 8.0 | 8.0 | 5.0 | 9.0 | 8.0 |
| | .125 | 6.0 | 9.0 | 3.0 | 9.0 | | 8.0 | 9.0 | 4.0 | 7.0 | 8.0 |
| | .063 | 6.0 | 9.0 | 2.0 | 9.0 | | 8.0 | 8.0 | 3.0 | 7.0 | 9.0 |
| (R)-(+)-Methyl o-(4-isopropyl-4-methyl-5-thioxo-2-imidazolin-2-yl)benzoate; | 2.000 | 8.0 | 9.0 | 9.0 | 9.0 | 9.0 | 8.0 | 9.0 | 5.0 | 7.0 | 9.0 |
| | 1.000 | 8.0 | 9.0 | 9.0 | 9.0 | 9.0 | 8.0 | 9.0 | 5.0 | 7.0 | 8.0 |
| | .500 | 7.0 | 9.0 | 7.0 | 9.0 | 8.0 | 8.0 | 8.0 | 2.0 | 8.0 | 8.0 |
| | .250 | 4.0 | 7.0 | 6.0 | 9.0 | 6.0 | 6.0 | 5.0 | 3.0 | 5.0 | 8.0 |
| | .125 | 3.0 | 6.0 | 4.0 | 9.0 | 4.0 | 4.0 | 3.0 | 1.0 | 3.0 | 9.0 |
| | .063 | 2.0 | 3.0 | 2.0 | 9.0 | 2.0 | 3.0 | 2.0 | 2.0 | 2.0 | 9.0 |
| Benzyl o-(4-isopropyl-4-methyl-5-thioxo-2-imidazolin-2-yl)-benzoate; | 2.000 | 4.0 | 8.0 | 3.0 | 9.0 | 9.0 | 8.0 | 7.0 | 1.0 | 3.0 | 5.0 |
| | 1.000 | 0.0 | 3.0 | 0.0 | 9.0 | 9.0 | 8.0 | 3.0 | 2.0 | 3.0 | 5.0 |
| | .500 | 0.0 | 3.0 | 0.0 | 9.0 | 5.0 | 3.0 | 3.0 | 0.0 | 2.0 | 3.0 |
| | .250 | 0.0 | 0.0 | 0.0 | 0.0 | 0.0 | 2.0 | 2.0 | 1.0 | 2.0 | 2.0 |
| | .125 | 0.0 | 0.0 | 0.0 | 0.0 | 0.0 | 0.0 | 0.0 | 0.0 | 1.0 | 1.0 |
| | .063 | 0.0 | 0.0 | 0.0 | 0.0 | 0.0 | 0.0 | 0.0 | 0.0 | 1.0 | 1.0 |
| Isopropylammonium o-(4-isopropyl-4-methyl-5-thioxo-2-imidazolin-2-yl) benzoic acid; | 2.000 | 7.0 | 9.0 | 9.0 | 9.0 | 9.0 | 8.0 | 8.0 | 9.0 | 9.0 | 9.0 |
| | 1.000 | 7.0 | 9.0 | 8.0 | 9.0 | 9.0 | 8.0 | 8.0 | 9.0 | 9.0 | 9.0 |
| | .500 | 5.0 | 5.0 | 6.0 | 6.0 | 5.0 | 8.0 | 8.0 | 6.0 | 9.0 | 9.0 |
| | .250 | 3.0 | 3.0 | 3.0 | | 0.0 | 6.0 | 8.0 | 3.0 | 6.0 | 8.0 |
| | .125 | 0.0 | 3.0 | 3.0 | | 9.0 | 6.0 | 8.0 | 3.0 | 4.0 | 8.0 |
| | .063 | 0.0 | 0.0 | 2.0 | | 9.0 | 4.0 | 4.0 | 3.0 | 3.0 | 7.0 |
| Benzyltrimethylammonium o-(4-isopropyl-4-methyl-5-thioxo-2-imidazolin-2-yl)benzoic acid; | 2.000 | 8.0 | 9.0 | 9.0 | 9.0 | 9.0 | 8.0 | 8.0 | 9.0 | 8.0 | 0.0 |
| | 1.000 | 8.0 | 9.0 | 5.0 | 9.0 | 9.0 | 8.0 | 8.0 | 5.0 | 7.0 | 9.0 |
| | .500 | 5.0 | 9.0 | 4.0 | 9.0 | 9.0 | 8.0 | 8.0 | 3.0 | 6.0 | 9.0 |
| | .250 | 3.0 | 6.0 | 2.0 | 9.0 | 9.0 | 8.0 | 6.0 | 2.0 | 4.0 | 9.0 |
| | .125 | 2.0 | 5.0 | 2.0 | 9.0 | 9.0 | 8.0 | 3.0 | 2.0 | 3.0 | 5.0 |
| | .063 | 1.0 | 2.0 | 0.0 | 0.0 | 5.0 | 4.0 | 2.0 | 1.0 | 2.0 | 3.0 |

TABLE III-continued
PRE-EMERGENCE TESTS - RATES IN KG/HA

| Compound | RATE | BARN YARDGR | P NUT SEDGE | WILD OATS | QUACK GRASS | FLD BINDWD | MRNGLRY SP | VELVET LEAF | S BARLEY LA | CORN FIELD | SOYBEAN WI |
|---|---|---|---|---|---|---|---|---|---|---|---|
| 2-Propynyl o-(4-isopropyl-4-methyl-5-thioxo-2-imidazolin-2-yl)-benzoate; | 2.000 | 9.0 | 9.0 | 9.0 | 9.0 | 9.0 | 8.0 | 9.0 | 9.0 | 7.0 | 8.0 |
| | 1.000 | 7.0 | 9.0 | 9.0 | 9.0 | 9.0 | 8.0 | 8.0 | 5.0 | 6.0 | 8.0 |
| | .500 | 7.0 | 9.0 | 6.0 | 9.0 | 9.0 | 8.0 | 8.0 | 4.0 | 5.0 | 9.0 |
| | .250 | 6.0 | 9.0 | 3.0 | 9.0 | 9.0 | 8.0 | 6.0 | 3.0 | 3.0 | 8.0 |
| | .125 | 0.0 | 8.0 | 3.0 | 9.0 | 9.0 | 9.0 | 6.0 | 2.0 | 2.0 | 8.0 |
| | .063 | 0.0 | 5.0 | 2.0 | 9.0 | 3.0 | 2.0 | 4.0 | 1.0 | 2.0 | 5.0 |
| Ethyl o-(4-isopropyl-4-methyl-5-thioxo-2-imidazolin-2-yl)benzoate; | 2.000 | 3.0 | 8.0 | 9.0 | 9.0 | 4.0 | 7.0 | 2.0 | 3.0 | 2.0 | 5.0 |
| | 1.000 | 2.0 | 8.0 | 9.0 | 9.0 | 0.0 | 4.0 | 6.0 | 2.0 | 1.0 | 9.0 |
| | .500 | 0.0 | 7.0 | 8.0 | 9.0 | 0.0 | 2.0 | 4.0 | 1.0 | 2.0 | 6.0 |
| | .250 | 0.0 | 6.0 | 6.0 | 9.0 | 0.0 | 0.0 | 3.0 | 1.0 | 1.0 | |
| | .125 | 0.0 | 6.0 | 5.0 | 0.0 | 0.0 | 0.0 | 1.0 | 0.0 | 2.0 | 3.0 |
| | .063 | 0.0 | 3.0 | 3.0 | | 0.0 | 0.0 | 0.0 | 0.0 | 2.0 | 0.0 |
| Furfuryl o-(4-isopropyl-4-methyl-5-thioxo-2-imidazolin-2-yl)-benzoate; | 2.000 | 7.0 | 9.0 | 9.0 | 9.0 | 9.0 | 8.0 | 9.0 | 9.0 | 9.0 | 8.0 |
| | 1.000 | 7.0 | 9.0 | 8.0 | 9.0 | 9.0 | 8.0 | 9.0 | 5.0 | 9.0 | 8.0 |
| | .500 | 7.0 | 9.0 | 6.0 | 9.0 | 9.0 | 8.0 | 9.0 | 5.0 | 6.0 | 8.0 |
| | .250 | 6.0 | 9.0 | 2.0 | 9.0 | 9.0 | 6.0 | 4.0 | 2.0 | 3.0 | 5.0 |
| | .125 | 2.0 | 9.0 | 0.0 | 9.0 | 9.0 | 6.0 | 5.0 | 3.0 | 2.0 | 4.0 |
| | .063 | 0.0 | 3.0 | 0.0 | 0.0 | 0.0 | 3.0 | 3.0 | 0.0 | 2.0 | 3.0 |
| Methyl o-(4-isopropyl-4-methyl-5-thioxo-2-imidazolin-2-yl)benzoate hydrochloride; | 2.000 | 9.0 | 9.0 | 9.0 | 3.0 | 9.0 | 8.0 | 9.0 | 4.0 | 7.0 | 9.0 |
| | 1.000 | 4.0 | 8.0 | 8.0 | | 6.0 | 6.0 | 8.0 | 0.0 | 5.0 | 8.0 |
| | .500 | 4.0 | 8.0 | 6.0 | 0.0 | 4.0 | 6.0 | 5.0 | 2.0 | 2.0 | 7.0 |
| | .250 | 2.0 | 4.0 | 5.0 | 0.0 | 0.0 | 3.0 | 3.0 | 0.0 | 1.0 | 6.0 |
| | .125 | 0.0 | 0.0 | 0.0 | 0.0 | 0.0 | 2.0 | 0.0 | 0.0 | 0.0 | 3.0 |
| | .063 | 0.0 | 0.0 | 0.0 | 0.0 | 0.0 | 0.0 | 0.0 | 0.0 | 0.0 | 3.0 |
| Isopropyl o-(4-isopropyl-4-methyl-5-thioxo-2-imidazolin-2-yl)benzoate; | 2.000 | 0.0 | 6.0 | 0.0 | 9.0 | 0.0 | 3.0 | 3.0 | 0.0 | 0.0 | 3.0 |
| | 1.000 | 0.0 | 3.0 | 0.0 | 9.0 | 0.0 | 3.0 | 2.0 | 0.0 | 0.0 | 3.0 |
| | .500 | 0.0 | 3.0 | 0.0 | 9.0 | 0.0 | 3.0 | 0.0 | 0.0 | 0.0 | 2.0 |
| | .250 | 0.0 | 3.0 | 0.0 | 9.0 | 0.0 | 0.0 | 0.0 | 0.0 | 0.0 | 0.0 |
| | .125 | 0.0 | 2.0 | 0.0 | 9.0 | 0.0 | 0.0 | 0.0 | 0.0 | 0.0 | 0.0 |
| | .063 | 0.0 | 0.0 | 0.0 | 9.0 | 0.0 | 0.0 | 0.0 | 0.0 | 0.0 | 0.0 |
| Methyl 3-fluoro-2-(4-isopropyl-4-methyl-5-thioxo-2-imidazolin-2-yl)-benzoate. | 2.000 | 7.0 | 9.0 | 0.0 | 9.0 | 9.0 | 8.0 | 8.0 | 0.0 | 4.0 | 8.0 |
| | 1.000 | 4.0 | 7.0 | 7.0 | 9.0 | 9.0 | 8.0 | 7.0 | 0.0 | 3.0 | 8.0 |
| | .500 | 2.0 | 5.0 | 2.0 | 0.0 | 8.0 | 7.0 | 5.0 | 0.0 | 0.0 | 7.0 |
| | .250 | 0.0 | 3.0 | 0.0 | 0.0 | 6.0 | 6.0 | 5.0 | 0.0 | 0.0 | 7.0 |
| | .125 | 0.0 | 0.0 | 0.0 | 0.0 | 2.0 | 3.0 | 2.0 | 0.0 | 0.0 | 3.0 |
| | .063 | 0.0 | 0.0 | 0.0 | 0.0 | 0.0 | 2.0 | 0.0 | 0.0 | 0.0 | 3.0 |

EXAMPLE 18

Postemergence herbicidal evaluation of test compounds

The postemergence herbicidal activity of test compounds is determined using the procedure of Example 16, excepting that test compounds are applied at rates of application between 0.063 and 2.0 kg/ha to the foliage of test plant species. The rating system employed is the same as that described in Example 16, and the plant species used are as follows:

| | |
|---|---|
| Barnyardgrass | (*Echinochloa crusgalli*) |
| Purple Nutsedge | (*Cyperus rotundus* L.) |
| Wild Oats | (*Avena fatus*) |
| Quackgrass | (*Agropyron repens*) |
| Field Bindweed | (*Convolvulus arvensis* L.) |
| Morningglory | (*Ipomoea purpurea*) |
| Velvetleaf | (*Abutilon theophrasti*) |
| Barley | (*Hordeum vulgare*) |
| Corn | (*Zea mays*) |
| Green Foxtail | (*Setaria viridis*) |
| Wild Mustard | (*Brassica kaber*) |
| Sugar Beets | (*Beta vulgaris*) |
| Cotton | (*Gossypium hirsutum*) |
| Rice Paddy | (*Oryza sativa*) |

Data obtained are reported in Table VI below.

TABLE IV

POST-EMERGENCE TESTS -- RATES IN KG/HA

| Compound | RATE | BARN YARD GR | GREEN FOX | P NUT SEDGE | WILD OATS | QUACK GRASS | FLD B INDWD | MRNGLRY SP | WILD MUSTD | VELVET LEAF | S BARLY LA | SUGAR BEETS | CORN FIELD | COTTON | RICE PADDY |
|---|---|---|---|---|---|---|---|---|---|---|---|---|---|---|---|
| 2-Isopropyl-2-methyl-3-thio-5H-imidazo[2,1-a]isoindole-3(2H),5-dione | 2.000 | 9.0 | 9.0 | 8.0 | 8.0 | 8.0 | 9.0 | 8.0 | 9.0 | 9.0 | 7.0 | 9.0 | 9.0 | 8.0 | 3.0 |
|  | 1.000 | 9.0 | 9.0 | 5.5 | 8.0 | 8.0 | 8.5 | 8.0 | 9.0 | 8.0 | 7.0 | 9.0 | 9.0 | 8.0 | 1.0 |
|  | .500 | 8.5 | 7.0 | 5.0 | 7.0 | 6.5 | 8.5 | 8.0 | 9.0 | 9.0 | 6.0 | 9.0 | 8.0 | 8.0 | 1.0 |
|  | .250 | 5.0 | 3.0 | 4.0 | 3.0 | 4.0 | 8.5 | 6.0 | 9.0 | 7.0 | 4.0 | 9.0 | 9.0 | 8.0 | 1.0 |
|  | .125 | 2.5 | 0.0 | 1.5 | 0.0 | 3.0* | 6.0 | 3.0 | 9.0 | 3.0 | 3.0 | 9.0 | 7.0 | 6.0 | 0.0 |
|  | .063 | 0.0 | 0.0 | 1.0 | 0.0 | 1.5 | 3.0 | 2.0 | 9.0 | 1.0 | 2.0 | 9.0 | 3.0 | 3.0 | 1.0 |
| Isopropyl o-(4-isopropyl-4-methyl-5-thioxo-2-imidazolin-2-yl)benzoate | 2.000 | 0.0 | 0.0 | 0.0 | 0.0 | 0.0 | 0.0 | 2.0 | 9.0 | 0.0 | 2.0 | 9.0 | 0.0 | 7.0 | 0.0 |
|  | 1.000 | 0.0 | 0.0 | 0.0 | 0.0 | 0.0 | 0.0 | 5.0 | 6.0 | 0.0 | 0.0 | 9.0 | 0.0 | 7.0 | 0.0 |
|  | .500 | 0.0 | 0.0 | 0.0 | 0.0 | 0.0 | 0.0 | 2.0 | 5.0 | 0.0 | 0.0 | 6.0 | 0.0 | 7.0 | 0.0 |
|  | .250 | 0.0 | 0.0 | 0.0 | 0.0 | 0.0 | 0.0 | 2.0 | 3.0 | 0.0 | 0.0 | 5.0 | 0.0 | 7.0 | 0.0 |
|  | .125 | 0.0 | 0.0 | 0.0 | 0.0 | 0.0 | 0.0 | 0.0 | 4.0 | 0.0 | 0.0 | 3.0 | 0.0 | 5.0 | 0.0 |
|  | .063 | 0.0 | 0.0 | 0.0 | 0.0 | 0.0 | 0.0 | 0.0 | 0.0 | 0.0 | 0.0 | 3.0 | 0.0 | 3.0 | 0.0 |
| Sodium o-(4-isopropyl-4-methyl-5-thioxo-2-imidazolin-2-yl)benzoate | 1.000 | 9.0 | 6.0 | 6.0 | 9.0 | 3.0 | 9.0 | 7.0 | 9.0 | 9.0 | 9.0 | 9.0 | 9.0 | 6.0 | 0.0 |
|  | .500 | 5.0 | 8.0 | 3.0 | 3.0 | 0.0 | 6.0 | 3.0 | 6.0 | 3.0 | 6.0 | 9.0 | 4.0 | 6.0 | 0.0 |
|  | .250 | 3.0 | 6.0 | 2.0 | 0.0 | 0.0 | 5.0 | 3.0 | 9.0 | 0.0 | 4.0 | 9.0 | 3.0 | 5.0 | 0.0 |
|  | .125 | 0.0 | 0.0 | 0.0 | 0.0 | 0.0 | 4.0 | 2.0 | 9.0 | 0.0 | 2.0 | 9.0 | 3.0 | 3.0 | 0.0 |
|  | .063 | 0.0 | 0.0 | 0.0 | 0.0 | 0.0 | 3.0 | 0.0 | 9.0 | 0.0 | 1.0 | 9.0 | 2.0 | 0.0 | 0.0 |
| (R)-(+)-2-isopropyl-2-methyl-3-thio-5-H-imidazo[2,1-a]-isoindole-3(2H),5-dione | 2.000 | 8.5 | 9.0 | 8.0 | 9.0 | 8.5 | 9.0 | 8.0 | 9.0 | 9.0 | 9.0 | 9.0 | 9.0 | 7.0 | 0.0 |
|  | 1.000 | 8.5 | 9.0 | 8.0 | 9.0 | 8.0 | 9.0 | 7.0 | 9.0 | 9.0 | 9.0 | 9.0 | 9.0 | 7.0 | 0.0 |
|  | .500 | 7.5 | 9.0 | 8.0 | 6.0 | 8.0 | 9.0 | 7.0 | 9.0 | 9.0 | 9.0 | 9.0 | 9.0 | 7.0 | 1.0 |
|  | .250 | 6.5 | 7.0 | 3.5 | 6.0 | 7.5 | 9.0 | 5.0 | 9.0 | 7.0 | 7.0 | 9.0 | 9.0 | 4.0 | 0.0 |
|  | .125 | 3.0 | 7.0 | 5.5 | 3.0 | 8.0 | 9.0 | 3.0 | 9.0 | 6.0 | 9.0 | 9.0 | 9.0 | 5.0 | 0.0 |
|  | .063 | 1.0 | 4.0 | 2.0 | 2.0 | 4.5 | 6.0 | 2.0 | 9.0 | 3.0 | 4.0 | 9.0 | 5.0 | 3.0 | 0.0 |
| Calcium o-(4-isopropyl-4-methyl-5-thioxo-2-imidazolin-2-yl)benzoate | 2.000 | 7.0 | 7.0 | 8.0 | 9.0 | 8.0 | 7.0 | 3.0 | 9.0 | 4.0 | 9.0 | 9.0 | 9.0 | 5.0 | 0.0 |
|  | 1.000 | 7.0 | 7.0 | 7.0 | 7.0 | 8.0 | 9.0 | 2.0 | 9.0 | 3.0 | 9.0 | 9.0 | 9.0 | 5.0 | 0.0 |
|  | .500 | 3.0 | 7.0 | 5.0 | 4.0 | 4.0 | 9.0 | 2.0 | 9.0 | 0.0 | 7.0 | 9.0 | 7.0 | 5.0 | 0.0 |
|  | .250 | 0.0 | 3.0 |  | 0.0 | 9.0 | 6.0 | 0.0 | 9.0 | 0.0 | 6.0 | 9.0 | 6.0 | 3.0 | 0.0 |
|  | .125 | 0.0 | 0.0 | 0.0 | 0.0 | 0.0 | 3.0 | 0.0 | 9.0 | 0.0 | 7.0 | 9.0 | 7.0 | 3.0 | 0.0 |
|  | .063 | 0.0 | 0.0 | 0.0 | 0.0 | 0.0 | 7.0 | 0.0 | 9.0 | 0.0 | 4.0 | 9.0 | 9.0 | 3.0 | 0.0 |
| Methyl 2-(4-isopropyl-4-methyl-5-thioxo-2-imidazolin-2-yl)-p-toluate | 2.000 | 4.0 | 0.0 | 0.0 | 9.0 | 0.0 | 7.0 | 0.0 | 9.0 | 2.0 | 4.0 | 9.0 | 3.0 | 3.0 | 0.0 |
|  | 1.000 | 2.0 | 0.0 | 0.0 | 7.0 | 0.0 | 9.0 | 0.0 | 9.0 | 2.0 | 0.0 | 9.0 | 2.0 | 0.0 | 0.0 |
|  | .500 | 0.0 | 0.0 | 0.0 | 7.0 | 0.0 | 6.0 | 0.0 | 9.0 | 0.0 | 0.0 | 0.0 | 0.0 | 0.0 | 0.0 |
|  | .250 | 0.0 | 0.0 | 0.0 | 6.0 | 0.0 | 3.0 | 0.0 | 9.0 | 0.0 | 0.0 | 0.0 | 0.0 | 0.0 | 0.0 |
|  | .125 | 0.0 | 0.0 | 0.0 | 4.0 | 0.0 | 0.0 | 0.0 | 7.0 | 0.0 | 0.0 | 0.0 | 0.0 | 0.0 | 0.0 |
|  | .063 | 0.0 | 0.0 | 0.0 | 2.0 | 0.0 | 0.0 | 0.0 | 6.0 | 0.0 | 0.0 | 0.0 | 0.0 | 0.0 | 0.0 |
| 2-Isopropyl-2,8-dimethyl-3-thio-5H-imidazo[2,1-a]-isoindole-3(2H),5-dione | 2.000 | 0.0 | 0.0 | 0.0 | 9.0 | 0.0 | 9.0 | 0.0 | 9.0 | 0.0 | 6.0 | 9.0 | 3.0 | 2.0 | 3.0 |
|  | 1.000 | 0.0 | 0.0 | 0.0 | 9.0 | 0.0 | 9.0 | 0.0 | 9.0 | 0.0 | 3.0 | 9.0 | 0.0 | 0.0 | 2.0 |
|  | .500 | 0.0 | 0.0 | 0.0 | 9.0 | 0.0 | 6.0 | 0.0 | 9.0 | 0.0 | 3.0 | 9.0 | 2.0 | 0.0 | 2.0 |
|  | .250 | 0.0 | 0.0 | 0.0 | 8.0 | 0.0 | 6.0 | 0.0 | 9.0 | 0.0 | 3.0 | 9.0 | 1.0 | 0.0 | 0.0 |
|  | .125 | 0.0 | 0.0 | 0.0 | 7.0 | 0.0 | 5.0 | 0.0 | 9.0 | 0.0 | 1.0 | 9.0 | 0.0 | 0.0 | 0.0 |
|  | .063 | 0.0 | 2.0 | 0.0 | 5.0 | 0.0 | 5.0 | 0.0 | 6.0 | 0.0 | 0.0 | 0.0 | 0.0 | 0.0 | 3.0 |
| 2-(4-Isopropyl-4-methyl-5-thioxo-2-imidazolin-2-yl)-p-toluic acid | 2.000 | 0.0 | 0.0 | 0.0 | 9.0 | 0.0 | 9.0 | 0.0 | 9.0 | 0.0 | 4.0 | 9.0 | 3.0 | 4.0 | 3.0 |
|  | 1.000 | 0.0 | 0.0 | 0.0 | 9.0 | 0.0 | 9.0 | 0.0 | 9.0 | 0.0 | 3.0 | 9.0 | 0.0 | 3.0 | 4.0 |
|  | .500 | 0.0 | 0.0 | 0.0 | 9.0 | 0.0 | 9.0 | 0.0 | 9.0 | 0.0 | 3.0 | 9.0 | 0.0 | 3.0 | 3.0 |
|  | .250 | 0.0 | 0.0 | 0.0 | 9.0 | 0.0 | 8.0 | 0.0 | 9.0 | 0.0 | 2.0 | 9.0 | 0.0 | 2.0 | 3.0 |
|  | .125 | 0.0 | 0.0 | 0.0 | 6.0 | 0.0 | 6.0 | 0.0 | 7.0 | 0.0 | 0.0 | 9.0 | 0.0 | 0.0 | 3.0 |
|  | .063 | 0.0 | 0.0 | 0.0 | 5.0 | 0.0 | 6.0 | 5.0 | 7.0 | 0.0 | 0.0 | 9.0 | 0.0 | 0.0 | 0.0 |
| Methyl 2-(4-isopropyl-4-methyl-5-thioxo-2-imidazolin- | 2.000 | 5.0 | 0.0 | 0.0 | 9.0 | 0.0 | 4.0 | 0.0 | 7.0 | 0.0 | 0.0 | 9.0 | 0.0 | 0.0 | 0.0 |
|  | 1.000 | 0.0 | 0.0 | 2.0 | 9.0 | 0.0 |  | 0.0 | 7.0 | 0.0 | 0.0 | 5.0 | 0.0 | 0.0 | 0.0 |

TABLE IV-continued
POST-EMERGENCE TESTS - RATES IN KG/HA

| Compound | RATE | BARN YARD GR | GREEN FOX | P NUT SEDGE | WILD OATS | QUACK GRASS | FLD B INDWD | MRNGLRY SP | WILD MUSTD | VELVET LEAF | S BARLY LA | SUGAR BEETS | CORN FIELD | COTTON | RICE PADDY |
|---|---|---|---|---|---|---|---|---|---|---|---|---|---|---|---|
| 2-yl)-p-toluate and methyl 6-(4-isopropyl-4-methyl-5-thioxo-2-imidazolin-2-yl)-m-toluate | .500 | 0.0 | 0.0 | 0.0 | 7.0 | 0.0 | 0.0 | 0.0 | 6.0 | 0.0 | 0.0 | 4.0 | 0.0 | 0.0 | 0.0 |
| | .250 | 0.0 | 0.0 | 0.0 | 7.0 | 0.0 | 0.0 | 0.0 | 5.0 | 0.0 | 0.0 | 2.0 | 0.0 | 0.0 | 0.0 |
| | .125 | 0.0 | 0.0 | 0.0 | 5.0 | 0.0 | 0.0 | 0.0 | 6.0 | 0.0 | 0.0 | 2.0 | 0.0 | 0.0 | 0.0 |
| | .063 | 0.0 | 0.0 | 0.0 | 4.0 | 0.0 | 0.0 | 0.0 | 5.0 | 0.0 | 0.0 | 0.0 | 0.0 | 0.0 | 0.0 |
| 2-(4-Isopropyl-4-methyl-5-thioxo-2-imidazolin-2-yl)-p-toluic acid and 6-(4-isopropyl-4-methyl-5-thioxo-2-imidazolin-2-yl)-m-toluic acid | 2.000 | 0.0 | 0.0 | 0.0 | 9.0 | 0.0 | 9.0 | 0.0 | 9.0 | 0.0 | 6.0 | 9.0 | 3.0 | 3.0 | 0.0 |
| | 1.000 | 0.0 | 0.0 | 0.0 | 9.0 | 0.0 | 9.0 | 0.0 | 9.0 | 0.0 | 3.0 | 9.0 | 2.0 | 3.0 | 0.0 |
| | .500 | 0.0 | 0.0 | 0.0 | 9.0 | 0.0 | 9.0 | 0.0 | 9.0 | 0.0 | 3.0 | 9.0 | 0.0 | 2.0 | 0.0 |
| | .250 | 0.0 | 0.0 | 0.0 | 9.0 | 0.0 | 8.0 | 0.0 | 9.0 | 0.0 | 2.0 | 9.0 | 0.0 | 0.0 | 0.0 |
| | .125 | 0.0 | 0.0 | 0.0 | 7.0 | 0.0 | 7.0 | 0.0 | 7.0 | 0.0 | 2.0 | 9.0 | 0.0 | 0.0 | 0.0 |
| | .063 | 0.0 | 0.0 | 0.0 | 4.0 | 0.0 | 0.0 | 0.0 | 5.0 | 0.0 | 1.0 | 9.0 | 0.0 | 0.0 | 0.0 |
| 6-(4-Isopropyl-4-methyl-5-thioxo-2-imidazolin-2-yl)-m-toluic acid | 2.000 | 7.5 | 8.0 | 8.0 | 9.0 | 9.0 | 9.0 | 4.5 | 9.0 | 8.5 | 9.0 | 9.0 | 6.0 | 2.5 | 7.0 |
| | 1.000 | 7.0 | 6.5 | 3.0 | 9.0 | 8.0 | 9.0 | 3.5 | 9.0 | 7.5 | 9.0 | 9.0 | 5.0 | 2.0 | 5.0 |
| | .500 | 5.5 | 7.0 | 3.0 | 7.0 | 6.0 | 9.0 | 1.0 | 9.0 | 5.5 | 9.0 | 9.0 | 4.0 | 1.5 | 4.0 |
| | .250 | 2.0 | 5.5 | 0.0 | 7.0 | 3.0 | 9.0 | 0.0 | 9.0 | 3.0 | 8.0 | 9.0 | 3.0 | 1.0 | 4.0 |
| | .125 | 0.5 | 4.5 | 0.0 | 5.0 | 2.0 | 7.0 | 0.0 | 5.0 | 1.0 | 5.0 | 9.0 | 1.0 | 1.0 | 4.0 |
| | .063 | 0.5 | 3.5 | 0.0 | 4.0 | 0.0 | 7.0 | 0.0 | 0.0 | 0.0 | 3.0 | 9.0 | 0.0 | 0.5 | 2.0 |
| Methyl 6-(4-isopropyl-4-methyl-5-thioxo-2-imidazolin-2-yl)-m-toluate | 2.000 | 0.0 | 0.0 | 0.0 | 9.0 | 0.0 | 9.0 | 0.0 | 9.0 | 0.0 | 3.0 | 8.0 | 3.0 | 3.0 | 0.0 |
| | 1.000 | 0.0 | 0.0 | 0.0 | 7.0 | 8.0 | 9.0 | 5.0 | 9.0 | 0.0 | 7.0 | 6.0 | 2.0 | 2.0 | 6.0 |
| | .500 | 0.0 | 0.0 | 0.0 | 6.0 | 8.0 | 9.0 | 2.0 | 9.0 | 0.0 | 8.0 | 3.0 | 0.0 | 4.0 | 5.0 |
| | .250 | 0.0 | 0.0 | 0.0 | 5.0 | 7.0 | 9.0 | 0.0 | 8.0 | 0.0 | 6.0 | 2.0 | 0.0 | 3.0 | 3.0 |
| | .125 | 0.0 | 0.0 | 0.0 | 3.0 | 4.0 | 7.0 | 0.0 | 6.0 | 0.0 | 4.0 | 9.0 | 0.0 | 2.0 | 3.0 |
| | .063 | 0.0 | 0.0 | 0.0 | 2.0 | 0.0 | 7.0 | 0.0 | 3.0 | 0.0 | 3.0 | 9.0 | 0.0 | 2.0 | 3.0 |
| 2-Isopropyl-2,7-dimethyl-3-thio-5H-imidazo[2,1-a]isoindole-3(2H),5-dione | 2.000 | 5.0 | 7.0 | 7.0 | 4.0 | 0.0 | 9.0 | 5.0 | 9.0 | 9.0 | 1.0 | 0.0 | 0.0 | 2.0 | 6.0 |
| | 1.000 | 3.0 | 6.0 | 5.0 | 7.0 | 8.0 | 9.0 | 2.0 | 9.0 | 6.0 | 7.0 | 9.0 | 3.0 | 5.0 | 6.0 |
| | .500 | 2.0 | 6.0 | 2.0 | 6.0 | 7.0 | 9.0 | 0.0 | 8.0 | 4.0 | 8.0 | 8.0 | 2.0 | 4.0 | 5.0 |
| | .250 | 0.0 | 5.0 | 0.0 | 5.0 | 4.0 | 7.0 | 0.0 | 6.0 | 3.0 | 6.0 | 8.0 | 0.0 | 3.0 | 3.0 |
| | .125 | 0.0 | 3.0 | 0.0 | 3.0 | 0.0 | 9.0 | 0.0 | 3.0 | 0.0 | 4.0 | 9.0 | 0.0 | 2.0 | 3.0 |
| | .063 | 0.0 | 2.0 | 0.0 | 2.0 | 0.0 | 9.0 | 0.0 | 0.0 | 0.0 | 3.0 | 9.0 | 0.0 | 2.0 | 3.0 |
| 9-Fluoro-1,9bα-dihydro-3-isopropyl-3-methyl-2-thio-5H-imidazo[2,1-a]isoindole-2(3H),5-dione | 2.000 | 0.0 | 0.0 | 3.0 | 0.0 | 0.0 | 3.0 | 7.0 | 0.0 | 4.0 | 1.0 | 9.0 | 0.0 | 2.0 | 2.0 |
| | 1.000 | 0.0 | 0.0 | 2.0 | 0.0 | 0.0 | 9.0 | 7.0 | 8.0 | 2.0 | 0.0 | 9.0 | 0.0 | 7.0 | 6.0 |
| | .500 | 0.0 | 0.0 | 0.0 | 0.0 | 0.0 | 9.0 | 5.0 | 7.0 | 0.0 | 0.0 | 9.0 | 0.0 | 5.0 | 5.0 |
| | .250 | 0.0 | 0.0 | 0.0 | 0.0 | 0.0 | 0.0 | 3.0 | 6.0 | 0.0 | 0.0 | 7.0 | 0.0 | 5.0 | 3.0 |
| | .125 | 0.0 | 0.0 | 0.0 | 0.0 | 0.0 | 0.0 | 2.0 | 3.0 | 0.0 | 0.0 | 5.0 | 0.0 | 4.0 | 3.0 |
| | .063 | 0.0 | 0.0 | 3.0 | 0.0 | 0.0 | 0.0 | 0.0 | 3.0 | 0.0 | 0.0 | 3.0 | 0.0 | 3.0 | 2.0 |
| 9-Fluoro-2-isopropyl-2-methyl-3-thio-5H-imidazo[2,1-a]isoindole-3(2H),5-dione | 2.000 | 7.0 | 5.0 | 8.0 | 5.0 | 0.0 | 9.0 | 9.0 | 9.0 | 9.0 | 4.0 | 9.0 | 8.0 | 9.0 | 2.0 |
| | 1.000 | 6.0 | 2.0 | 8.0 | 2.0 | 0.0 | 9.0 | 9.0 | 9.0 | 9.0 | 3.0 | 9.0 | 7.0 | 9.0 | 2.0 |
| | .500 | 2.0 | 0.0 | 8.0 | 0.0 | 0.0 | 9.0 | 8.0 | 9.0 | 8.0 | 2.0 | 9.0 | 6.0 | 9.0 | 2.0 |
| | .250 | 0.0 | 0.0 | 5.0 | 0.0 | 0.0 | 9.0 | 8.0 | 9.0 | 6.0 | 1.0 | 9.0 | 3.0 | 9.0 | 2.0 |
| | .125 | 0.0 | 0.0 | 5.0 | 0.0 | 0.0 | 7.0 | 8.0 | 9.0 | 6.0 | 0.0 | 9.0 | 2.0 | 7.0 | 2.0 |
| | .063 | 0.0 | 0.0 | 2.0 | 0.0 | 0.0 | 7.0 | 8.0 | 9.0 | 3.0 | 0.0 | 9.0 | 2.0 | 7.0 | 2.0 |
| 1,9bα-Dihydro-3-isopropyl-3-methyl-2-thio-5H-imidazo[2,1-a]isoindole-2(3H),5-dione | 2.000 | | 0.0 | | 3.0 | 7.0 | 8.0 | 8.0 | 9.0 | 8.0 | 0.0 | 9.0 | 8.0 | 8.0 | 2.0 |
| | 1.000 | 2.0 | 0.0 | 3.0 | 2.0 | 0.0 | 8.0 | 8.0 | 9.0 | 8.0 | 0.0 | 9.0 | 6.0 | 7.0 | 2.0 |
| | .500 | 0.0 | 0.0 | 0.0 | 0.0 | 0.0 | 7.0 | 8.0 | 9.0 | 7.0 | 0.0 | 8.0 | 6.0 | 7.0 | 2.0 |
| | .250 | 0.0 | 0.0 | 3.0 | 0.0 | 0.0 | 7.0 | 8.0 | 9.0 | 7.0 | 0.0 | 9.0 | 3.0 | 7.0 | 2.0 |
| | .125 | 0.0 | 0.0 | 2.0 | 0.0 | 0.0 | 6.0 | 8.0 | 9.0 | 3.0 | 0.0 | 8.0 | 2.0 | 6.0 | 2.0 |
| | .063 | 0.0 | 0.0 | 0.0 | 0.0 | 0.0 | 0.0 | 8.0 | 9.0 | 0.0 | 0.0 | 9.0 | 2.0 | 6.0 | 2.0 |
| 1,9bβ-Dihydro-3α-isopropyl-3-methyl-2-thio-5H-imidazo[2,1-a]isoindole-2(3H),5- | 2.000 | 8.0 | 7.0 | 7.0 | 8.0 | 7.0 | 9.0 | 9.0 | 9.0 | 9.0 | 4.0 | 9.0 | 8.0 | 9.0 | 2.0 |
| | 1.000 | 7.0 | 3.0 | 7.0 | 6.0 | 0.0 | 9.0 | 8.0 | 9.0 | 9.0 | 2.0 | 9.0 | 7.0 | 8.0 | 2.0 |
| | .500 | 3.0 | 0.0 | | 3.0 | 0.0 | 9.0 | 9.0 | 9.0 | 9.0 | 2.0 | 9.0 | 6.0 | 8.0 | 2.0 |

TABLE IV-continued

POST-EMERGENCE TESTS -- RATES IN KG/HA

| Compound | RATE | BARN YARD GR | GREEN FOX | P NUT SEDGE | WILD OATS | QUACK GRASS | FLD B INDWD | MRNGLRY SP | WILD MUSTD | VELVET LEAF | S BARLY LA | SUGAR BEETS | CORN FIELD | COTTON | RICE PADDY |
|---|---|---|---|---|---|---|---|---|---|---|---|---|---|---|---|
| dione | .250 | 2.0 | 0.0 | 3.0 | 0.0 | 0.0 | 7.0 | 8.0 | 9.0 | 9.0 | 0.0 | 9.0 | 5.0 | 8.0 | 2.0 |
|  | .125 | 0.0 | 0.0 | 3.0 | 0.0 | 0.0 | 5.0 | 8.0 | 9.0 | 8.0 | 0.0 | 9.0 | 3.0 | 7.0 | 2.0 |
|  | .063 | 0.0 | 0.0 | 0.0 | 0.0 | 0.0 | 5.0 | 8.0 | 9.0 | 7.0 | 0.0 | 9.0 | 2.0 | 7.0 | 2.0 |
| 3-Isopropyl-3-methyl-2-thio- | 2.000 | 9.0 | 0.0 | 4.0 | 0.0 | 0.0 | 9.0 | 8.0 | 9.0 | 8.0 | 2.0 | 9.0 | 4.0 | 7.0 | 2.0 |
| 5H-imidazo[2,1-a]isoindole- | 1.000 | 9.0 | 0.0 | 0.0 | 0.0 | 0.0 | 7.0 | 8.0 | 9.0 | 3.0 | 0.0 | 9.0 | 2.0 | 7.0 | 2.0 |
| 2(3H),5-dione | .500 | 9.0 | 0.0 | 0.0 | 0.0 | 0.0 | 5.0 | 8.0 | 9.0 | 5.0 | 0.0 | 9.0 | 2.0 | 7.0 | 2.0 |
|  | .250 | 9.0 | 0.0 | 0.0 | 0.0 | 0.0 | 5.0 | 8.0 | 9.0 | 3.0 | 0.0 | 9.0 | 2.0 | 7.0 | 2.0 |
|  | .125 | 9.0 | 0.0 | 0.0 | 0.0 | 0.0 | 5.0 | 9.0 | 9.0 | 0.0 | 0.0 | 8.0 | 0.0 | 6.0 | 2.0 |
|  | .063 | 9.0 | 0.0 | 0.0 | 0.0 | 0.0 | 0.0 | 7.0 | 9.0 | 0.0 | 0.0 | 8.0 | 0.0 | 6.0 | 2.0 |
| 2-(4-Isopropyl-4-methyl- | 2.000 | 0.0 | 0.0 | 0.0 | 0.0 | 0.0 | 2.0 | 6.0 | 3.0 | 2.0 | 0.0 | 8.0 | 0.0 | 0.0 | 0.0 |
| 5-thioxo-2-imidazolin-2- | 1.000 | 0.0 | 0.0 | 0.0 | 0.0 | 0.0 | 2.0 | 2.0 | 3.0 | 0.0 | 0.0 | 8.0 | 0.0 | 0.0 | 0.0 |
| yl)-4,6-dimethylbenzoic | .500 | 0.0 | 0.0 | 0.0 | 0.0 | 0.0 | 0.0 | 0.0 | 2.0 | 0.0 | 0.0 | 8.0 | 0.0 | 0.0 | 0.0 |
| acid | .250 | 0.0 | 0.0 | 0.0 | 0.0 | 0.0 | 0.0 | 0.0 | 3.0 | 0.0 | 0.0 | 8.0 | 0.0 | 0.0 | 0.0 |
|  | .125 | 0.0 | 0.0 | 0.0 | 0.0 | 0.0 | 0.0 | 0.0 | 2.0 | 0.0 | 0.0 | 7.0 | 0.0 | 0.0 | 0.0 |
|  | .063 | 0.0 | 0.0 | 0.0 | 0.0 | 0.0 | 0.0 | 0.0 | 2.0 | 0.0 | 0.0 | 7.0 | 0.0 | 0.0 | 0.0 |
| 2-Isopropyl-7-methoxy-2- | 2.000 | 0.0 | 0.0 | 0.0 | 0.0 | 0.0 | 0.0 | 0.0 | 0.0 | 0.0 | 0.0 | 8.0 | 0.0 | 0.0 | 0.0 |
| methyl-3-thio-5H-imidazo- | 1.000 | 0.0 | 0.0 | 0.0 | 0.0 | 0.0 | 0.0 | 0.0 | 0.0 | 0.0 | 0.0 | 7.0 | 0.0 | 0.0 | 0.0 |
| [2,1-a]isoindole-3(2H),5- | .500 | 0.0 | 0.0 | 0.0 | 0.0 | 0.0 | 0.0 | 0.0 | 0.0 | 0.0 | 0.0 | 5.0 | 0.0 | 0.0 | 0.0 |
| dione | .250 | 0.0 | 0.0 | 0.0 | 0.0 | 0.0 | 0.0 | 0.0 | 0.0 | 0.0 | 0.0 | 3.0 | 0.0 | 0.0 | 0.0 |
|  | .125 | 0.0 | 0.0 | 0.0 | 0.0 | 0.0 | 0.0 | 0.0 | 0.0 | 0.0 | 0.0 | 2.0 | 0.0 | 0.0 | 0.0 |
|  | .063 | 0.0 | 0.0 | 0.0 | 0.0 | 0.0 | 0.0 | 0.0 | 0.0 | 0.0 | 0.0 | 0.0 | 0.0 | 0.0 | 0.0 |
| 2-Isopropyl-2,6,8-trimethyl- | 2.000 | 0.0 | 0.0 | 0.0 | 0.0 | 0.0 | 0.0 | 0.0 | 0.0 | 0.0 | 0.0 | 0.0 | 0.0 | 0.0 | 0.0 |
| 3-thio-5H-imidazo[2,1-a]iso- | 1.000 | 0.0 | 0.0 | 0.0 | 0.0 | 0.0 | 0.0 | 0.0 | 0.0 | 0.0 | 0.0 | 0.0 | 0.0 | 0.0 | 0.0 |
| indole-3(2H),5-dione | .500 | 0.0 | 0.0 | 0.0 | 0.0 | 0.0 | 0.0 | 0.0 | 0.0 | 0.0 | 0.0 | 0.0 | 0.0 | 0.0 | 0.0 |
|  | .250 | 0.0 | 0.0 | 0.0 | 0.0 | 0.0 | 0.0 | 0.0 | 0.0 | 0.0 | 0.0 | 0.0 | 0.0 | 0.0 | 0.0 |
|  | .125 | 0.0 | 0.0 | 0.0 | 0.0 | 0.0 | 0.0 | 0.0 | 0.0 | 0.0 | 0.0 | 0.0 | 0.0 | 0.0 | 0.0 |
|  | .063 | 0.0 | 0.0 | 0.0 | 0.0 | 0.0 | 0.0 | 0.0 | 0.0 | 0.0 | 0.0 | 0.0 | 0.0 | 0.0 | 0.0 |

EXAMPLE 19

Preemergence herbicidal evaluation of test compounds

The preemergence herbicidal activity of test compounds is determined using the procedure of Example 17, excepting that test compounds are applied at rates of application between 0.063 and 2.0 kg/ha to soil containing seeds of test plant species. The rating system employed is the same as that described in Example 16, and the plant species used are as follows:

| | |
|---|---|
| Barnyardgrass | (*Echinochloa crusgalli*) |
| Purple Nutsedge | (*Cyperus rotundus* L.) |
| Wild Oats | (*Avena fatus*) |
| Quackgrass | (*Agropyron repens*) |
| Field Bindweed | (*Convolvulus arvensis* L.) |
| Morningglory | (*Ipomoea purpurea*) |
| Velvetleaf | (*Abutilon theophrasti*) |
| Barley | (*Hordeum vulgare*) |
| Corn | (*Zea mays*) |
| Green Foxtail | (*Setaria viridis*) |
| Wild Mustard | (*Brassica kaber*) |
| Sugar Beets | (*Beta vulgaris*) |
| Cotton | (*Gossypium hirsutum*) |
| Rice Paddy | (*Oryza sativa*) |

Data obtained are reported in Table V below.

TABLE V

PRE-EMERGENCE TESTS -- RATES IN KG/HA

| Compound | RATE | BARN YARD GR | GREEN FOX | P NUT SEDGE | WILD OATS | QUACK GRASS | FLD B INDWD | MRNGLRY SP | WILD MUSTD | VELVET LEAF | S BARLY LA | SUGAR BEETS | CORN FIELD | COTTON | RICE PADDY |
|---|---|---|---|---|---|---|---|---|---|---|---|---|---|---|---|
| 2-Isopropyl-2-methyl-3-thio-5H-imidazo[2,1-a]isoindole-3(2H),5-dione | 2.000 | 9.0 | 9.0 | 9.0 | 9.0 | 9.0 | 9.0 | 8.0 | 9.0 | 9.0 | 9.0 | 9.0 | 9.0 | 8.0 | 9.0 |
| | 1.000 | 9.0 | 9.0 | 9.0 | 4.0 | 9.0 | 9.0 | 8.0 | 9.0 | 8.0 | 6.0 | 9.0 | 9.0 | 8.0 | 7.5 |
| | .500 | 7.5 | 9.0 | 9.0 | 6.0 | 9.0 | 9.0 | 8.0 | 9.0 | 8.0 | 4.0 | 9.0 | 9.0 | 8.0 | 8.0 |
| | .250 | 4.5 | 6.0 | 9.0 | 2.0 | 9.0 | 7.3 | 6.0 | 9.0 | 6.0 | 3.0 | 9.0 | 5.0 | 4.0 | 7.0 |
| | .125 | 1.5 | 4.0 | 9.0 | 0.0 | 7.0 | 5.7 | 3.0 | 8.0 | 6.0 | 3.0 | 9.0 | 4.0 | 5.0 | 4.5 |
| | .063 | 0.0 | 0.0 | 7.0 | 0.0 | 4.7 | 3.0 | 2.0 | 8.0 | 3.0 | 2.0 | 9.0 | 3.0 | 2.0 | 1.0 |
| Isopropyl o-(4-isopropyl-4-methyl-5-thioxo-2-imidazolin-2-yl)benzoate | 2.000 | 0.0 | 0.0 | 6.0 | 9.0 | 0.0 | 5.7 | 7.0 | 3.0 | 0.0 | 9.0 | 0.0 | 8.0 | 0.0 | 0.0 |
| | 1.000 | 0.0 | 0.0 | 3.0 | 0.0 | 9.0 | 3.0 | 3.0 | 0.0 | 2.0 | 0.0 | 0.0 | 8.0 | 8.0 | 0.0 |
| | .500 | 0.0 | 0.0 | 3.0 | 0.0 | 9.0 | 0.0 | 3.0 | 0.0 | 0.0 | 0.0 | 8.0 | 0.0 | 8.0 | 0.0 |
| | .250 | 0.0 | 0.0 | 3.0 | 0.0 | 9.0 | 0.0 | 0.0 | 0.0 | 0.0 | 0.0 | 8.0 | 0.0 | 8.0 | 0.0 |
| | .125 | 0.0 | 0.0 | 2.0 | 0.0 | 9.0 | 0.0 | 0.0 | 0.0 | 0.0 | 0.0 | 7.0 | 0.0 | 7.0 | 0.0 |
| | .063 | 0.0 | 0.0 | 0.0 | 0.0 | 9.0 | 0.0 | 0.0 | 0.0 | 0.0 | 0.0 | 0.0 | 0.0 | 0.0 | 0.0 |
| Sodium o-(4-isopropyl-4-methyl-5-thioxo-2-imidazolin-2-yl)benzoate | 2.000 | 9.0 | 9.0 | 9.0 | 9.0 | 9.0 | 9.0 | 8.0 | 9.0 | 9.0 | 9.0 | 9.0 | 9.0 | 3.0 | 8.0 |
| | 1.000 | 6.0 | 9.0 | 9.0 | 6.0 | 9.0 | 9.0 | 8.0 | 9.0 | 9.0 | 9.0 | 9.0 | 9.0 | 7.0 | 7.5 |
| | .500 | 3.0 | 0.0 | 9.0 | 6.0 | 9.0 | 9.0 | 5.0 | 9.0 | 6.0 | 6.0 | 9.0 | 9.0 | 7.0 | 7.5 |
| | .250 | 0.0 | 5.0 | 9.0 | 5.0 | 9.0 | 8.5 | 3.0 | 9.0 | 7.0 | 5.0 | 9.0 | 9.0 | 5.0 | 6.0 |
| | .125 | 0.0 | 0.0 | 9.0 | 0.0 | 9.0 | 9.0 | 3.0 | 9.0 | 5.0 | 4.0 | 9.0 | 8.0 | 4.0 | 3.5 |
| | .063 | 0.0 | 0.0 | 7.0 | 0.0 | 6.5 | 9.0 | 3.0 | 9.0 | 3.0 | 3.0 | 9.0 | 7.0 | 3.0 | 2.0 |
| | .032 | 0.0 | 0.0 | 1.5 | 2.0 | 5.0 | 7.0 | 0.0 | 9.0 | 0.0 | 2.0 | 9.0 | 3.0 | 2.0 | 0.0 |
| (R)-(+)-2-isopropyl-2-methyl-3-thio-5H-imidazo[2,1-a]-isoindole-3-(2H),5-dione | 2.000 | 8.5 | 9.0 | 9.0 | 9.0 | 9.0 | 9.0 | 8.0 | 9.0 | 9.0 | 9.0 | 9.0 | 9.0 | 8.0 | 9.0 |
| | 1.000 | 6.0 | 9.0 | 9.0 | 6.0 | 9.0 | 9.0 | 8.0 | 9.0 | 8.0 | 9.0 | 9.0 | 9.0 | 7.0 | 8.0 |
| | .500 | 4.5 | 9.0 | 9.0 | 5.0 | 9.0 | 9.0 | 6.0 | 9.0 | 7.0 | 6.0 | 9.0 | 9.0 | 6.0 | 7.0 |
| | .250 | 4.5* | 5.0 | 9.0 | 5.0 | 9.0 | 9.0 | 4.0 | 9.0 | 5.0 | 4.0 | 9.0 | 9.0 | 5.0 | 6.5 |
| | .125 | 1.0 | 0.0 | 8.3 | 5.0 | 9.0 | 9.0 | 2.0 | 9.0 | 3.0 | 3.0 | 9.0 | 6.0 | 5.0 | 3.5 |
| | .063 | 0.0 | 0.0 | 8.0 | 0.0 | 3.7 | 7.7 | 0.0 | 8.0 | 2.0 | 3.0 | 9.0 | 3.0 | 4.0 | 3.5 |
| | .032 | 0.0 | 0.0 | 2.0 | 0.0 | 0.0 | 0.0 | 0.0 | 7.0 | 0.0 | 2.0 | 9.0 | 0.0 | 0.0 | 0.0 |
| Calcium o-(4-isopropyl-4-methyl-5-thioxo-2-imidazolin-2-yl)benzoate | 2.000 | 6.0 | 9.0 | 9.0 | 9.0 | 9.0 | 9.0 | 8.0 | 9.0 | 9.0 | 9.0 | 9.0 | 9.0 | 8.0 | 9.0 |
| | 1.000 | 4.0 | 9.0 | 9.0 | 5.0 | 9.0 | 9.0 | 8.0 | 9.0 | 8.0 | 9.0 | 9.0 | 9.0 | 8.0 | 9.0 |
| | .500 | 3.0 | 0.0 | 9.0 | 5.0 | 9.0 | 9.0 | 6.0 | 9.0 | 7.0 | 9.0 | 9.0 | 9.0 | 6.0 | 6.0 |
| | .250 | 2.0 | 5.0 | 8.0 | 0.0 | 9.0 | 9.0 | 5.0 | 9.0 | 3.0 | 3.0 | 9.0 | 7.0 | 4.0 | 5.0 |
| | .125 | 0.0 | 0.0 | 8.0 | 0.0 | 5.5 | 5.0 | 3.0 | 9.0 | 2.0 | 4.0 | 9.0 | 6.0 | 4.0 | 0.5 |
| | .063 | 0.0 | 0.0 | 5.5 | 0.0 | 4.0 | 6.0 | 3.0 | 7.0 | 0.0 | 4.0 | 9.0 | 3.0 | 3.0 | 0.0 |
| | .032 | 0.0 | 0.0 | 0.0 | 0.0 | 2.0 | 2.0 | 2.0 | 0.0 | 0.0 | 2.0 | 9.0 | 4.0 | 2.0 | 0.0 |
| Methyl 2-(4-isopropyl-4-methyl-5-thioxo-2-imidazolin-2-yl)-p-toluate | 2.000 | 8.0 | 7.0 | 5.0 | 8.0 | 0.0 | 9.0 | 5.0 | 9.0 | 8.0 | 2.0 | 9.0 | 0.0 | 4.0 | 0.0 |
| | 1.000 | 8.0 | 7.0 | 5.0 | 9.0 | 0.0 | 9.0 | 3.0 | 9.0 | 6.0 | 0.0 | 9.0 | 0.0 | 2.0 | 0.0 |
| | .500 | 6.0 | 4.0 | 5.0 | 9.0 | 0.0 | 9.0 | 0.0 | 9.0 | 3.0 | 0.0 | 2.0 | 0.0 | 0.0 | 0.0 |
| | .250 | 2.0 | 0.0 | 0.0 | 9.0 | 0.0 | 8.0 | 0.0 | 9.0 | 0.0 | 0.0 | 2.0 | 0.0 | 0.0 | 0.0 |
| | .125 | 2.0 | 0.0 | 0.0 | 6.0 | 0.0 | 5.0 | 0.0 | 7.0 | 0.0 | 0.0 | 0.0 | 0.0 | 0.0 | 0.0 |
| | .063 | 0.0 | 0.0 | 0.0 | 4.0 | 0.0 | 2.0 | 0.0 | 3.0 | 0.0 | 0.0 | 0.0 | 0.0 | 0.0 | 0.0 |
| 2-Isopropyl-2,8-dimethyl-3-thio-5H-imidazo[2,1-a]-isoindole-3(2H),5-dione | 2.000 | 7.0 | 0.0 | 9.0 | 9.0 | 0.0 | 9.0 | 6.0 | 9.0 | 8.0 | 0.0 | 9.0 | 5.0 | 0.0 | 9.0 |
| | 1.000 | 7.0 | 6.0 | 9.0 | 6.0 | 4.0 | 9.0 | 5.0 | 6.0 | 8.0 | 7.0 | 9.0 | 2.0 | 7.0 | 9.0 |
| | .500 | 3.0 | 4.0 | 2.0 | 3.0 | 0.0 | 9.0 | 0.0 | | 4.0 | 6.0 | 9.0 | 1.0 | 6.0 | 9.0 |
| | .250 | 0.0 | 0.0 | 0.0 | 2.0 | 0.0 | 8.0 | 0.0 | | 0.0 | 2.0 | 9.0 | 0.0 | 4.0 | 4.0 |
| | .125 | 0.0 | 0.0 | 0.0 | 0.0 | 0.0 | 7.0 | 0.0 | 4.0 | 0.0 | 1.0 | 9.0 | 0.0 | 1.0 | 1.0 |
| | .063 | 0.0 | 0.0 | 0.0 | 0.0 | 0.0 | 7.0 | 0.0 | | 0.0 | 0.0 | 0.0 | 0.0 | 0.0 | 0.0 |
| 2-(4-Isopropyl-4-methyl-5-thioxo-2-imidazolin-2-yl)-p-toluic acid | 2.000 | 9.0 | 9.0 | 8.0 | 9.0 | 0.0 | 9.0 | 6.0 | 9.0 | 9.0 | 6.0 | 9.0 | 5.0 | 6.0 | 9.0 |
| | 1.000 | 5.0 | 3.0 | 8.0 | 9.0 | 0.0 | 9.0 | 3.0 | 9.0 | 5.0 | 4.0 | 9.0 | 2.0 | 4.0 | 9.0 |
| | .500 | 0.0 | 0.0 | 2.0 | 7.0 | 0.0 | 8.0 | 0.0 | 9.0 | 4.0 | 3.0 | | 1.0 | 2.0 | 6.0 |
| | .250 | 0.0 | 0.0 | 3.0 | 3.0 | 0.0 | 8.0 | 0.0 | 7.0 | 0.0 | 2.0 | 9.0 | 0.0 | 0.0 | 3.0 |

TABLE V-continued
PRE-EMERGENCE TESTS -- RATES IN KG/HA

| Compound | RATE | BARN YARD GR | GREEN FOX | P NUT SEDGE | WILD OATS | QUACK GRASS | FLD B INDWD | MRNGLRY SP | WILD MUST'D | VELVET LEAF | S BARLY LA | SUGAR BEETS | CORN FIELD | COTTON | RICE PADDY |
|---|---|---|---|---|---|---|---|---|---|---|---|---|---|---|---|
| Methyl 2-(4-isopropyl-4-methyl-5-thioxo-2-imidazolin-2-yl)-p-toluate and methyl 6-(4-isopropyl-4-methyl-5-thioxo-2-imidazolin-2-yl)-m-toluate | .125 | 0.0 | 0.0 | 0.0 | 0.0 | 0.0 | 8.0 | 0.0 | 7.0 | 0.0 | 0.0 | 9.0 | 0.0 | 0.0 | 0.0 |
|  | .063 | 0.0 | 0.0 | 0.0 | 0.0 | 0.0 | 4.0 | 0.0 | 4.0 | 0.0 | 0.0 | 5.0 | 0.0 | 0.0 | 0.0 |
|  | 2.000 | 9.0 | 6.0 | 6.0 | 9.0 | 2.0 | 9.0 | 2.0 | 9.0 | 8.0 | 0.0 | 9.0 | 0.0 | 0.0 | 3.0 |
|  | 1.000 | 7.0 | 2.0 | 2.0 | 8.0 | 0.0 | 9.0 | 0.0 | 9.0 | 7.0 | 0.0 | 9.0 | 0.0 | 0.0 | 2.0 |
|  | .500 | 6.0 | 0.0 | 0.0 | 7.0 | 0.0 | 9.0 | 0.0 | 9.0 | 2.0 | 0.0 | 9.0 | 0.0 | 0.0 | 0.0 |
|  | .250 | 2.0 | 0.0 | 0.0 | 6.0 | 0.0 | 8.0 | 0.0 | 8.0 | 0.0 | 0.0 | 4.0 | 0.0 | 0.0 | 0.0 |
|  | .125 | 0.0 | 0.0 | 0.0 | 0.0 | 0.0 | 3.0 | 0.0 | 0.0 | 0.0 | 0.0 | 2.0 | 0.0 | 0.0 | 0.0 |
|  | .063 | 0.0 | 0.0 | 0.0 | 3.0 | 0.0 | 0.0 | 0.0 | 0.0 | 0.0 | 0.0 | 0.0 | 0.0 | 0.0 | 0.0 |
| 2-(4-Isopropyl-4-methyl-5-thioxo-2-imidazolin-2-yl)-p-toluic acid and 6-(4-isopropyl-4-methyl-5-thioxo-2-imidazolin-2-yl)-m-toluic acid | 2.000 | 6.0 | 6.0 | 9.0 | 6.0 | 9.0 | 9.0 | 7.0 | 9.0 | 0.0 | 6.0 | 2.0 | 6.0 | 6.0 | 7.0 |
|  | 1.000 | 8.0 | 7.0 | 9.0 | 6.0 | 9.0 | 9.0 | 5.0 | 9.0 | 8.0 | 6.0 | 9.0 | 4.0 | 5.0 | 9.0 |
|  | .500 | 2.0 | 6.0 | 6.0 | 3.0 | 2.0 | 8.0 | 3.0 | 9.0 | 7.0 | 3.0 | 9.0 | 2.0 | 4.0 | 6.0 |
|  | .250 | 0.0 | 2.0 | 4.0 | 0.0 | 9.0 | 9.0 | 0.0 | 5.0 | 2.0 | 1.0 | 9.0 | 0.0 | 2.0 | 5.0 |
|  | .125 | 0.0 | 0.0 | 0.0 | 0.0 | 9.0 | 7.0 | 0.0 | 4.0 | 0.0 | 0.0 | 3.0 | 0.0 | 7.0 | 3.0 |
|  | .063 | 0.0 | 0.0 | 3.0 | 0.0 | 9.0 | 6.0 | 0.0 | 3.0 | 0.0 | 0.0 | 8.0 | 0.0 | 0.0 | 2.0 |
| 6-(4-Isopropyl-4-methyl-5-thioxo-2-imidazolin-2-yl)-m-toluic acid | 2.000 | 8.0 | 9.0 | 9.0 | 7.0 | 9.0 | 9.0 | 7.0 | 7.0 | 8.0 | 8.0 | 9.0 | 9.0 | 6.0 | 8.0 |
|  | 1.000 | 6.0 | 9.0 | 9.0 | 4.0 | 9.0 | 8.0 | 6.0 | 4.0 | 7.0 | 4.0 | 9.0 | 4.0 | 5.0 | 8.0 |
|  | .500 | 4.0 | 7.0 | 9.0 | 3.0 | 9.0 | 7.0 | 3.0 | 4.0 | 2.0 | 5.0 | 9.0 | 3.0 | 6.0 | 8.0 |
|  | .250 | 3.0 | 6.0 | 8.0 | 0.0 | 9.0 | 7.0 | 0.0 | 3.0 | 6.0 | 3.0 | 9.0 | 2.0 | 3.0 | 6.0 |
|  | .125 | 0.0 | 5.0 | 3.0 | 0.0 | 9.0 | 7.0 | 0.0 | 0.0 | 4.0 | 0.0 | 9.0 | 0.0 | 2.0 | 3.0 |
|  | .063 | 0.0 | 0.0 | 3.0 | 0.0 | 0.0 | 3.0 | 0.0 | 0.0 | 3.0 | 0.0 | 9.0 | 0.0 | 0.0 | 3.0 |
| Methyl 6-(4-isopropyl-4-methyl-5-thioxo-2-imidazolin-2-yl)-m-toluate | 2.000 | 5.0 | 0.0 | 3.0 | 0.0 | 0.0 | 8.0 | 4.0 | 0.0 | 5.0 | 0.0 | 9.0 | 0.0 | 0.0 | 4.0 |
|  | 1.000 | 3.0 | 0.0 | 2.0 | 7.0 | 0.0 | 4.0 | 2.0 | 0.0 | 2.0 | 0.0 | 9.0 | 0.0 | 0.0 | 3.0 |
|  | .500 | 3.0 | 0.0 | 2.0 | 7.0 | 0.0 | 3.0 | 2.0 | 0.0 | 8.0 | 0.0 | 9.0 | 0.0 | 0.0 | 2.0 |
|  | .250 | 0.0 | 0.0 | 0.0 | 7.0 | 0.0 | 0.0 | 0.0 | 0.0 | 0.0 | 0.0 | 7.0 | 0.0 | 0.0 | 2.0 |
|  | .125 | 0.0 | 0.0 | 0.0 | 5.0 | 0.0 | 0.0 | 0.0 | 0.0 | 0.0 | 0.0 | 8.0 | 0.0 | 0.0 | 0.0 |
|  | .063 | 0.0 | 0.0 | 0.0 | 0.0 | 0.0 | 0.0 | 0.0 | 0.0 | 0.0 | 0.0 | 9.0 | 0.0 | 0.0 | 0.0 |
| 2-Isopropyl-2,7-dimethyl-3-thio-5H-imidazo[2,1-a]isoindole-3(2H),5-dione | 2.000 | 8.0 | 9.0 | 9.0 | 7.0 | 9.0 | 9.0 | 8.0 | 0.0 | 8.0 | 8.0 | 9.0 | 6.0 | 6.0 | 9.0 |
|  | 1.000 | 8.0 | 9.0 | 9.0 | 5.0 | 9.0 | 9.0 | 6.0 | 7.0 | 8.0 | 9.0 | 9.0 | 5.0 | 5.0 | 8.0 |
|  | .500 | 5.0 | 6.0 | 7.0 | 3.0 | 9.0 | 9.0 | 5.0 | 5.0 | 6.0 | 5.0 | 9.0 | 4.0 | 3.0 | 6.0 |
|  | .250 | 2.0 | 6.0 | 6.0 | 0.0 | 4.0 | 7.0 | 5.0 | 2.0 | 5.0 | 4.0 | 9.0 | 2.0 | 3.0 | 5.0 |
|  | .125 | 0.0 | 6.0 | 6.0 | 0.0 | 0.0 | 6.0 | 3.0 | 2.0 | 3.0 | 3.0 | 9.0 | 3.0 | 0.0 | 4.0 |
|  | .063 | 0.0 | 0.0 | 3.0 | 0.0 | 0.0 | 4.0 | 2.0 | 0.0 | 5.0 | 0.0 | 9.0 | 3.0 | 0.0 | 3.0 |
| 9-Fluoro-1,9bα-dihydro-3-isopropyl-3-methyl-2-thio-5H-imidazo[2,1-a]isoindole-2(3H),5-dione | 2.000 | 5.0 | 0.0 | 9.0 | 0.0 | 9.0 | 9.0 | 8.0 | 8.0 | 8.0 | 0.0 | 9.0 | 6.0 | 2.0 | 0.0 |
|  | 1.000 | 2.0 | 0.0 | 6.0 | 0.0 | 9.0 | 4.0 | 8.0 | 9.0 | 7.0 | 0.0 | 9.0 | 7.0 | 3.0 | 0.0 |
|  | .500 | 0.0 | 0.0 | 6.0 | 0.0 | 9.0 | 9.0 | 8.0 | 9.0 | 8.0 | 0.0 | 9.0 | 5.0 | 7.0 | 0.0 |
|  | .250 | 0.0 | 0.0 | 4.0 | 0.0 | 9.0 | 9.0 | 8.0 | 8.0 | 2.0 | 0.0 | 7.0 | 4.0 | 6.0 | 0.0 |
|  | .125 | 0.0 | 0.0 | 2.0 | 0.0 | 7.0 | 9.0 | 8.0 | 7.0 | 2.0 | 0.0 | 9.0 | 0.0 | 6.0 | 0.0 |
|  | .063 | 0.0 | 0.0 | 0.0 | 0.0 | 3.0 | 8.0 | 8.0 | 6.0 | 5.0 | 0.0 | 9.0 | 0.0 | 4.0 | 0.0 |
| 9-Fluoro-2-isopropyl-2-methyl-3-thio-5H-imidazo[2,1-a]isoindole-3(2H),5-dione | 2.000 | 8.0 | 7.0 | 9.0 | 7.0 | 9.0 | 9.0 | 8.0 | 8.0 | 8.0 | 7.0 | 9.0 | 8.0 | 9.0 | 9.0 |
|  | 1.000 | 8.0 | 7.0 | 9.0 | 6.0 | 9.0 | 9.0 | 8.0 | 9.0 | 8.0 | 3.0 | 9.0 | 7.0 | 9.0 | 9.0 |
|  | .500 | 6.0 | 7.0 | 9.0 | 4.0 | 9.0 | 9.0 | 8.0 | 8.0 | 7.0 | 7.0 | 9.0 | 5.0 | 8.0 | 4.0 |
|  | .250 | 2.0 | 4.0 | 9.0 | 3.0 | 7.0 | 9.0 | 8.0 | 8.0 | 2.0 | 2.0 | 9.0 | 4.0 | 8.0 | 3.0 |
|  | .125 | 0.0 | 0.0 | 9.0 | 0.0 | 0.0 | 9.0 | 8.0 | 8.0 | 7.0 | 0.0 | 9.0 | 2.0 | 7.0 | 0.0 |
|  | .063 | 0.0 | 0.0 | 9.0 | 0.0 | 0.0 | 8.0 | 8.0 | 6.0 | 5.0 | 0.0 | 9.0 | 4.0 | 7.0 | 0.0 |
| 1,9bα-Dihydro-3-isopropyl-3-methyl-2-thio-5H-imidazo[2,1-a]isoindole-2(3H),5-dione | 2.000 | 8.0 | 7.0 | 9.0 | 5.0 | 9.0 | 9.0 | 8.0 | 8.0 | 8.0 | 3.0 | 9.0 | 4.0 | 7.0 | 5.0 |
|  | 1.000 | 7.0 | 5.0 | 9.0 | 3.0 | 9.0 | 9.0 | 8.0 | 8.0 | 7.0 | 2.0 | 9.0 | 2.0 | 7.0 | 5.0 |
|  | .500 | 4.0 | 6.0 | 8.0 | 0.0 | 6.0 | 8.0 | 6.0 | 7.0 | 3.0 | 0.0 | 9.0 | 2.0 | 7.0 | 3.0 |
|  | .250 | 2.0 | 2.0 | 8.0 | 0.0 | 3.0 | 8.0 | 5.0 | 8.0 | 0.0 | 0.0 | 9.0 | 0.0 | 7.0 | 3.0 |
|  | .125 | 0.0 | 0.0 | 7.0 | 0.0 | 0.0 | 8.0 | 5.0 | 8.0 | 0.0 | 0.0 | 9.0 | 0.0 | 6.0 | 0.0 |

TABLE V-continued
PRE-EMERGENCE TESTS – RATES IN KG/HA

| Compound | RATE | BARN YARD GR | GREEN FOX | P NUT SEDGE | WILD OATS | QUACK GRASS | FLD B INDWD | MRNGLRY SP | WILD MUSTD | VELVET LEAF | S BARLY LA | SUGAR BEETS | CORN FIELD | COTTON | RICE PADDY |
|---|---|---|---|---|---|---|---|---|---|---|---|---|---|---|---|
| 1,9bβ-Dihydro-3α-isopropyl-3-methyl-2-thio-5H-imidazo[2,1-a]isoindole-2(3H),5-dione | .063 | 0.0 | 0.0 | 7.0 | 0.0 | 0.0 | 8.0 | 6.0 | 9.0 | 0.0 | 0.0 | 9.0 | 0.0 | 6.0 | 0.0 |
|  | 2.000 | 8.0 | 8.0 | 9.0 | 7.0 | 9.0 | 9.0 | 7.0 | 9.0 | 8.0 | 6.0 | 9.0 | 3.0 | 8.0 | 2.0 |
|  | 1.000 | 8.0 | 8.0 | 9.0 | 7.0 | 9.0 | 9.0 | 8.0 | 9.0 | 8.0 | 6.0 | 9.0 | 3.0 | 8.0 | 2.0 |
|  | .500 | 8.0 | 9.0 | 8.0 | 5.0 | 8.0 | 9.0 | 8.0 | 9.0 | 7.0 | 5.0 | 9.0 | 2.0 | 8.0 | 2.0 |
|  | .250 | 6.0 | 7.0 | 5.0 | 2.0 | 7.0 | 8.0 | 8.0 | 8.0 | 5.0 | 2.0 | 9.0 | 0.0 | 7.0 | 2.0 |
|  | .125 | 0.0 | 0.0 | 5.0 | 0.0 | 5.0 | 9.0 | 7.0 | 8.0 | 2.0 | 0.0 | 9.0 | 0.0 | 6.0 | 2.0 |
|  | .063 | 0.0 | 0.0 | 2.0 | 0.0 | 0.0 | 7.0 |  | 8.0 | 2.0 | 0.0 | 9.0 | 0.0 | 4.0 | 2.0 |
| 3-Isopropyl-3-methyl-2-thio-5H-imidazo[2,1-a]isoindole-2(3H),5-dione | 2.000 | 5.0 | 0.0 | 9.0 | 0.0 | 0.0 | 8.0 | 7.0 | 8.0 | 7.0 | 0.0 | 9.0 | 0.0 | 6.0 | 0.0 |
|  | 1.000 | 0.0 | 0.0 | 8.0 | 0.0 | 0.0 | 7.0 | 7.0 | 9.0 | 7.0 | 0.0 | 9.0 | 0.0 | 3.0 | 0.0 |
|  | .500 | 0.0 | 0.0 | 0.0 | 0.0 | 0.0 | 0.0 | 7.0 | 8.0 | 6.0 | 0.0 | 9.0 | 0.0 | 2.0 | 0.0 |
|  | .250 | 0.0 | 0.0 | 0.0 | 0.0 | 0.0 | 0.0 | 0.0 | 7.0 | 0.0 | 0.0 | 7.0 | 0.0 | 0.0 | 0.0 |
|  | .125 | 0.0 | 0.0 | 0.0 | 0.0 | 0.0 | 0.0 | 0.0 | 5.0 | 0.0 | 0.0 | 6.0 | 0.0 | 0.0 | 0.0 |
|  | .063 | 0.0 | 0.0 | 0.0 | 0.0 | 0.0 | 0.0 | 0.0 |  | 0.0 | 0.0 | 6.0 | 0.0 | 0.0 | 0.0 |
| 2-(4-Isopropyl-4-methyl-5-thioxo-2-imidazolin-2-yl)-4,6-dimethylbenzoic acid | 2.000 | 9.0 | 9.0 | 9.0 | 4.0 | 7.0 | 9.0 | 8.0 | 9.0 | 8.0 | 3.0 | 9.0 | 0.0 | 9.0 | 3.0 |
|  | 1.000 | 7.0 | 9.0 | 9.0 | 2.0 | 0.0 | 9.0 | 7.0 | 9.0 | 8.0 | 3.0 | 9.0 | 3.0 | 8.0 | 2.0 |
|  | .500 | 3.0 | 9.0 | 9.0 | 0.0 | 3.0 | 8.0 | 6.0 | 9.0 | 8.0 | 0.0 | 9.0 | 2.0 | 7.0 | 0.0 |
|  | .250 | 2.0 | 5.0 | 7.0 | 0.0 | 2.0 | 7.0 | 5.0 | 9.0 | 6.0 | 0.0 | 9.0 | 0.0 | 5.0 | 0.0 |
|  | .125 | 0.0 | 0.0 | 0.0 | 0.0 | 0.0 | 3.0 | 2.0 | 6.0 | 3.0 | 0.0 | 9.0 | 0.0 |  | 0.0 |
|  | .063 | 0.0 | 0.0 | 0.0 | 0.0 | 0.0 | 0.0 | 0.0 | 6.0 | 2.0 | 0.0 | 9.0 | 0.0 |  | 0.0 |
| 2-Isopropyl-7-methoxy-2-methyl-3-thio-5H-imidazo[2,1-a]isoindole-3(2H),5-dione | 2.000 | 8.0 | 9.0 | 9.0 | 8.0 | 9.0 | 9.0 | 8.0 | 8.0 | 9.0 | 9.0 | 9.0 | 8.0 | 7.0 | 9.0 |
|  | 1.000 | 8.0 | 9.0 | 7.0 | 7.0 | 9.0 | 7.0 | 7.0 | 9.0 | 8.0 | 3.0 | 9.0 | 6.0 | 7.0 | 9.0 |
|  | .500 | 6.0 | 9.0 | 7.0 | 2.0 | 9.0 | 7.0 | 5.0 | 6.0 | 8.0 | 3.0 | 9.0 | 5.0 | 6.0 | 8.0 |
|  | .250 | 0.0 | 7.0 |  | 0.0 | 7.0 | 7.0 | 3.0 |  | 7.0 | 0.0 | 9.0 | 4.0 | 5.0 | 7.0 |
|  | .125 | 0.0 | 5.0 | 3.0 | 0.0 | 0.0 | 5.0 | 0.0 |  | 2.0 | 0.0 | 9.0 | 2.0 | 4.0 | 2.0 |
|  | .063 | 0.0 | 0.0 | 3.0 | 0.0 | 0.0 | 2.0 | 0.0 | 3.0 | 0.0 | 0.0 | 9.0 | 0.0 | 3.0 | 2.0 |
| 2-Isopropyl-2,6,8-trimethyl-3-thio-5H-imidazo[2,1-a]isoindole-3(2H),5-dione | 2.000 | 7.0 | 9.0 | 9.0 | 0.0 | 0.0 | 8.0 | 8.0 | 9.0 | 8.0 | 2.0 | 9.0 | 3.0 | 7.0 | 2.0 |
|  | 1.000 | 5.0 | 9.0 | 8.0 | 0.0 | 0.0 | 7.0 | 8.0 | 9.0 | 7.0 | 2.0 | 9.0 | 2.0 | 7.0 | 2.0 |
|  | .500 | 3.0 | 7.0 | 5.0 | 0.0 | 0.0 | 3.0 | 5.0 | 8.0 | 5.0 | 0.0 | 9.0 | 0.0 | 6.0 | 0.0 |
|  | .250 | 0.0 | 6.0 | 5.0 | 0.0 | 0.0 | 0.0 | 2.0 | 7.0 | 3.0 | 0.0 | 9.0 | 0.0 | 6.0 | 0.0 |
|  | .125 | 0.0 | 5.0 | 0.0 | 0.0 | 0.0 | 0.0 | 0.0 | 0.0 | 0.0 | 0.0 | 9.0 | 0.0 | 5.0 | 0.0 |
|  | .063 | 0.0 | 0.0 | 0.0 | 0.0 | 0.0 | 0.0 | 0.0 | 0.0 | 0.0 | 0.0 | 9.0 | 0.0 | 2.0 | 0.0 |

What we claim is:
1. A compound having the structure:

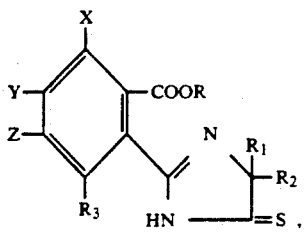

wherein R is hydrogen;
$C_1-C_{12}$ alkyl optionally substituted with one of the following groups: $C_1-C_4$ alkoxy, halogen, hydroxyl, $C_3-C_6$ cycloalkyl, benzyloxy, furyl, phenyl, halophenyl, $C_1-C_4$ alkylphenyl, $C_1-C_4$ alkoxyphenyl, nitrophenyl, carboxyl, $C_1-C_3$ alkoxycarbonyl, cyano or tri($C_1-C_3$)alkylammonium;
$C_3-C_{12}$ alkenyl optionally substituted with one of the following groups: $C_1-C_3$ alkoxy, phenyl, halogen, or $C_1-C_3$ alkoxycarbonyl or with two $C_1-C_4$ alkoxy groups or two halogen atoms;
$C_3-C_6$ cycloalkyl optionally substituted with one or two $C_1-C_3$ alkyl groups;
$C_3-C_{10}$ alkynyl; or, a cation;
$R_1$ and $R_2$ each represent $C_1-C_3$ akyl or cyclopropyl, with the proviso that the sum of the number of carbon atoms in $R_1$ and $R_2$ is 2 to 5; and when $R_1$ and $R_2$ are taken together with the carbon to which they are attached, they may form a $C_3-C_6$ cycloalkyl ring optionally substituted with methyl;
X is hydrogen, halogen, or methyl;
Y and Z are each hydrogen, halogen, $C_1-C_6$ alkyl, $C_1-C_4$ hydroxyalkyl, $C_1-C_6$ alkoxy, $C_1-C_4$ alkylthio, phenoxy, $C_1-C_4$ haloalkyl, $OCF_2CHF_2$, $OCF_3$, $OCHF_2$, nitro, cyano, $NR_4R_5$, $C_3-C_8$ straight or branched alkenyloxy optionally substituted with one to three halogens, $C_3-C_8$ straight or branched alkynyloxy optionally substituted with one to three halogens, or phenyl optionally substituted with one $C_1-C_4$ alkyl, $C_1-C_4$ alkoxy or halogen;
$R_3$ is hydrogen, halogen, $C_1-C_4$ alkyl, $C_1-C_4$ alkylthio, $C_1-C_4$ alkoxy, $CF_3$, $NO_2$, $OCF_3$, $OCHF_2$ or $OCF_2CHF_2$;
$R_4$ is hydrogen or $C_1-C_4$ alkyl;
$R_5$ is $C_1-C_4$ alkyl;
And, when taken together, Y and Z may form a ring in which YZ is represented by
(1) the structure: $-(CH_2)_n-$, where n is an integer of 2, 3 or 4; or
(2) by the structure:

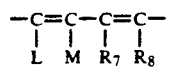

where, L, M $R_7$ and $R_8$ each represent hydrogen, halogen, $C_1-C_4$ or $C_1-C_3$ alkoxy, and X is hydrogen;
and when $R_1$ and $R_2$ are not the same, the optical isomers thereof and except when R is a cation, the acid addition salts thereof.
2. A compound according to claim 1 having the structure:

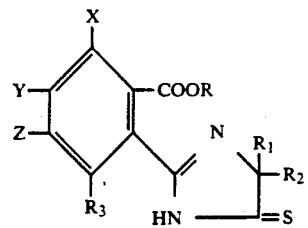

wherein R, $R_1$, $R_2$, $R_3$, X, Y and Z are as defined in said claim 1, except that when R is a cation, it is a cation of alkali metals, alkaline earth metals, manganese, copper, iron, zinc, cobalt, lead, silver, nickel, ammonium or organic ammonium.
3. A compound according to claim 1 wherein $R_1$ is $CH_3$; $R_2$ is $CH(CH_3)_2$; and R is as described in claim 1 and X, Y, Z and $R_3$ each represent hydrogen, halogen, $C_1-C_3$ alkoxy or $C_1-C_3$ alkyl; and the optical isomers thereof and except when R is a cation, the acid addition salts thereof.
4. Compounds according to claim 1:
o-(4-isopropyl-4-methyl-5-thioxo-2-imidazolin-2-yl)-benzoic acid;
methyl o-(4-isopropyl-4-methyl-5-thioxo-2-imidazolin-2-yl)benzoate;
3-fluoro-2-(4-isopropyl-4-methyl-5-thioxo-2-imidazolin-2-yl)benzoic acid;
(R)-(+)-o-(4-isopropyl-4-methyl-5-thioxo-2-imidazolin-2-yl)-benzoic acid;
(R)-(+)-methyl o-(4-isopropyl-4-methyl-5-thioxo-2-imidazolin-2-yl)benzoate;
benzyl o-(4-isopropyl-4-methyl-5-thioxo-2-imidazolin-2-yl)benzoate;
isopropylammonium o-(4-isopropyl-4-methyl-5-thioxo-2-imidazolin-2-yl)benzoate;
benzyltrimethylammonium o-(4-isopropyl-4-methyl-5-thioxo-2-imidazolin-2-yl)benzoate;
2-propynyl o-(4-isopropyl-4-methyl-5-thioxo-2-imidazolin-2-yl)benzoate;
ethyl o-(4-isopropyl-4-methyl-5-thioxo-2-imidazolin-2-yl)benzoate;
furfuryl o-(4-isopropyl-4-methyl-5-thioxo-2-imidazolin-2-yl)benzoate;
methyl 6-(4-isopropyl-4-methyl-5-thioxo-2-imidazolin-2-yl)m-toluate;
2-(4-isopropyl-4-methyl-5-thioxo-2-imidazolin-2-yl)-p-toluic acid;
methyl 2-(4-isopropyl-4-methyl-5-thioxo-2-imidazolin-2-yl)-p-toluate and methyl 6-(4-isopropyl-4-methyl-5-thioxo-2-imidazolin-2-yl)-m-toluate;
2-(4-isopropyl-4-methyl-5-thioxo-2-imidazolin-2-yl) -p-toluic acid and 6-(4-isopropyl-4-methyl-5-thioxo-2-imidazolin-2-yl)-m-toluic acid;
6-(4-isopropyl-4-methyl-5-thioxo-2-imidazolin-2-yl) -m-toluic acid;
methyl o-(4-isopropyl-4-methyl-5-thioxo-2-imidazolin-2-yl)benzoate hydrochloride;
isopropyl o-(4-isopropyl-4-methyl-5-thioxo-2-imidazolin-2-yl)benzoate;
sodium o-(4-isopropyl-4-methyl-5-thioxo-2-imidazolin-2-yl)benzoate; or
calcium o-(4-isopropyl-4-methyl-5-thioxo-2-imidazolin-2-yl)benzoate.
5. A compound according to claim 4, o-(4-isopropyl-4-methyl-5-thioxo-2-imidazolin-2-yl)benzoic acid.

6. A compound according to claim 4, methyl o-(4-isopropyl-4-methyl-5-thioxo-2-imidazolin-2-yl)benzoate.

7. A compound according to claim 4, (R)(+(+)-o-(4-isopropyl-4-methyl-5-thioxo-2-imidazolin-2-yl)benzoic acid.

8. A compound according to claim 4, (R)-(+)-methyl o-(4-isopropyl-4-methyl-5-thioxo-2-imidazolin-2-yl)benzoate.

9. A compound according to claim 4, benzyl o-(4-isopropyl-4-methyl-5-thioxo-2-imidazolin-2-yl)benzoate.

10. A compound according to claim 4, isopropylammonium o-(4-isopropyl-4-methyl-5-thioxo-2-imidazolin-2-yl)benzoate.

11. A compound according to claim 4, benzyltrimethylammonium o-(4-isopropyl-4-methyl-5-thioxo-2-imidazolin-2-yl)benzoate.

12. A compound according to claim 4, isopropyl o-(4-isopropyl-4-methyl-5-thioxo.2-imidazolin-2-yl)benzoate.

13. A method for the control of undesirable monocotyledonous and dicotyledonous plant species comprising applying to the foliage of the plants or to soil containing seeds or other propagating organs thereof, a herbicidally effective amount of a compound having the structure:

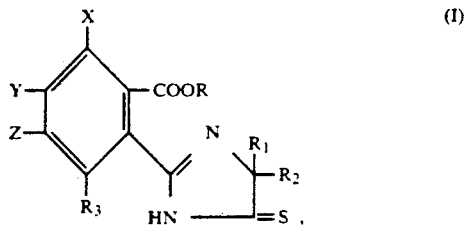

wherein R is hydrogen;
  $C_1-C_{12}$ alkyl optionally substituted with one of the following groups: $C_1-C_4$ alkoxy, halogen, hydroxyl, $C_3-C_6$ cycloalkyl, benzyloxy, furyl, phenyl, halophenyl, $C_1-C_4$ alkylphenyl, $C_1-C_4$ alkoxyphenyl, nitrophenyl, carboxyl, $C_1-C_3$ alkoxycarbonyl, cyano or tri($C_1-C_3$)alkylammonium;
  $C_3-C_{12}$ alkenyl optionally substituted with one of the following groups: $C_1-C_3$ alkoxy, phenyl, halogen, or $C_1-C_3$ alkoxycarbonyl or with two $C_1-C_4$ alkoxy groups or two halogen atoms;
  $C_3-C_6$ cycloalkyl optionally substituted with one or two $C_1-C_3$ alkyl groups;
  $C_3-C_{10}$ alkynyl; or, a cation;
$R_1$ and $R_2$ each represent $C_1-C_3$ alkyl or cyclopropyl, with the privoso that the sum of the number of carbon atoms in $R_1$ and $R_2$ is 2 to 5; and when $R_1$ and $R_2$ are taken together with the carbon to which they are attached, they may form a $C_3-C_6$ cycloalkyl ring optionally substituted with methyl;
X is hydrogen, halogen or methyl;
Y and Z are each hydrogen, halogen, $C_1-C_6$ alkyl, $C_1-C_4$ hydroxyalkyl, $C_1-C_6$ alkoxy, $C_1-C_4$ alkylthio, phenoxy, $C_1-C_6$ haloalkyl, $OCF_2CHF_2$, $OCF_3$, $OCHF_2$, nitro, cyano, $NR_4R_5$, $C_3-C_8$ straight or branched alkenyloxy optionally substituted with one to three halogens, $C_3-C_8$ straight or branched alkynyloxy optionally substituted with one to three halogens, or phenyl optionally substituted with one $C_1-C_4$ alkyl, $C_1-C_4$ alkoxy or halogen;

$R_3$ is hydrogen, halogen, $C_1-C_4$ alkyl, $C_1-C_4$ alkylthio, $C_1-C_4$ alkoxy, $CF_3$, $NO_2$, $OCF_3$, $OCHF_2$ or $OCF_2CHF_2$;
$R_4$ is hydrogen or $C_1-C_4$ alkyl;
$R_5$ is $C_1-C_4$ alkyl;
And, when taken together, Y and Z may form a ring in which YZ is represented by
  (1) the structure: $-(CH_2)_n-$, where n is an integer of 2, 3 or 4; or
  (2) by the structure:

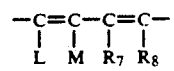

where, L, M, $R_7$ and $R_8$ each represent hydrogen, halogen, $C_1-C_4$ alkyl or $C_1-C_3$ alkoxy, and X is hydrogen;
and when $R_1$ and $R_2$ are not the same, the optical isomers thereof and except when R is a cation, the acid addition salts thereof.

14. A method according to claim 16, wherein the compound is:
o-(4-isopropyl-4-methyl-5-thioxo-2-imidazolin-2-yl)benzoic acid;
methyl o-(4-isopropyl-4-methyl-5-thioxo-2-imidazolin-2-yl)benzoate;
3-fluoro-2-(4-isopropyl-4-methyl-5-thioxo-2-imidazolin-2-yl)benzoic acid;
(R)-(+)-o-(4-isopropyl-4-methyl-5-thioxo-2-imidazolin-2-yl)benzoic acid;
(R)-(+)-methyl o-(4-isopropyl-4-methyl-5-thioxo-2-imidazolin-2-yl)benzoate;
benzyl o-(4-isopropyl-4-methyl-5-thioxo-2-imidazolin-2-yl)benzoate;
isopropylammonium o-(4-isopropyl-4-methyl-5-thioxo-2-imidazolin-2-yl)benzoate;
benzyltrimethylammonium o-(4-isopropyl-4-methyl-5-thioxo-2-imidazolin-2-yl)benzoate;
2-propynyl o-(4-isopropyl-4-methyl-5.thioxo-2-imidazolin-2-yl)benzoate;
ethyl o-(4-isopropyl-4-methyl-5-thioxo-2-imidazolin-2-yl)benzoate;
furfuryl o-(4-isopropyl-4-methyl-5-thioxo-2-imidazolin-2-yl)benzoate;
methyl 6-(4-isopropyl-4-methyl-5-thioxo-2-imidazolin-yl)m-toluate;
2-(4-isopropyl-4-methyl-5-thioxo-2-imidazolin-2-yl)-p-toluic acid;
methyl 2-(4-isopropyl-4-methyl-5-thioxo-2-imidazolin-b 2-yl)-p-toluate and methyl 6-(4-isopropyl-4-methyl-5-thioxo-2-imidazolin-2-yl)-m-toluate;
2-(4-isopropyl-4-methyl-5-thioxo-2-imidazolin-2-yl) p-toluic acid and 6-(4-isopropyl-4-methyl-5-thioxo-2-imidazolin-2-yl)-m-toluic acid;
6-(4-isopropyl-4-methyl-5-thioxo-2-imidazolin-2-yl) -m-toluic acid;
methyl o-(4-isopropyl-4-methyl-5-thioxo-2-imidazolin-2-yl)benzoate hydrochloride;
isopropyl o-(4-isopropyl-4-methyl-5-thioxo-2-imidazolin-2-yl)benzoate;
sodium o-(4-isopropyl-4-methyl-5-thioxo-2-imidazolin-2-yl)benzoate; or
calcium o-(4-isopropyl-4-methyl-5-thioxo-2-imidazolin-2-yl)benzoate.

15. A method according to claim 14, wherein the compound is applied to the foliage of the plants at a rate of from 0.032 to 8.0 kg/ha.

16. A method according to claim 14, wherein said compound is applied to soil containing seed or other propagating organs of undesirable plants at a rate between about 0.032 and 8.0 kg/ha.

17. A method for the selective preemergence control of quackgrass in the presence of graminaceous crops comprising, applying to the soil in which the crops have been planted, a quackgrass inhibiting amount of a compound:

isopropyl o-(4-isopropyl-4-methyl-5-thioxo-2-imidazolin-2-yl)benzoate;

methyl 3-fluoro-2-(4-isopropyl-4-methyl-5-thioxo-2-imidazolin-2-yl)benzoate;

2-propynyl o-(4-isopropyl-4-methyl-5-thioxo-2-imidazolin-2-yl)benzoate;

ethyl o-(4-isopropyl-4-methyl-5-thioxo-2-imidazolin-2-yl)benzoate;

furfuryl o-(4-isopropyl-4-methyl-5-thioxo-2-imidazolin-2-yl)benzoate;

o-(4-isopropyl-4-methyl-5-thioxo-2-imidazolin-2-yl)benzoic acid;

(R)-(+)-methyl o-(4-isopropyl-4-methyl-5-thioxo-2-imidazolin-2-yl)benzoate;

Benzyl o-(4-isopropyl-4-methyl-5-thioxo-2-imidazolin-2-yl)benzoate;

3-fluoro-2-(4-isopropyl-4-methyl-5-thioxo-2-imidazolin-2-yl)benzoic acid;

(R)-(+)-o-(4-isopropyl-4-methyl-5-thioxo-2-imidazolin-2-yl)benzoic acid; or benzyltrimethylammonium o-(4-isopropyl-4-methyl-5-thioxoimidazolin-2-yl)benzoate.

18. A method according to claim 17, wherein said compound is applied at a rate of from 0.063 to 2.0 kg/ha.

19. A method according to claim 18 wherein the compound is isopropyl o-(4-isopropyl-4-methyl-5-thioxo-2-imidazolin-2-yl)benzoate.

20. A herbicidal composition comprising an inert diluent and a herbicidally effective amount of a compound of the structure:

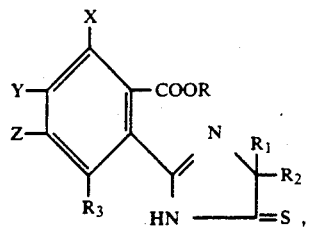

(I)

wherein R is hydrogen
  $C_1$-$C_{12}$ alkyl optionally substituted with one of the following groups: $C_1$-$C_4$ alkoxy, halogen, hydroxyl, $C_3$-$C_6$ cycloalkyl, benzyloxy, furyl, phenyl, halophenyl, $C_1$-$C_4$ alkylphenyl, $C_1$-$C_4$ alkoxyphenyl, nitrophenyl, carboxyl, $C_1$-$C_3$ alkoxycarbonyl, cyano or tri($C_1$-$C_3$)alkylammonium;
  $C_3$-$C_{12}$ alkenyl optionally substituted with one of the following groups: $C_1$-$C_3$ alkoxy, phenyl, halogen, or $C_1$-$C_3$ alkoxycarbonyl or with two $C_1$-$C_4$ alkoxy groups or two halogen atoms;
  $C_3$-$C_6$ cycloalkyl optionally substituted with one or two $C_1$-$C_3$ alkyl groups;
  $C_3$-$C_{10}$ alkynyl; or, a cation;
  $R_1$ and $R_2$ each represent $C_1$-$C_3$ alkyl or cyclopropyl, with the proviso that the sum of the number of carbon atoms in $R_1$ and $R_2$ is 2 to 5; and when $R_1$ and $R_2$ are taken together with the carbon to which they are attached, they may form a $C_3$-$C_6$ cycloalkyl ring optionally substituted with methyl;
  X is hydrogen, halogen or methyl;
  Y and Z are each hydrogen, halogen, $C_1$-$C_6$ alkyl, $C_1$-$C_4$ hydroxyalkyl, $C_1$-$C_6$ alkoxy $C_1$-$C_4$ alkylthio, phenoxy, $C_1$-$C_4$ haloalkyl, $OCF_2CHF_2$, $OCF_3$, $OCHF_2$, nitro, cyano, $NR_4R_5$, $C_3$-$C_8$ straight or branched alkenyloxy optionally substituted with one to three halogens, $C_3C_8$ straight or branched alkynyloxy optionally substituted with one to three halogens, or phenyl optionally substituted with one $C_1$-$C_4$ alkyl, $C_1$-$C_4$ alkoxy or halogen;
  $R_3$ is hydrogen, halogen, $C_1$-$C_4$ alkyl, $C_1$-$C_4$ alkylthio, $C_1$-$C_4$ alkoxy, $CF_3$, $NO_2$, $OCF_3$, $OCHF_2$ or $OCF_2CHF_2$;
  $R_4$ is hydrogen or $C_1$-$C_4$ alkyl;
  $R_5$ is $C_1$-$C_4$ alkyl;
  And, when taken together, Y and Z may form a ring in which YZ is represented by
  (1) the structure: —$(CH_2)_n$—, where n is an integer of 2, 3 or 4; or
  (2) by the structure:

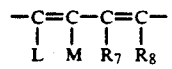

where, L, M, $R_7$ and $R_8$ each represent hydrogen, halogen, $C_1$-$C_4$ alkyl or $C_1$-$C_3$ alkoxy, and X is hydrogen;
and when $R_1$ and $R_2$ are not the same, the optical isomers thereof and except when R is a cation, the acid addition salts thereof.

* * * * *

UNITED STATES PATENT AND TRADEMARK OFFICE
CERTIFICATE OF CORRECTION

PATENT NO. : 5,073,186

DATED : December 17, 1991

INVENTOR(S) : Marinus Los

It is certified that error appears in the above-identified patent and that said Letters Patent is hereby corrected as shown below:

In the claims, column 67, claim 13, line 61 should read:

--"thio, phenoxy, $C_1$-$C_4$ haloalkyl,...."--

Column 68, claim 14, lines 52-53 should read:
--"....-2-imidazolin-2-yl)...."--

Signed and Sealed this

Thirteenth Day of April, 1993

Attest:

STEPHEN G. KUNIN

Attesting Officer

Acting Commissioner of Patents and Trademarks